US011325969B2

(12) United States Patent
Levy et al.

(10) Patent No.: US 11,325,969 B2
(45) Date of Patent: May 10, 2022

(54) FGL2 ANTIBODIES AND BINDING FRAGMENTS THEREOF AND USES THEREOF

(71) Applicant: Veritas Therapeutics Inc., Thornhill (CA)

(72) Inventors: Gary Levy, Thornhill (CA); Ramzi Khattar, Toronto (CA); Andrzej Chruscinski, Toronto (CA); Barbara Vanderhyden, Ottawa (CA); Curtis McCloskey, Ottawa (CA)

(73) Assignee: Veritas Therapeutics Inc., Thornhill (CA)

( * ) Notice: Subject to any disclaimer, the term of this patent is extended or adjusted under 35 U.S.C. 154(b) by 0 days.

(21) Appl. No.: 16/642,685

(22) PCT Filed: May 3, 2018

(86) PCT No.: PCT/CA2018/050527
§ 371 (c)(1),
(2) Date: Feb. 27, 2020

(87) PCT Pub. No.: WO2019/041024
PCT Pub. Date: Mar. 7, 2019

(65) Prior Publication Data

US 2020/0190176 A1 Jun. 18, 2020

Related U.S. Application Data

(60) Provisional application No. 62/551,385, filed on Aug. 29, 2017.

(51) Int. Cl.
*C07K 16/18* (2006.01)
*G01N 33/574* (2006.01)
*A61K 39/00* (2006.01)
*A61P 35/00* (2006.01)

(52) U.S. Cl.
CPC .............. *C07K 16/18* (2013.01); *A61P 35/00* (2018.01); *G01N 33/57484* (2013.01); *A61K 2039/505* (2013.01); *C07K 2317/565* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 7,915,390 | B2 * | 3/2011 | Li | A61P 25/00 530/388.22 |
| 7,983,850 | B2 * | 7/2011 | Shaughnessy | A61P 35/00 702/19 |
| 10,415,017 | B2 * | 9/2019 | O'Neill | C07K 16/40 |
| 2010/0298418 | A1 * | 11/2010 | Levy | G01N 33/5761 514/44 R |
| 2011/0052488 | A1 * | 3/2011 | Dennis, Jr. | A61K 38/16 424/1.49 |

FOREIGN PATENT DOCUMENTS

| | | | |
|---|---|---|---|
| CA | 2682429 | A1 | 11/2010 |
| WO | 2015/143343 | | 3/2015 |

OTHER PUBLICATIONS

International Preliminary Report on Patentability dated Mar. 12, 2020 in the corresponding International Patent Application No. PCT/CA2018/050527, pp. 1-7.
Rabizadeh et al., "Increased Activity of Cell Membrane-Associated Prothrombinase, Fibrinogen-Like Protein 2, in Peripheral Blood Mononuclear Cells of B-Cell Lymphoma Patients", PLos One, Oct. 2014, vol. 9, Issue 10, pp. 1-5.
Yan et al., "FGL2 as a Multimodality Regulator of Tumor-Mediated Immune Suppression and Therapeutic Target in Gliomas", JNCI J Natl Cancer Inst (2015) 107(8): djv137, pp. 1-10.
Project summary: Catalyst Program; Published online on May 4, 2017 at https://biocanrx.com/catalyst-project-vanderhyden.

* cited by examiner

*Primary Examiner* — Marianne P Allen
(74) *Attorney, Agent, or Firm* — Bereskin & Parr LLP/S.E.N.C.R.L., s.r.l.; Ainslie Parsons

(57) ABSTRACT

The disclosure is directed to antibodies and binding fragments thereof that specifically bind FGL2. The disclosure is also directed to uses of the antibodies and binding fragments thereof for treating cancer.

9 Claims, 21 Drawing Sheets

Specification includes a Sequence Listing.

Certificate of Analysis - Anti-FGL2 Antibody (9D8):

9D8 - Western Blot and Coomassie Blue Stain

Sandwich ELISA

A

B

A.

B.

C.
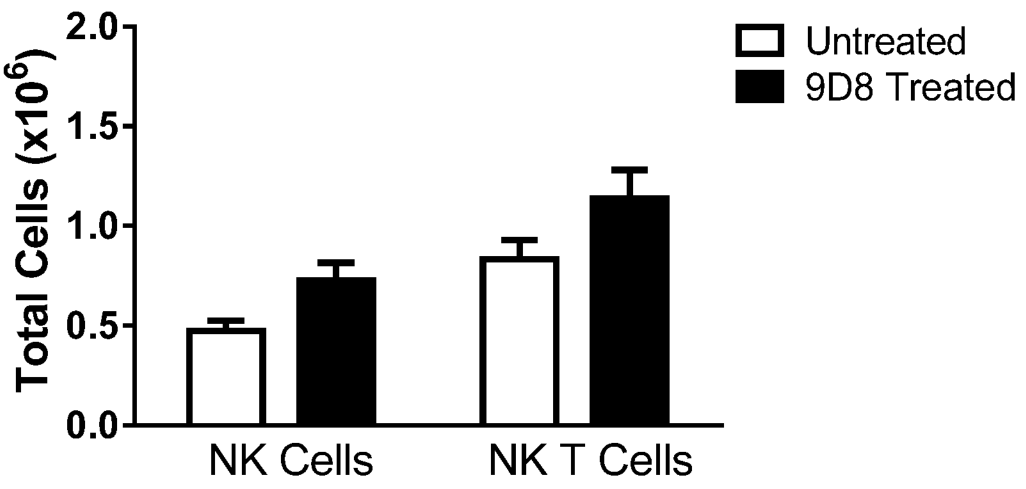
Figure 9 con't

A.

B.

C.
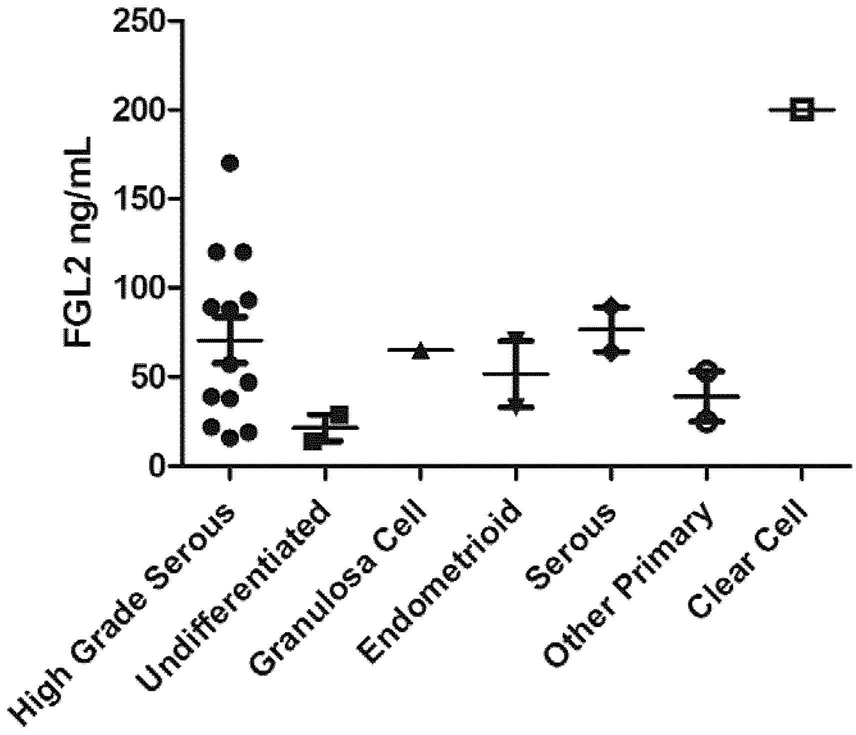
Figure 15 con't

FGL2 ANTIBODIES AND BINDING FRAGMENTS THEREOF AND USES THEREOF

CROSS-REFERENCE TO RELATED APPLICATION

This application is a national phase entry of PCT/CA2018/050527 filed May 3, 2018 (which designates the U.S.) which claims the benefit of priority to U.S. Provisional Application No. 62/551,385 filed Aug. 29, 2017, the contents of which are incorporated herein by reference in their entirety.

INCORPORATION OF SEQUENCE LISTING

A computer readable form of the Sequence Listing "25306-P53443US01_SequenceListing.txt" (77,824 bytes), submitted via EFS-WEB and created on Feb. 24, 2020, is herein incorporated by reference.

FIELD

This disclosure relates generally to FGL2 antibodies and binding fragments thereof, and to methods and uses of these antibodies and binding fragments.

BACKGROUND

Ongoing low-grade inflammatory responses may drive the infiltration of immunosuppressive leukocytes, such as, Treg, M2 macrophage and myeloid derived suppressor cells (MDSC) that render protective T cell immune responses refractory to tumor antigens to promote carcinogenesis (Mantovani et al, 2008; Karin and Grete, 2005; Curtin et al, 2008; Sica et al, 2006; Watanabe et al, 2008). Local IFNγ-driven immune checkpoint expression can inhibit adaptive immunity (Care et al, 2015). The immunoregulatory effector functions of $CD4^+CD25^+FoxP3^+$ Treg (Twyman-Sait Victor et al, 2015), M2 macrophage (Colegio et al, 2014) and MDSC (Cui et al, 2013; Wilcox et al, 2009; McClanahan et al, 2015) increase metastatic and tumorigenic potential, while concurrently reduce patient prognosis. Moreover, tumor-associated immunoregulatory cues can lead to the conversion of proinflammatory $CD4^+$ T cells to Treg (Ohaegbulam et al, 2015) and can polarize macrophages to an immunoregulatory M2-like phenotype (Van Overmeire et al, 2015; Lewis and Pollard, 2006).

Infiltrating immunoregulatory leukocytes serve to further propagate immune suppression through secretion of immunosuppressive cytokines (TGF-β, IL-10 and PGE2) and inducing the upregulation of inhibitory death receptors on proinflammatory leukocytes such as, PD-1, TIGIT, LAG-3, CD160, 2B4, TIM-3 and CTLA-4 (Butt and Mills, 2014). PD-1 upregulation is observed in a number of human cancers including, melanoma, non-small-cell lung cancer, renal cell carcinoma and bladder cancer (Tsai and Daud, 2015; Dang et al, 2015; Joseph et al, 2015; Aoun et al, 2015). In human hepatocellular carcinoma (HCC), upregulated expression of PD-L1 on hepatoma and hepatic stellate cells is observed, which coincides with the induction of apoptosis in infiltrating $CD8^+$ cytotoxic T lymphocytes through the PD-1/SHP-2/p-stat1/Tbet axis (Li et al, 2015). Such interactions are not restricted to solid tumors, as in a murine model of chronic lymphocytic leukemia (CLL), T cells appear to exhibit PD-L1 mediated impairment through direct cell-cell contact with malignant CLL cells (Ramsay et al, 2008). Tumor associated dendritic cells (DC) express low levels of costimulatory molecules such as, CD80, CD86 and CD40 and high levels of PD-L1 and IDO in a murine transgenic adenocarcinoma model of mouse prostate model, impairing tumor antigen presentation and anergizing tumor-specific CTL (Sharma et al, 2007). Potential strategies to adoptively transfer in vitro derived tumor specific T cells to kill cancer cells is a promising therapy for the treatment of solid-tumor cancers, however, these strategies do not circumvent the potential for immune exhaustion within the tumor microenvironment. Thus, it may be necessary to inhibit immune checkpoint, such as PD-L1, TIM3 and TIGIT to promote the survival and proliferation of cancer-specific T cell responses to reverse the effects of cancer-associated T cell exhaustion for the effective management of neoplastic growth.

Promotion of anti-tumor activity through the use of vaccination has been shown to have limited effectiveness through the likely immunosuppressive nature of the tumor microenvironment (Chen and Mellman, 2013). In solid tumor-bearing animal models, co-expression of PD-1 and TIM3 is observed in tumor infiltrating lymphocytes with failure to proliferate and produce IL-2, TNFα, IFNγ and dual blockade of PD-1 and TIM3 restored exhausted $CD8^+$ T cells (Sakuishi et al, 2010). Antibody mediated blockade of PD1 and Tim3 partially reverses T cell exhaustion in colon carcinoma tumors in mice (Sakuishi et al, 2010). Blockade of PD-1/PDL1 augments anti-tumor immunity in solid tumors. Cytotoxic T lymphocytes have been shown to demonstrate an exhausted phenotype with defective immunologic synapse formation and the infiltration of immunosuppressive myeloid cells. Anti-PD-L1 reduced the spleen size in AT of 4×10^7 CLL cells from leukemic Eu-TCL1 mice with lower tumor load (McClanahan et al, 2015). The immunoregulatory death receptor TIGIT is highly expressed in colon adenocarcinoma, uterine corpus endometroid carcinoma, breast carcinoma and renal clear cell carcinoma. Moreover, TIGIT expression was correlated with CD3ε and CD8, suggesting that exhausted CTL expressed high levels of TIGIT. PD1/TIGIT was found to be highly expressed on tumor-infiltrating T cells. Co-administration of PD-L1 antibody and TIGIT antibody led to tumor regression with enhanced expression of both TNFα and IFNγ (Johnston et al, 2014). Tumor samples from melanoma patients express high levels of TIGIT and combined blockade of TIGIT and PD-L1 increased T cell proliferation and cytokine production (Johnston et al, 2014; Chauvin et al, 2015). Several monoclonal antibody immune checkpoint inhibitors are currently being investigated in clinical trials.

FGL2/fibroleukin, was first cloned from cytotoxic T lymphocytes and classified as a member of the fibrinogen superfamily due to its protein (aa) sequence identity (36%) with fibrinogen β and γ chains (Koyama et al, 1987). In cells of the reticuloendothelial system, macrophages, B cells and endothelial cells, FGL2 is expressed predominantly as a membrane-associated protein with prothrombinase activity capable of cleaving prothrombin to thrombin. Generated thrombin can subsequently cleave fibrinogen to fibrin.

Subsets of $CD4^+$ and $CD8^+$ T and Treg secrete FGL2, which has immunosuppressive properties: inhibiting maturation of bone marrow-derived DC, suppressing T cell proliferation, and inducing B cell apoptosis (Marazzi et al, 1998, Li et al, 2010; Shalev et al, 2008; Shalev et al, 2009; Chan et al, 2009; Chan et al, 2003; Lui et al, 2008). Targeted deletion of fgl2 leads to impaired Treg activity associated with enhanced reactivity of DC, T and B cells and manifestation of autoimmune glomerulonephritis (Shalev et al, 2008). The C-terminal globular portion of FGL2 accounts for the suppressive activity of FGL2 (Chan et al, 2009). Recently, a subset of inducible and natural Tregs expressing TIGIT have been identified (Joller et al, 2014). Ligation of TIGIT to CD155 on antigen-presenting cells (APCs) was reported to lead to increased expression of FGL2, resulting in suppression of both $T_H1$ and $T_H17$ responses in vivo (Joller et al, 2014). It has also been demonstrated that FGL2 plays a critical role in T cell exhaustion in both human and experimental models of chronic viral hepatitis. Cancers adapt to immune surveillance by induction of T cell exhaustion (Zehn and Wherry, 2015; Severson et al, 2015). IDO1, LAG3 and FGL2 was associated with Diffuse Large B cell Lymphoma to a higher extent than PD-L1 and PD-L2 (Twyman-Saint Victor, 2015).

FGL2 mRNA has been detected in cervical, pancreatic, ovarian, uterine, esophageal, melanoma, glioblastoma head and neck, colorectal, bladder, lung, prostate, sarcoma, breast, liver and renal malignancies and acute myelogeneous leukemia (Su et al, 2008).

High-grade serous ovarian cancer (HGSC) is the most common and lethal subtype of ovarian cancer. Patients are most often diagnosed with metastatic (Stage III) disease, at which point 5-year survival is <30%. Despite extensive testing of targeted therapies in preclinical and clinical trials, there have been no new treatments that lengthen survival of ovarian cancer patients in more than 40 years. Standard treatment continues to be surgical de-bulking and platinum-based chemotherapy.

A need remains for antibodies and binding fragments that bind FGL2 with high affinity and specificity. In particular, a need remains for anti-FGL2 antibodies and binding fragments useful for treating cancer such as ovarian cancer.

SUMMARY

The present disclosure describes highly specific monoclonal antibodies to FGL2 (referred to herein as 9D8, 3H9 and 2A5). Antibody 9D8 reduces tumor weight in a murine model of ovarian cancer.

Accordingly, the disclosure provides an antibody or binding fragment thereof that specifically binds FGL2 comprising:

a light chain variable region and a heavy chain variable region, the heavy chain variable region comprising complementarity determining regions CDR-H1, CDR-H2 and CDR-H3 and the light chain variable region comprising complementarity determining regions CDR-L1, CDR-L2 and CDR-L3, wherein (a) (i) CDR-H1 comprises the amino acid sequence set out in SEQ ID No: 3, and/or CDR-H2 comprises the amino acid sequence set out in SEQ ID No: 5; and/or CDR-H3 comprises the amino acid sequence set out in SEQ ID No: 7; and (ii) CDR-L1 comprises the amino acid sequence set out in SEQ ID No: 12, and/or CDR-L2 comprises the amino acid sequence set out in SEQ ID No: 14; and/or CDR-L3 comprises the amino acid sequence set out in SEQ ID No: 16;

(b) (i) CDR-H1 comprises the amino acid sequence set out in SEQ ID No: 45, and/or CDR-H2 comprises the amino acid sequence set out in SEQ ID No: 47; and/or CDR-H3 comprises the amino acid sequence set out in SEQ ID No: 49; and (ii) CDR-L1 comprises the amino acid sequence set out in SEQ ID No: 54, and/or CDR-L2 comprises the amino acid sequence set out in SEQ ID No: 56; and/or CDR-L3 comprises the amino acid sequence set out in SEQ ID No: 58; or (c) (i) CDR-H1 comprises the amino acid sequence set out in SEQ ID No: 87, and/or CDR-H2 comprises the amino acid sequence set out in SEQ ID No: 89; and/or CDR-H3 comprises the amino acid sequence set out in SEQ ID No: 91; and (ii) CDR-L1 comprises the amino acid sequence set out in SEQ ID No: 96, and/or CDR-L2 comprises the amino acid sequence set out in SEQ ID No: 98; and/or CDR-L3 comprises the amino acid sequence set out in SEQ ID No: 100.

In one embodiment, (a) (i) CDR-H1 comprises the amino acid sequence set out in SEQ ID No: 3, CDR-H2 comprises the amino acid sequence set out in SEQ ID No: 5; and CDR-H3 comprises the amino acid sequence set out in SEQ ID No: 7; and (ii) CDR-L1 comprises the amino acid sequence set out in SEQ ID No: 12, CDR-L2 comprises the amino acid sequence set out in SEQ ID No: 14; and CDR-L3 comprises the amino acid sequence set out in SEQ ID No: 16;

(b) (i) CDR-H1 comprises the amino acid sequence set out in SEQ ID No: 45, CDR-H2 comprises the amino acid sequence set out in SEQ ID No: 47; and CDR-H3 comprises the amino acid sequence set out in SEQ ID No: 49; and (ii) CDR-L1 comprises the amino acid sequence set out in SEQ ID No: 54, CDR-L2 comprises the amino acid sequence set out in SEQ ID No: 56; and CDR-L3 comprises the amino acid sequence set out in SEQ ID No: 58; or (c) (i) CDR-H1 comprises the amino acid sequence set out in SEQ ID No: 87, CDR-H2 comprises the amino acid sequence set out in SEQ ID No: 89; and CDR-H3 comprises the amino acid sequence set out in SEQ ID No: 91; and (ii) CDR-L1 comprises the amino acid sequence set out in SEQ ID No: 96, CDR-L2 comprises the amino acid sequence set out in SEQ ID No: 98; dCDR-L3 comprises the amino acid sequence set out in SEQ ID No: 100.

The disclosure also provides an antibody or binding fragment thereof that specifically binds FGL2 comprising:

a light chain variable region and a heavy chain variable region, the heavy chain variable region comprising complementarity determining regions CDR-H1, CDR-H2 and CDR-H3 and the light chain variable region comprising complementarity determining regions CDR-L1, CDR-L2 and CDR-L3, wherein (a) (i) CDR-H1 is encoded by the nucleic acid sequence of SEQ ID No: 21, and/or CDR-H2 is encoded by the nucleic acid sequence of SEQ ID No: 23; and/or CDR-H3 is encoded by the nucleic acid sequence of SEQ ID No: 25; and (ii) CDR-L1 is encoded by the nucleic acid sequence of SEQ ID No: 30, and/or CDR-L2 is encoded by the nucleic acid sequence of SEQ ID No: 32; and/or CDR-L3 is encoded by the nucleic acid sequence of SEQ ID No: 34;

(b) (i) CDR-H1 is encoded by the nucleic acid sequence of SEQ ID No: 63, and/or CDR-H2 is encoded by the nucleic acid sequence of SEQ ID No: 65; and/or CDR-H3 is encoded by the nucleic acid sequence of SEQ ID No: 67; and (ii) CDR-L1 is encoded by the nucleic acid sequence of SEQ ID No: 72, and/or CDR-L2 is encoded by the nucleic acid sequence of SEQ ID No: 74; and/or CDR-L3 is encoded by the nucleic acid sequence of SEQ ID No: 76; or (c) (i) CDR-H1 is encoded by the nucleic acid sequence of SEQ ID No: 105, and/or CDR-H2 is encoded by the nucleic acid sequence of SEQ ID No: 107; and/or CDR-H3 is encoded by the nucleic acid sequence of SEQ ID No: 109; and (ii) CDR-L1 is encoded by the nucleic acid sequence of SEQ ID No: 114, and/or CDR-L2 is encoded by the nucleic acid sequence of SEQ ID No: 116; and/or CDR-L3 is encoded by the nucleic acid sequence of SEQ ID No: 118.

In one embodiment, (a) (i) CDR-H1 is encoded by the nucleic acid sequence of SEQ ID No: 21, and/or CDR-H2 is encoded by the nucleic acid sequence of SEQ ID No: 23; and CDR-H3 is encoded by the nucleic acid sequence of SEQ ID No: 25; and (ii) CDR-L1 is encoded by the nucleic acid sequence of SEQ ID No: 30, and/or CDR-L2 is encoded by the nucleic acid sequence of SEQ ID No: 32; and CDR-L3 is encoded by the nucleic acid sequence of SEQ ID No: 34;

(b) (i) CDR-H1 is encoded by the nucleic acid sequence of SEQ ID No: 63, and/or CDR-H2 is encoded by the nucleic acid sequence of SEQ ID No: 65; and CDR-H3 is encoded by the nucleic acid sequence of SEQ ID No: 67; and (ii) CDR-L1 is encoded by the nucleic acid sequence of SEQ ID No: 72, and/or CDR-L2 is encoded by the nucleic acid sequence of SEQ ID No: 74; and CDR-L3 is encoded by the nucleic acid sequence of SEQ ID No: 76; or (c) (i) CDR-H1 is encoded by the nucleic acid sequence of SEQ ID No: 105, and/or CDR-H2 is encoded by the nucleic acid sequence of SEQ ID No: 107; and CDR-H3 is encoded by the nucleic acid sequence of SEQ ID No: 109; and (ii) CDR-L1 is encoded by the nucleic acid sequence of SEQ ID No: 114, and/or CDR-L2 is encoded by the nucleic acid sequence of SEQ ID No: 116; and CDR-L3 is encoded by the nucleic acid sequence of SEQ ID No: 118.

In another embodiment, the heavy chain variable region comprises the amino acid sequence of SEQ ID NO: 38 or an amino acid sequence having at least 70% sequence identity to the framework regions of SEQ ID NO: 38 and/or the light chain variable region comprises the amino acid sequence of SEQ ID NO: 40 or an amino acid sequence having at least 70% sequence identity to the framework regions of SEQ ID NO: 40.

In another embodiment, the heavy chain variable region comprises the amino acid sequence of SEQ ID NO: 80 or an amino acid sequence having at least 70% sequence identity to the framework regions of SEQ ID NO: 80 and/or the light chain variable region comprises the amino acid sequence of SEQ ID NO: 82 or an amino acid sequence having at least 70% sequence identity to the framework regions of SEQ ID NO: 82.

In another embodiment, the heavy chain variable region comprises the amino acid sequence of SEQ ID NO: 122 or an amino acid sequence having at least 70% sequence identity to the framework regions of SEQ ID NO: 122 and/or the light chain variable region comprises the amino acid sequence of SEQ ID NO: 124 or an amino acid sequence having at least 70% sequence identity to the framework regions of SEQ ID NO: 124.

In another embodiment, the FGL2 is human FGL2.

In another embodiment, the antibody is a monoclonal antibody.

In another embodiment, the binding fragment is selected from the group consisting of a fragment antigen-binding Fab, a single-chain Fv (scFv), a (svFv)2, a scFv-CH3, a scFv-Fc, a bispecific antibody, a phage-Fab and a phage-scFv.

In another embodiment, antibody or antigen-binding fragment is an IgG molecule.

The disclosure also provides an antibody or binding fragment thereof that competes with the antibody or binding fragment described above.

The disclosure also provides an immunoconjugate comprising (1) the antibody or binding fragment described above attached to (2) an effector agent.

In one embodiment, the effector agent is a detection agent, an anti-neoplastic agent or a toxin.

The disclosure also provides a composition comprising an antibody or binding fragment or the immunoconjugate described above and a carrier.

The disclosure also provides a method of detecting a FGL2-expressing cell, the method comprising:

a) contacting a cell with
   (i) an antibody or binding fragment described above,
   (ii) an immunoconjugate described above or
   (iii) a composition described above, under conditions to form an antibody:FGL2 complex; and b) detecting the antibody:FGL2 complex.

The disclosure further provides a method for screening, for diagnosing or for detecting a FGL2-expressing cancer, the method comprising:

(a) contacting a sample from a subject using
   (i) an antibody or binding fragment described above,
   (ii) an immunoconjugate described above or
   (iii) a composition described above, under conditions to form an antibody:FGL2 complex; and (b) comparing the level of FGL2 in the sample with a control, wherein an increased level of FGL2 in the sample compared to the control is indicative that the subject has a FGL2-expressing cancer.

In one embodiment, the FGL2-expressing cancer is ovarian cancer.

The disclosure also provides a method of treating cancer comprising administering an effective amount of:

(i) an antibody or binding fragment described above,
(ii) an immunoconjugate described above or
(iii) a composition described above,
to a subject in need thereof.

In one embodiment, the cancer is a FGL2-expressing cancer.

In another embodiment the cancer is ovarian cancer, optionally high-grade serous ovarian cancer, undifferentiated ovarian cancer, granulosa cell ovarian cancer, endometrioid ovarian cancer, serous ovarian cancer, secondary ovarian cancer (another primary) or clear cell ovarian cancer.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIG. 1 shows alterations in FGL2, gene mutations, deletions and amplifications in cancer.

FIG. 2 shows development of murine recombinant FGL2. Native mouse FGL2 exists as an oligomer. Recombinant 6×HIS tagged mouse FGL2 was produced in COS-7 cells. Purified FGL2 was analyzed by 10% SDS-PAGE, Coomassie blue staining (left) and Western blot with mouse anti-HIS antibody conjugated with horseradish peroxidase (HRP) (right) under either reducing (R) or non-reducing (NR) conditions. 1 g of purified FGL2 was loaded in each lane of the SDS-PAGE and 150 ng of FGL2 was loaded in each lane of the Western blot. Protein ladders: Fermentas #SM0671 and Invitrogen #LC5699.

FIG. 3 shows quality control for purity and functionality of recombinant FGL2. 9D8 antibody was purified from ascites fluid. Purified 9D8 was subject to gel electrophoresis under reducing conditions and stained by coomassie blue staining and in a western blot using anti-mouse IgG heavy chain antibody (left). The purified 9D8 product was used as a capture antibody in an ELISA to demonstrate the capacity for 9D8 to bind recombinant FGL2 (right).

FIG. 4 shows selectivity of 9D8 for FGL2. A) Images of antigen microarrays. Array features were spotted in duplicate and are approximately 500 um in diameter. The array on the left was only probed with secondary antibodies, whereas the array on the right was also probed with 9D8. Identity of the array features are indicated by the legend. B) Quantification of IgG reactivity on the arrays. In addition to hFGL2, 9D8 also had reactivity against a human coronary artery endothelial cell (HCAEC) lysate. 9D8 did not react against other antigens including fibrinogen, heat shock proteins and nuclear proteins. MFI; median fluorescence intensity.

FIG. 5 shows binding of recombinant human and mouse FGL2 to 9D8 using surface plasmon resonance (SPR). The response difference (Resp. Diff.) for each experiment was plotted against time (s). Resp. Diff. is the ligand-immobilized flow cell minus the control flow cell. A) Human FGL2. For the full kinetic analysis, SPR was performed using 0.625 nM, 2.5 nM, 5 nM, and 10 nM recombinant human FGL2. B) Mouse FGL2. For this analysis, SPR was performed using 10 nM recombinant mouse FGL2.

Figure 16:
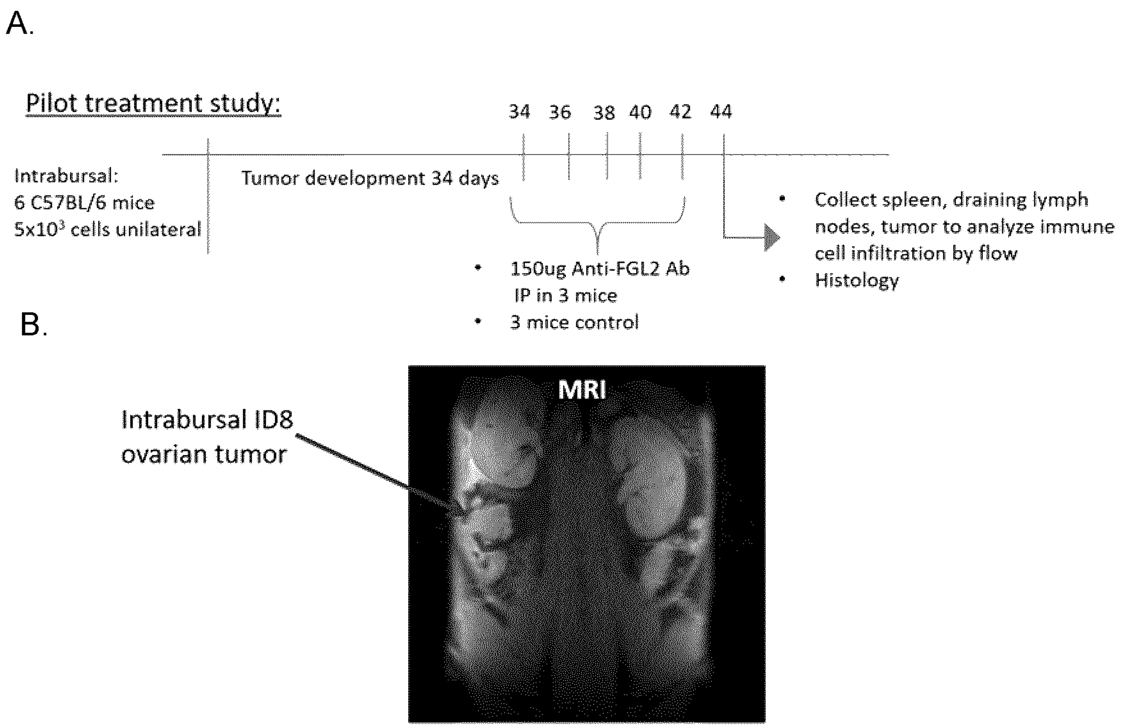

FIG. 16 shows an outline of the study testing anti-FGL2 antibody therapy in the syngeneic ID8 murine ovarian cancer model. A) shows a timeline for the study testing anti-FGL2 antibodies in 3 mice with intrabursal ID8 tumors vs. 3 control (untreated) mice. B) shows the ability of MRI to visualize the primary ID8 tumor.

Figure 17:
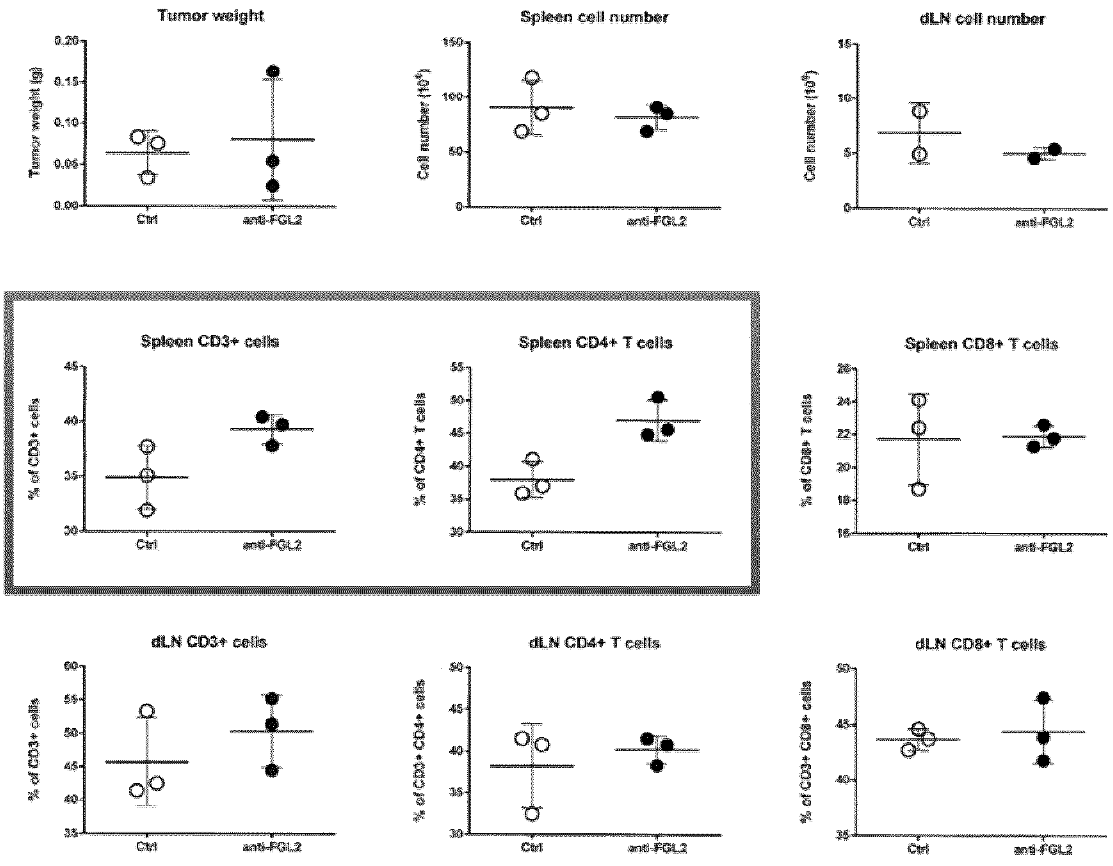

FIG. 17 shows an increase in splenic CD3+CD4+ T cells in mice treated with anti-FGL2 antibody. Analysis of tumor weight, spleen and draining lymph node (dLN) cells by flow cytometry. Tumor weight was reduced in 2/3 treated mice.

Figure 18:
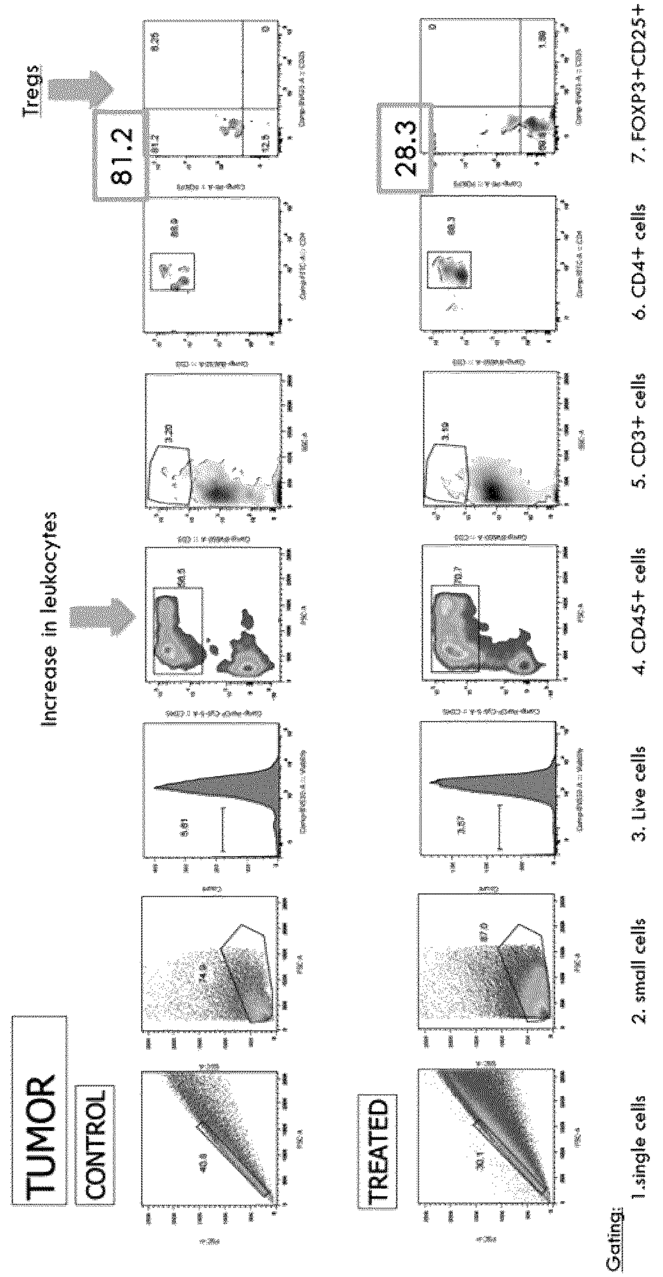

FIG. 18 is an analysis of tumors showing that anti-FGL2 treatment increases leukocytes in the tumor, and reduces FOXP3+CD25+ cells (Tregs). 9D8 increases total leukocytes and reduces Tregs within the tumor.

Figure 19:
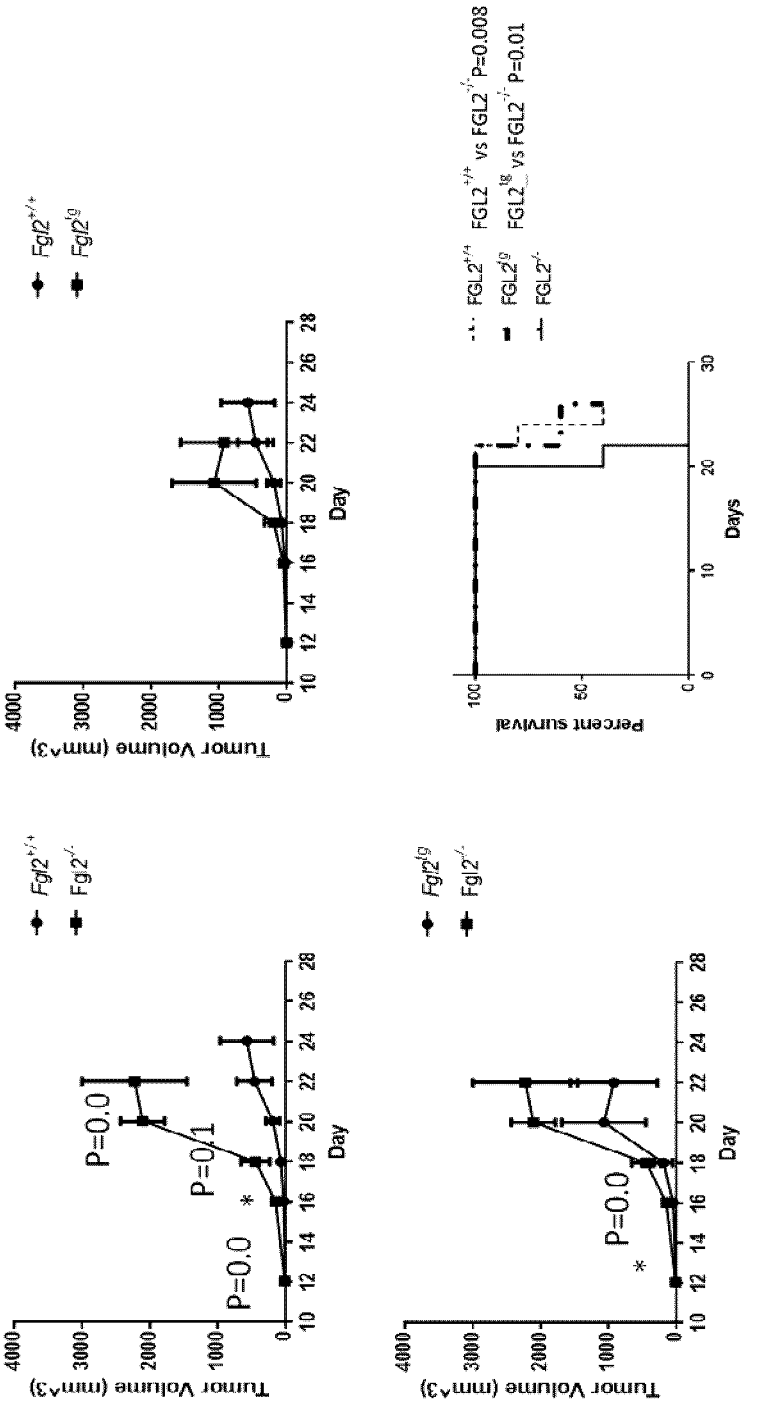

FIG. 19 shows that FGL2−/− mice have impaired tumor control and decreased survival following subcutaneous injection of 104 B16 melanoma cells. Fgl2$^{+/+}$, Fgl2$^{−/−}$ and Fgl2$^{tg}$ were subcutaneously injected with $10^4$ of B16 melanoma cells and tumor growth and survival was monitored.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further, the definitions and embodiments described in particular sections are intended to be applicable to other embodiments herein described for which they are suitable as would be understood by a person skilled in the art. For example, in the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Antibody and/or Binding Fragment Thereof:

The present disclosure provides antibodies and binding fragments thereof which specifically bind FGL2.

The term "FGL2" or "FGL2/fibroleukin" refers to the fibrinogen-like protein 2 and includes all known and naturally occurring FGL2 molecules including full length FGL2 protein, fragments thereof, as well as nucleic acids encoding said protein and fragments, as determinable from the context used. FGL2 includes, but is not limited to, mammalian FGL2 such as human FGL2, or rodent FGL2 including for example mouse and rat FGL2. FGL2 is encoded by the fgl2 gene, which has been localized to chromosome 7 and 5 in humans and mice respectively, is composed of two exons that are separated by one intron. The fgl2 gene encodes a protein of 432 amino acids in mice and 439 amino acids in humans (28-30). Based on sequence and structural analysis, it is predicted that the encoded protein is composed of two major domains, the N-terminal domain and the carboxyl-terminus, and is a tetrameric complex. The N-terminal domain is proposed to have a linear conformation due to the presence of α-helical region and several conserved cysteine residues, which can promote a coiled-coil formation. The 229-amino-acid-long carboxyl-terminus consists of a highly conserved globular domain, known as the fibrinogen-related domain (FRED) that is characteristic of the fibrinogen-related protein superfamily. The overall identity between mouse and human FGL2 is 78%, but within the FRED domain the two proteins share 90% sequence identity.

As used herein, an antibody or binding fragment which "specifically binds FGL2" is an agent which binds FGL2, for example FGL2-expressing cells as opposed to cells not expressing FGL2 (as determined, e.g. via flow cytometric analysis) or expressing minimal FGL2. For example, an antibody or binding fragment that specifically binds FGL2 is one that is capable of binding FGL2 with a $K_D$ of $10^{-5}$ M (10000 nM) or less, e.g., $10^{-6}$, $10^{-7}$, $10^{-8}$, $10^{-9}$, $10^{-10}$, $10^{-11}$, $10^{-12}$ or less. The term "anti-FGL2" antibody or binding fragment is also used herein for the same purpose.

As used herein, and unless otherwise specified, the term "antibody" refers to an immunoglobulin (Ig) molecule. The antibody may be from recombinant sources and/or produced in transgenic animals. The basic antibody structural unit is known to comprise a tetramer. Each tetramer is composed of two identical pairs of polypeptide chains, each pair having one light ("L") (about 25 kDa) and one heavy ("H") chain (about 50-70 kDa). The amino-terminal portion of each chain includes a variable region of about 100 to 110 or more amino acids primarily responsible for antigen recognition, and described in more detail below. The carboxy-terminal portion of each chain defines a constant region primarily responsible for effector function. The term "antigen-binding site" or "binding portion" refers to the part of the binding protein that participates in antigen binding. In an antibody, the antigen binding site is formed by amino acid residues of the N-terminal variable ("V") regions of the heavy and light chains. Three highly divergent stretches within the V regions of the heavy and light chains, referred to as "hypervariable regions". In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs". Accordingly, the antibody in an embodiment comprises a heavy chain variable region or a heavy chain comprising a heavy chain complementarity determining region 1 (CDR-H1), heavy chain complementarity determining region 2 (CDR-H2) and heavy chain complementarity determining region 3 (CDR-H3), as well as a light chain variable region or light chain comprising a light chain complementarity determining region 1 (CDR-L1), light chain complementarity determining region 2 (CDR-L2) and light chain complementarity determining region 3 (CDR-L3). The CDRs are interposed between more conserved flanking stretches known as "framework regions", or "FRs". Thus, the term "FR" refers to amino acid sequences which are naturally found between, and adjacent to, hypervariable regions in immunoglobulins.

CDRs and framework regions (FRs) disclosed herein, amino acid sequences of CDRs and FRs disclosed herein, and CDR-encoding or FR-encoding nucleic acid sequences disclosed herein, can be defined in accordance with the Kabat numbering system (Kabat et al., 1991). Another system alternately employed in the art for such definitions is IMGT numbering (Lefranc et al., 2003).

In particular, the present disclosure provides an anti-FGL2 antibody termed "9D8" having the amino acid and nucleic acid sequences set out in Table 2.

Accordingly, in one embodiment, the present disclosure provides an antibody or binding fragment thereof comprising:

(a) a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 3, and/or CDR-H2 comprises or consists of the amino acid sequence set out in SEQ ID No: 5; and/or CDR-H3 comprises or consists of the amino acid sequence set out in SEQ ID No: 7; and (ii) CDR-L1 comprises or consists of the amino acid sequence set out in SEQ ID No: 12, and/or CDR-L2 comprises or consists of the amino acid sequence set out in SEQ ID No: 14; and/or CDR-L3 comprises or consists of the amino acid sequence set out in SEQ ID No: 16.

In another embodiment, an antibody or binding fragment thereof is provided comprising a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 3, CDR-H2 comprises or consists of the amino acid sequence set out in SEQ ID No: 5; and CDR-H3 comprises or consists of the amino acid sequence set out in SEQ ID No: 7; and (ii) CDR-L1 comprises or consists of the amino acid sequence set out in SEQ ID No: 12, CDR-L2 comprises or consists of the amino acid sequence set out in SEQ ID No: 14; and CDR-L3 comprises or consists of the amino acid sequence set out in SEQ ID No: 16.

In another embodiment, the heavy chain variable region comprises the amino acid sequence set forth in SEQ ID NO: 38, or an amino acid sequence having at least 70%, 75%, 80%, 85%, 90%, 95% or 99% sequence identity to SEQ ID NO: 38 or the framework regions of SEQ ID NO: 38. In one embodiment, the framework regions of SEQ ID NO: 38 comprise or consist of SEQ ID Nos: 2, 4, 6 and 8.

In another embodiment, the heavy chain variable region consists of the amino acid sequence set forth in SEQ ID NO: 38.

In another embodiment, the light chain variable region comprises the amino acid sequence set forth in SEQ ID NO: 40.

or an amino acid sequence having at least 70%, 75%, 80%, 85%, 90%, 95% or 99% sequence identity to SEQ ID NO: 40 or the framework regions of SEQ ID NO: 40. In one embodiment, the framework regions of SEQ ID NO: 40 comprise or consist of SEQ ID Nos: 11, 13, 15 and 17.

In another embodiment, the light chain variable region consists of the amino acid sequence set forth in SEQ ID NO: 40.

In another embodiment, the heavy variable region comprises the amino acid sequence of SEQ ID NO: 38 or an amino acid sequence having at least 70%, 75%, 80%, 85%, 90%, 95% or 99% sequence identity to the framework regions of SEQ ID NO: 38, and/or the light variable region comprises the amino acid sequence of SEQ ID NO: 40 or an amino acid sequence having at least 70%, 75%, 80%, 85%, 90%, 95% or 99% sequence identity to the framework regions of SEQ ID NO: 40.

The present disclosure also provides an anti-FGL2 antibody termed "3H9" having the amino acid and nucleic acid sequences set out in Table 3.

Accordingly, in one embodiment, the present disclosure provides an antibody or binding fragment thereof comprising:

(a) a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 45, and/or CDR-H2 comprises or consists of the amino acid sequence set out in SEQ ID No: 47; and/or CDR-H3 comprises or consists of the amino acid sequence set out in SEQ ID No: 49; and (ii) CDR-L1 comprises or consists of the amino acid sequence set out in SEQ ID No: 54, and/or CDR-L2 comprises or consists of the amino acid sequence set out in SEQ ID No: 56; and/or CDR-L3 comprises or consists of the amino acid sequence set out in SEQ ID No: 58.

In another embodiment, an antibody or binding fragment thereof is provided comprising a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 45, CDR-H2 comprises or consists of the amino acid sequence set out in SEQ ID No: 47; and CDR-H3 comprises or consists of the amino acid sequence set out in SEQ ID No: 49; and (ii) CDR-L1 comprises or consists of the amino acid sequence set out in SEQ ID No: 54, CDR-L2 comprises or consists of the amino acid sequence set out in SEQ ID No: 56; and CDR-L3 comprises or consists of the amino acid sequence set out in SEQ ID No: 58.

In another embodiment, the heavy chain variable region comprises the amino acid sequence set forth in SEQ ID NO: 80, or an amino acid sequence having at least 70%, 75%, 80%, 85%, 90%, 95% or 99% sequence identity to SEQ ID NO: 80 or the framework regions of SEQ ID NO: 82. In one embodiment, the framework regions of SEQ ID NO: 80 comprise or consist of SEQ ID Nos: 44, 46, 48 and 50.

In another embodiment, the heavy chain variable region consists of the amino acid sequence set forth in SEQ ID NO: 80.

In another embodiment, the light chain variable region comprises the amino acid sequence set forth in SEQ ID NO: 82.

or an amino acid sequence having at least 70%, 75%, 80%, 85%, 90%, 95% or 99% sequence identity to SEQ ID NO: 82 or the framework regions of SEQ ID NO: 82. In one embodiment, the framework regions of SEQ ID NO: 82 comprise or consist of SEQ ID Nos: 53, 55, 57 and 59.

In another embodiment, the light chain variable region consists of the amino acid sequence set forth in SEQ ID NO: 82.

In another embodiment, the heavy variable region comprises the amino acid sequence of SEQ ID NO: 80 or an amino acid sequence having at least 70%, 75%, 80%, 85%, 90%, 95% or 99% sequence identity to the framework regions of SEQ ID NO: 80, and/or the light variable region comprises the amino acid sequence of SEQ ID NO: 82 or an amino acid sequence having at least 70%, 75%, 80%, 85%, 90%, 95% or 99% sequence identity to the framework regions of SEQ ID NO: 82.

The present disclosure also provides an anti-FGL2 antibody termed "2A5" having the amino acid and nucleic acid sequences set out in Table 4.

Accordingly, in one embodiment, the present disclosure provides an antibody or binding fragment thereof comprising:

(a) a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 87, and/or CDR-H2 comprises or consists of the amino acid sequence set out in SEQ ID No: 89; and/or CDR-H3 comprises or consists of the amino acid sequence set out in SEQ ID No: 91; and (ii) CDR-L1 comprises or consists of the amino acid sequence set out in SEQ ID No: 96, and/or CDR-L2 comprises or consists of the amino acid sequence set out in SEQ ID No: 98; and/or CDR-L3 comprises or consists of the amino acid sequence set out in SEQ ID No: 100.

In another embodiment, an antibody or binding fragment thereof is provided comprising a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein (i) CDR-H1 comprises or consists of the amino acid sequence set out in SEQ ID No: 87, CDR-H2 comprises or consists of the amino acid sequence set out in SEQ ID No: 89; and CDR-H3 comprises or consists of the amino acid sequence set out in SEQ ID No: 91; and (ii) CDR-L1 comprises or consists of the amino acid sequence set out in SEQ ID No: 96, CDR-L2 comprises or consists of the amino acid sequence set out in SEQ ID No: 98; and CDR-L3 comprises or consists of the amino acid sequence set out in SEQ ID No: 100.

In another embodiment, the heavy chain variable region comprises the amino acid sequence set forth in SEQ ID NO: 122, or an amino acid sequence having at least 70%, 75%, 80%, 85%, 90%, 95% or 99% sequence identity to SEQ ID NO: 122 or the framework regions of SEQ ID NO: 122. In one embodiment, the framework regions of SEQ ID NO: 122 comprise or consist of SEQ ID Nos: 86, 88, 90 and 92.

In another embodiment, the heavy chain variable region consists of the amino acid sequence set forth in SEQ ID NO: 122.

In another embodiment, the light chain variable region comprises the amino acid sequence set forth in SEQ ID NO: 124.
or an amino acid sequence having at least 70%, 75%, 80%, 85%, 90%, 95% or 99% sequence identity to SEQ ID NO: 124 or the framework regions of SEQ ID NO: 124. In one embodiment, the framework regions of SEQ ID NO: 124 comprise or consist of SEQ ID Nos: 95, 97, 99 and 101.

In another embodiment, the light chain variable region consists of the amino acid sequence set forth in SEQ ID NO: 124.

In another embodiment, the heavy variable region comprises the amino acid sequence of SEQ ID NO: 122 or an amino acid sequence having at least 70%, 75%, 80%, 85%, 90%, 95% or 99% sequence identity to the framework regions of SEQ ID NO: 122, and/or the light variable region comprises the amino acid sequence of SEQ ID NO: 124 or an amino acid sequence having at least 70%, 75%, 80%, 85%, 90%, 95% or 99% sequence identity to the framework regions of SEQ ID NO: 124.

For antibodies, percentage sequence identities can be determined when antibody sequences maximally aligned by IMGT or Kabat or other numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

As used herein, the term "epitope" refers to the specific site or specific combination of sites/amino acids on an antigen that are bound by an antibody for example an antibody or binding fragment described herein.

The present disclosure also provides an antibody or binding fragment that competes with an antibody or binding fragment as described herein for binding to FGL2. Various methods are known in the art for determining if two antibodies and/or binding fragments compete for binding to the same antigen. For example, if the antibody or binding fragment being tested competes with the anti-FGL2 antibody or binding fragment, a decrease in binding to FGL2 by the anti-FGL2 antibody or binding fragment is seen. Methods for the testing binding to antigens include, but are not limited to, enzyme linked immunosorbent assay (ELISA) and other immunologically mediated techniques known within the art.

In one embodiment, the "antibody or binding fragment" is selected from a fragment antigen-binding (Fab), single-chain Fv (scFv), single-chain Fab (scFab), Fab', Fv, chemically linked $F(ab')_2$, dsFv, dsFv', $sc(Fv)_2$, ds-scFv, $(dsFv)_2$, scFv-Fc, scFV-$C_H3$, single-chain immunoglobulin (e.g. scIgG), single-domain antibody (sdAb, nanobody), scFv-Fc, minibody (scFv-$C_H3$), diabody, tribody, tetrabody, multimeric antibody (e.g. scFv dimer, bivalent diabody), multispecific antibody (e.g. bispecific antibody, trispecific antibody, di-scFv, tri-scFv, bispecific $Fab_2$, trispecific $Fab_2$, trispecific triabody, trispecific $Fab_3$), multimeric/multispecific antibody (e.g. scFv dimer, bispecific diabody, dsFv-dsFv'), heavy-chain antibody, $Fab_3$, divalent VHH, pentavalent VHH (pentabody), $(scFv\text{-}SA)_4$ or $[sc(Fv)2]_2$.

Fab, Fab' and F(ab')2, scFv, dsFv, ds-scFv, dimers, minibodies, diabodies, bispecific antibody fragments and other fragments can be synthesized by recombinant techniques.

Antibodies can also be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments.

In one embodiment, the antibody or binding fragment is an antibody, such as a human antibody, containing engineered variable regions (e.g. containing variable regions selected from a phage display library displaying engineered antibody variable regions, e.g. a phage-Fab library or a phage-scFv library), or a chimeric antibody comprising human constant regions and an antibody variable region of a non-human mammal. The antibody or binding fragment may be a humanized antibody, e.g. an antibody comprising human constant regions, human variable region framework regions, and FGL2-binding CDRs generated in a non-human mammal. The non-human mammal may be a rodent, such as a mouse, rat, rabbit, guinea pig or hamster. Alternately, the non-human mammal may be an ungulate, such as a camelid or a bovid.

In another embodiment, the antibody or binding fragment is a human antibody, such as an IgG1 antibody, wherein the heavy chain constant regions are gamma1 heavy chain constant regions. In other embodiments, the antibody or binding fragment is a human antibody, such as an IgA1, IgA2, IgD, IgG2, IgG3, IgG4, IgE or IgM antibody, wherein the heavy chain constant regions are alpha1, alpha2, delta, gamma2, gamma3, gamma4, epsilon or mu heavy chain constant regions, respectively.

In a further embodiment, the antibody or binding fragment is a monoclonal antibody. As used herein, a "monoclonal" antibody or binding fragment of the disclosure refers to a population of identical antibodies, for example a population of antibodies where the CDRs are identical in all the molecules of the population. Various procedures known within the art may be used for the production of monoclonal antibodies (see, for example, Greenfield, 2013). Monoclonal antibodies are commonly alternatively referred to using the abbreviations "mAb" or "MAb".

The antibody or binding fragment thereof is optionally an isolated antibody or binding fragment. The term "isolated antibody or binding fragment" or "isolated and purified antibody or binding fragment" refers to an antibody or binding fragment thereof that is substantially free of cellular material or culture medium when produced by recombinant DNA techniques, or chemical precursors, or other chemicals when chemically synthesized and/or other antibodies, for example directed to a different epitope.

Functional variants of the antibodies and binding fragments described herein are also encompassed by the present disclosure. The term "functional variant" as used herein includes one or more amino acid and/or nucleotide modifications in a sequence (polypeptide or nucleic acid respectively) for example, one or more modifications of a light chain or a heavy chain complementarity determining region (CDR) disclosed herein that perform substantially the same function as the light chain and heavy chain CDRs disclosed herein in substantially the same way. For instance, variants of the CDRs disclosed herein have the same function of being able to specifically bind to the same epitope on FGL2 as 9D8, 3H9 or 2A5. In one embodiment, variants of CDRs disclosed herein include, without limitation, conservative amino acid substitutions. Variants of the CDRs also include additions and deletions to the CDR sequences disclosed herein. In addition, variant nucleotide sequences and polypeptide sequences include analogs and derivatives thereof.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitutions include:

Conservative Substitutions

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Thus, in one embodiment, the present disclosure includes functional variants to the amino acid sequences disclosed herein.

In particular, the disclosure provides functional variants of the CDR sequences disclosed herein. In one embodiment, functional variants of the CDR sequences of the light and heavy chains disclosed herein have at least 70%, 75%, 80%, 85%, 90%, 95% or 99% sequence identity with the CDR sequences disclosed herein. In another embodiment, functional variants of the CDR sequences disclosed herein comprise at least 1, 2, 3 or 4 amino acid substitutions, optionally conservative substitutions, in the CDR sequences disclosed herein.

The disclosure also provides functional variants of the amino acid sequences of the heavy chain and light chain variable regions of 9D8. In one embodiment, the variant amino acid sequences of the amino acid sequences disclosed herein comprise sequences having at least 70%, 75%, 80%, 85%, 90%, 95% or 99% sequence identity to SEQ ID NOS: 38 or 40 or sequences having at least 70%, 75%, 80%, 85%, 90%, 95% or 99% to the framework regions of SEQ ID NOS: 38 or 40.

The disclosure further provides functional variants of the amino acid sequences of the heavy chain and light chain variable regions of 3H9. In one embodiment, the variant amino acid sequences of the amino acid sequences disclosed herein comprise sequences having at least 70%, 75%, 80%, 85%, 90%, 95% or 99% sequence identity to SEQ ID NOS: 80 or 82 or sequences having at least 70%, 75%, 80%, 85%, 90%, 95% or 99% to the framework regions of SEQ ID NOS: 80 or 82.

The disclosure further provides functional variants of the amino acid sequences of the heavy chain and light chain variable regions of 2A5. In one embodiment, the variant amino acid sequences of the amino acid sequences disclosed herein comprise sequences having at least 70%, 75%, 80%, 85%, 90%, 95% or 99% sequence identity to SEQ ID NOS: 122 or 124 or sequences having at least 70%, 75%, 80%, 85%, 90%, 95% or 99% to the framework regions of SEQ ID NOS: 122 or 124.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package.

When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Also provided in the present disclosure are nucleic acids encoding the antibodies, binding fragments, variable regions and CDRs described herein, and functional variants thereof. As used herein, the term "nucleic acids" includes isolated nucleic acids as well as single stranded nucleic acid sequences, double stranded nucleic acid sequences and cDNA.

In particular the present disclosure provides nucleic acids encoding the CDR regions of disclosure herein, and functional variants thereof; and nucleic acids encoding the amino acid sequences of the light chain and heavy chain variable domain of 9D8, respectively, and functional variants thereof.

Particularly provided are functional variants of the nucleotide sequences encoding the heavy and light variable regions of antibody 9D8 (SEQ ID NO: 38 and SEQ ID NO: 40, respectively) and functional variants of the nucleotide sequences (SEQ ID NO: 21, SEQ ID NO: 23, SEQ ID NO: 25, SEQ ID NO: 30, SEQ ID NO: 32 and SEQ ID NO: 34) encoding the amino acid sequences of the CDRs of antibody 9D8.

The present disclosure also provides nucleic acids encoding the CDR regions of disclosure herein, and functional variants thereof; and nucleic acids encoding the amino acid sequences of the light chain and heavy chain variable domain of 3H9, respectively, and functional variants thereof.

Particularly provided are functional variants of the nucleotide sequences encoding the heavy and light variable regions of antibody 3H9 (SEQ ID NO: 80 and SEQ ID NO: 82, respectively) and functional variants of the nucleotide sequences (SEQ ID NO: 63, SEQ ID NO: 65, SEQ ID NO: 67, SEQ ID NO: 72, SEQ ID NO: 74 and SEQ ID NO: 76) encoding the amino acid sequences of the CDRs of antibody 3H9.

The present disclosure also provides nucleic acids encoding the CDR regions of disclosure herein, and functional variants thereof; and nucleic acids encoding the amino acid sequences of the light chain and heavy chain variable domain of 3H9, respectively, and functional variants thereof.

Particularly provided are functional variants of the nucleotide sequences encoding the heavy and light variable regions of antibody 2A5 (SEQ ID NO: 122 and SEQ ID NO: 124, respectively) and functional variants of the nucleotide sequences (SEQ ID NO: 105, SEQ ID NO: 107, SEQ ID NO: 109, SEQ ID NO: 114, SEQ ID NO: 116 and SEQ ID NO: 118) encoding the amino acid sequences of the CDRs of antibody 2A5.

In addition, the functional variants include nucleotide sequences that hybridize to the nucleic acids encoding the amino acid sequences of the present disclosure, or the complement thereof, under at least moderately stringent hybridization conditions.

In another embodiment, the variant nucleic acid sequences disclosed herein comprise sequences having at least 50%, or at least 60%, or at least 70%, or at least 80%, or at least 90%, or at least 95% sequence identity to the nucleic acid sequences disclosed herein.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

Antibodies and binding fragments disclosed herein can be expressed by a vector containing a nucleic acid encoding the polypeptide of interest using methods which are well known and routinely practiced in the art. Accordingly, the present disclosure also provides a vector expressing any of the nucleic acids described herein.

The antibodies and binding fragments can be prepared by constructing a nucleic acid encoding an antibody or binding fragment, inserting the construct into an expression vector, and then expressing it in appropriate host cells. Vectors useful for expressing the antibodies and binding fragments disclosed herein are well known in the art. In one embodiment, the vector includes suitable translation initiation and termination signals in operable reading phase with a functional promoter and can comprise one or more phenotypic selectable markers and an origin of replication to ensure maintenance of the vector and, if desirable, to provide amplification within the host. In addition to vectors, the nucleic acids of the present disclosure can be delivered to a cell or a subject via any other method known in the art including, but not limited to, liposomes, naked DNA, adjuvant-assisted DNA, gene gun, catheters, etc.

Non-covalent interactions occur between an antibody or binding fragment thereof and an antigen for which the antibody or binding fragment is specific. The strength, or affinity of immunological binding interactions can be expressed in terms of the dissociation constant ($K_D$) of the interaction, wherein a smaller $K_D$ represents a greater affinity. Immunological binding properties of specific polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation (see, e.g. Malmqvist, 1993). The ratio of $K_{off}/K_{on}$ enables the cancellation of all parameters not related to affinity, and is equal to the dissociation constant $K_D$ (see, e.g. Davies et al., 1990).

Using surface plasmon resonance (SPR), the anti-FGL2 antibody 9D8 was shown to bind recombinant human FGL2 with a $K_D$ of $8.57\times10^{-10}$ M and recombinant mouse FGL2 with a $K_D$ of $1.8\times10^{-9}$ M. In addition, the anti-FGL2 antibody 3H9 was shown to bind recombinant human FGL2 with a $K_D$ of $2.86\times10^{-10}$ M and recombinant mouse FGL2 with a $K_D$ of $1.03\times10^{-10}$ M. Accordingly, in one embodiment, an antibody or binding fragment thereof is provided that binds FGL2 with a $K_D$ of ≤100 nM, ≤90 nM, ≤80 nM, ≤70 nM, ≤60 nM, ≤50 nM, ≤40 nM, ≤30 nM, ≤20 nM, ≤10 nM, ≤9 nM, ≤8 nM, ≤7 nM, ≤6 nM, ≤5 nM, ≤4 nM, ≤2 nM, ≤1 nM, ≤0.9 nM or ≤0.8 nM. A report of the binding of 9D8 and 3H9 to recombinant human and mouse FGL2 is shown in Table 1.

TABLE 1

Binding of 9D8 and 3H9 to recombinant human and mouse FGL2

| Ligand | Analyte | ka (1/Ms) | kd (1/s) | Rmax | KD (M) | KA | Conc. | Chi2 |
|---|---|---|---|---|---|---|---|---|
| 9D8 | human FGL2 | $2.22\times10^{6}$ | $1.90\times10^{-3}$ | 33.3 | $8.57\times10^{-10}$ | $1.17\times10^{9}$ | 0<br>0.625<br>2.5<br>5<br>10<br>10 | 0.689 |
| 9D8 | mouse FGL2 | $1.85\times10^{6}$ | $3.34\times10^{-3}$ | 80.9 | $1.80\times10^{-9}$ | $5.56\times10^{8}$ | 0<br>10 | 0.521 |
| 3H9 | human FGL2 | $3.09\times10^{6}$ | $8.84\times10^{-4}$ | 22.9 | $2.86\times10^{-10}$ | $3.50\times10^{9}$ | 50 | 0.113 |
| 3H9 | mouse FGL2 | $1.84\times10^{6}$ | $1.89\times10^{-4}$ | 8.76 | $1.03\times10^{-10}$ | $9.74\times10^{9}$ | 50 | 0.0932 |

Immunoconjugates

The present disclosure also provides an immunoconjugate comprising (1) an antibody or binding fragment thereof that specifically binds FGL2, (2) an effector agent, optionally linked directly or indirectly to the antibody or binding fragment thereof; and (3) optionally a linker linking the antibody or binding fragment thereof and the effector agent.

In one embodiment, the effector agent is a label or a tag, which can generate a detectable signal, directly or indirectly. Examples of labels include radioactive isotopes such as 3H, 14C, 32P, 35S, 123I, 125I, 131I. Other examples of labels include, but are not limited to, peptide tags, enzymes (for example, beta-galactosidase, HRP or alkaline phosphatase), proteins (for example phycoerythrin or biotin/streptavidin), magnetic particles, chromophores, fluorescent molecules, chemiluminescent molecules (or example, fluorescein isothiocyanate, rhodamine or luciferin), imaging agents, metal ions and dyes. One exemplary label is IRDye 800CW. The tag can be a purification tag such as a His-tag, a HA-tag, a GST-tag, biotin or a FLAG-tag.

In another embodiment, the effector agent is a therapeutic agent. Therapeutic agents include, but are not limited to, cancer therapeutic agents (chemotherapeutic)/antineoplastic agents.

In another embodiment, the therapeutic agent is a toxin, for example, a cytotoxin. The toxin may be an enzymatically active toxin of bacterial, fungal, plant, or animal origin, or a fragment thereof. Toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the toxin is ricin or another lymphotoxin.

Radioconjugated antibody or binding fragments of the disclosure, may be employed to bind radionuclides to FGL2-expressing cells, for example to visualize the cells or as a cytotoxic treatment of the cells. A variety of radionuclides are available for the production of radioconjugated antibodies. Examples include 212Bi, 131I, 131In, 90Y, and 186Re.

Conjugation may be accomplished by any chemical reaction that will bind an effector agent and an antibody or binding fragment thereof of the disclosure, so long as these retain their respective activities/characteristics for the intended use thereof. This linkage can include many chemical mechanisms, for instance covalent binding, affinity binding, intercalation, coordinate binding and complexation. In embodiments in which the immunoconjugate includes a linker, the linker may be stable or labile.

Compositions

The disclosure also provides compositions including pharmaceutical compositions comprising an antibody or binding fragment thereof described herein or an immunoconjugate described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The composition can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Methods and Uses

Another aspect of the disclosure is a method for producing antibody and/or binding fragment thereof as disclosed herein.

A person skilled in the art will appreciate that several methods can be used to produce antibodies and/or binding fragments thereof as described herein.

In one embodiment, a nucleic acid encoding an antibody described herein is expressed in a host cell to make the antibody and/or binding fragment thereof. In an embodiment, the method comprises:

(a) expressing in a host cell a nucleic acid encoding an antibody and/or binding fragment thereof herein disclosed;

(b) culturing the host cell to produce the antibody and/or binding fragment thereof; and (c) isolating and/or purifying the antibody and/or binding fragment thereof from the host cell.

In some embodiments, a nucleic acid encoding a single chain antibody is expressed. In other embodiments, multiple nucleic acids are expressed, for example encoding a nucleic acid encoding an antibody light chain and a nucleic acid encoding an antibody heavy chain.

Suitable host cells and vectors are described above. Vectors and nucleic acids encoding an antibody described herein may be introduced into mammalian cells via conventional techniques such as calcium phosphate or calcium chloride co-precipitation, DEAE-dextran mediated transfection, lipofectin and other liposome based transfection agents, electroporation or microinjection.

Nucleic acid encoding an antibody described herein may be directly introduced into mammalian cells using delivery vehicles such as retroviral vectors, adenoviral vectors and DNA virus vectors.

The disclosure also provides uses and methods relating to the antibodies and binding fragments thereof described herein.

Detecting FGL2-Expressing Cells

The antibodies and binding fragments thereof, immunoconjugates and compositions of the present disclosure are useful for detecting cells that express FGL2. As used herein, the term "FGL2 expressing cells" refers to cells that express FGL2 protein. In one embodiment, "FGL2 expressing cells" express a detectable level of FGL2. In another embodiment, "FGL2 expressing cells" secrete at least 5, 10, 15, 20, 25, 50, 75, 100, 150 or 200 ng/ml FGL2 into surrounding fluid (for example ascites or blood).

In one embodiment, the FGL2 is expressed intracellularly. In another embodiment, the FGL2 is expressed on the cell membrane or secrete into surrounding fluid. Accordingly, the disclosure provides a use of the antibodies and binding fragments thereof, immunoconjugates and compositions described herein for targeting, binding and/or detecting FGL2-expressing cells. In one embodiment, the FGL2-expressing cells are cancer cells, including, but not limited to, ovarian cancer cells.

In general, the use of binding agents for detection of analytes, such FGL2 protein is well known in the art and may be achieved through the application of numerous approaches. These methods are generally based upon the detection of a label or marker, such as radioactive, fluorescent, biological and enzymatic tags. Examples of methods include, but are not limited to, Western blotting, enzyme linked immunosorbent assay (ELISA), immunofluorescence, immunohistochemistry and flow cytometry.

In one embodiment, the disclosure provides a method of detecting a FGL2-expressing cell in a sample, the method comprising:

a) contacting the sample with the antibody or binding fragment described herein under conditions to form an antibody:FGL2 complex; and b) detecting the presence of an antibody:FGL2 complex.

In one embodiment, the sample is a patient sample, such as a cancer sample from a cancer patient. Alternately, the sample may be a control sample from a healthy individual. Embodiments of the sample include but are not limited to, a sample of cultured cells, cultured cell supernatant, cell lysate, serum, blood plasma, ascites fluid, biological fluid or biological tissue. In other embodiments, the sample is obtained from a cancer. In certain embodiments, the sample is a biopsy sample.

In an embodiment, the complex is detected directly for example wherein the antibody is labeled with a detectable tag or fusion moiety. In an embodiment, the complex is detected indirectly using a secondary antibody specific for the antibody:FGL2 complex.

In an embodiment, detecting is performed using immunoprecipitation, immunoblot, immunohistochemistry or immunocytochemistry proximity ligation assay (PLA), mass spectroscopy-based techniques and fluorescence-activated cell sorting (FACS), and/or mass spectroscopy-based techniques.

Detecting can be performed using methods that are qualitative or measured using quantitative methods, for example by comparing to a standard or standard curve.

Diagnostic Methods

The antibodies and binding fragments thereof, immunoconjugates and pharmaceutical compositions described herein are also useful in the detection/quantitation of FGL2-expressing cells in patient samples or in control samples of healthy individuals and accordingly may be useful diagnostics. For example, the antibodies and binding fragments thereof, immunoconjugates and pharmaceutical compositions of the disclosure can be used to detect/quantitate total cellular expression of FGL2. As used herein, the term "diagnostics" encompasses screening, stratification, monitoring and the like.

In one embodiment, the antibodies and binding fragments thereof, immunoconjugates and pharmaceutical compositions described herein are used to detect FGL2-expressing cells, optionally cancer cells such as ovarian cancer cells.

For example, the antibodies and binding fragments thereof and immunoconjugates of the disclosure, such as the antibodies and antibody fragments of the disclosure, may be used for practicing any one of various assays, e.g. immunofluorescence, flow cytometry or ELISAs, to detect/quantitate FGL2 levels in a sample.

In one embodiment, the sample is a patient sample, such as a cancer sample from a cancer patient. Alternately, the sample may be a control sample from a healthy individual. Embodiments of the sample include but are not limited to, a sample of cultured cells, cultured cell supernatant, cell lysate, serum, blood plasma, biological fluid or biological tissue. In other embodiments, the sample is obtained from a cancer. In certain embodiments, the sample is a biopsy sample.

In one embodiment, the disclosure provides a method for screening, for diagnosing or for detecting a FGL2-expressing cancer, the method comprising:

(a) measuring the level of FGL2 in a sample from a subject optionally using an antibody or assay herein disclosed; and (b) comparing the level of FGL2 in the sample with a control, wherein an increased level of FGL2 in the sample compared to the control is indicative that the subject has an FGL2-expressing cancer In an embodiment, the control is a control value derived from a group of subjects without an FGL2-expressing cancer e.g. normal controls.

The FGL2-expressing cancer is optionally ovarian cancer.

Treatment of Cancer

The present inventors have shown that antibody 9D8 reduces tumor weight in a murine model of ovarian cancer.

Accordingly, the present disclosure provides a method of using an antibody or binding fragment thereof, pharmaceutical composition or immunoconjugate disclosed herein for treating a cancer, the method comprising administering an effective amount of antibody or binding fragment thereof, pharmaceutical composition or immunoconjugate to an animal or cell in need thereof.

In one embodiment, an effective amount of antibody or binding fragment thereof, pharmaceutical composition or immunoconjugate disclosed herein is used for treating a cancer. In another embodiment, antibody or binding fragment thereof, pharmaceutical composition or immunoconjugate disclosed herein is used in the preparation of a medicament for treating or preventing a cancer.

In one embodiment, the cancer is an FGL2-expressing cancer. As used herein, the term "FGL2-expressing cancer" refers to a cancer with detectable expression of FGL2 protein or FGL2 mRNA. In one embodiment, a "FGL2-expressing cancer" has increased expression of FGL2 protein or FGL2 mRNA compared to a control, for example a non-cancerous cell. The level of expression of FGL2 protein or FGL2 mRNA can indicate the aggressiveness of a cancer, with higher levels of expression indicating a more aggressive cancer. In one embodiment, the FGL2-expressing cancer is ovarian cancer. Various ovarian cancer subtypes are contemplated herein, including, but not limited to high-grade serous ovarian cancer, undifferentiated ovarian cancer, granulosa cell ovarian cancer, endometrioid ovarian cancer, serous ovarian cancer, secondary ovarian cancer (another primary), clear cell ovarian cancer, epithelial tumors, germ cell carcinoma tumors, stromal carcinoma tumors and small cell carcinoma of the ovary. In another embodiment, the cancer is a cancer where FGL2 mRNA has been detected, optionally cervical, pancreatic, uterine, esophageal, melanoma, glioblastoma, head and neck, colorectal, bladder, lung, prostate, sarcoma, breast, liver or renal cancer or acute myelogeneous leukemia. In another embodiment, the cancer is melanoma.

As used herein, the terms "subject" and "animal" include all members of the animal kingdom, in one embodiment the subject is a mammal. In a further embodiment the subject is a human being. In one embodiment, the subject is a patient having a disease, such as a cancer, associated with FGL2-expressing cells.

An effective amount of an antibody or binding fragment thereof, pharmaceutical composition or immunoconjugate of the disclosure relates generally to the amount needed to achieve a therapeutic objective. Common ranges for therapeutically effective dosing of an antibody or binding fragment thereof, pharmaceutical composition or immunoconjugate of the disclosure may be, by way of non-limiting example, from about 0.1 mg kg body weight to about 50 mg/kg body weight. Common dosing frequencies may range, for example, from twice daily to once a week.

Efficaciousness of treatment is determined in association with any known method for diagnosing or treating the particular cancer. Alleviation of one or more symptoms of the cancer indicates that the antibody confers a clinical benefit.

As used herein, "treating a cancer" includes, but is not limited to, reversing, alleviating or inhibiting the progression of the cancer or symptoms or conditions associated with the cancer. "Treating the cancer" also includes extending survival in a subject. Survival is optionally extended by at least 1, 2, 3, 6 or 12 months, or at least 2, 3, 4, 5 or 10 years over the survival that would be expected without treatment with an immunoconjugate or pharmaceutical composition as described herein. "Treating the cancer" also includes reducing tumour mass and/or reducing tumour. Optionally, tumour mass and/or tumour burden is reduced by at least 5, 10, 25, 50, 75 or 100% following treatment with an immunoconjugate or pharmaceutical composition as described herein. "Treating the cancer" also includes reducing the aggressiveness, grade, metastatic potential and/or invasiveness of a tumour. "Treating the cancer" also includes reducing ascites accumulation.

In one embodiment, the active ingredient may be used in combination with at least one additional therapeutic agent. Accordingly, the application provides a method of preventing or treating a cancer using an antibody or binding fragment thereof, pharmaceutical composition or immunoconjugate of the disclosure in combination with at least one additional therapeutic agent. An additional therapeutic agent may be administered prior to, overlapping with, concurrently, and/or after administration of the active ingredients. When administered concurrently, the antibody or binding fragment thereof, pharmaceutical composition or immunoconjugate of the disclosure and an additional therapeutic agent may be administered in a single formulation or in separate formulations, and if administered separately, then optionally, by different modes of administration. The combination of one or more antibody or binding fragments thereof, pharmaceutical compositions or immunoconjugates of the disclosure and one or more other therapeutic agents may synergistically act to combat the cancer.

Embodiments of the additional therapeutic agent include additional FGL2 antibodies or fragments thereof, additional FGL2-binding immunoconjugates, additional FGL2-binding pharmaceutical compositions, cytokines, growth factor inhibitors, immunosuppressants, anti-inflammatory agents, metabolic inhibitors, enzyme inhibitors, anti-neoplastic agents, cytotoxic agents and/or cytostatic agents. Such combination therapies may advantageously utilize lower dosages of an administered active ingredient, thus avoiding possible toxicities or complications associated with monotherapy.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation. All publications, patents and patent applications are herein incorporated by reference in their entirety to the same extent as if each individual publication, patent or patent application was specifically and individually indicated to be incorporated by reference in its entirety.

EXAMPLES

The following non-limiting examples are illustrative of the present disclosure:

Example 1

Figure 1:
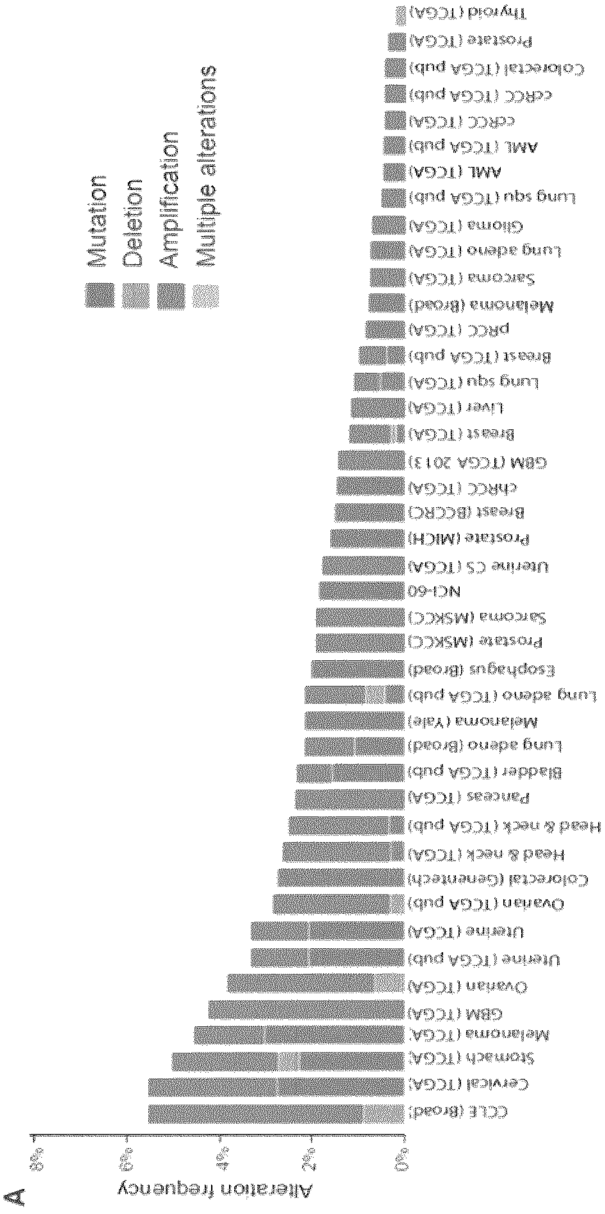

FGL2 mRNA has been detected in cervical, pancreatic, ovarian, uterine, esophageal, melanoma, glioblastoma head and neck, colorectal, bladder, lung, prostate, sarcoma, breast, liver and renal malignancies and acute myelogeneous leukemia (Su et al, 2008). FIG. 1 shows alterations in FGL2, gene mutations, deletions and amplifications in cancer.

Figure 2:
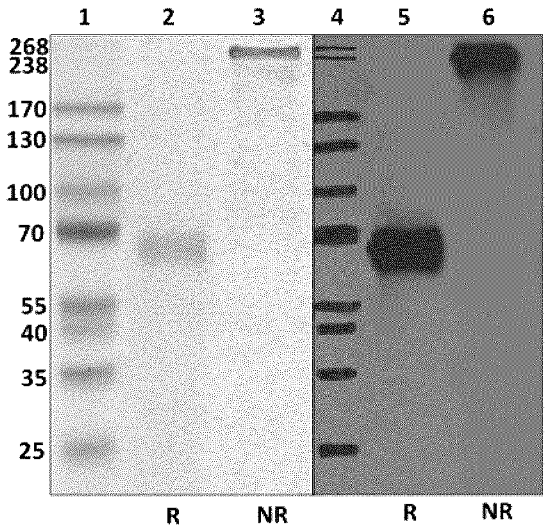
Figure 3:
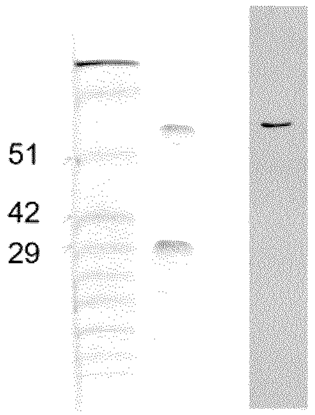
Figure 3:
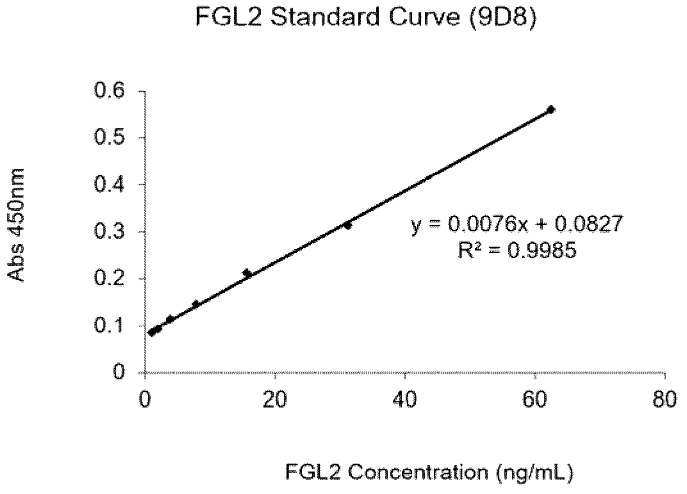

An anti-human monoclonal antibody (9D8) was generated by immunizing BALB/C mice with a full-length human FGL2 protein which was generated in COS-7 cells (FIGS. 2 and 3). BALB/C splenocytes were subsequently fused with the sp2 myeloma cell line and selected in media containing hypoxanthine, aminopterin and thymidine (HAT media). Fused hybridomas were cloned and further selected for binding for human FGL2 by enzyme-linked immunosorbent assay.

Proteins for injection to produce antibodies were devoid of first 29 amino acids in human and 26 amino acids in mouse.

Anti-human monoclonal antibodies 2A5 and 3H9 were generated in the same manner as antibody 9D8.

Characteristics of 9D8:

From a panel of Human FGL2-reactive clones, clone 9D8 was selected as a lead monoclonal antibody which was shown to react with FGL2 by ELISA. It also identified FGL2 by FACS, immunohistochemistry (IHC) and Western blot.

Figure 4:
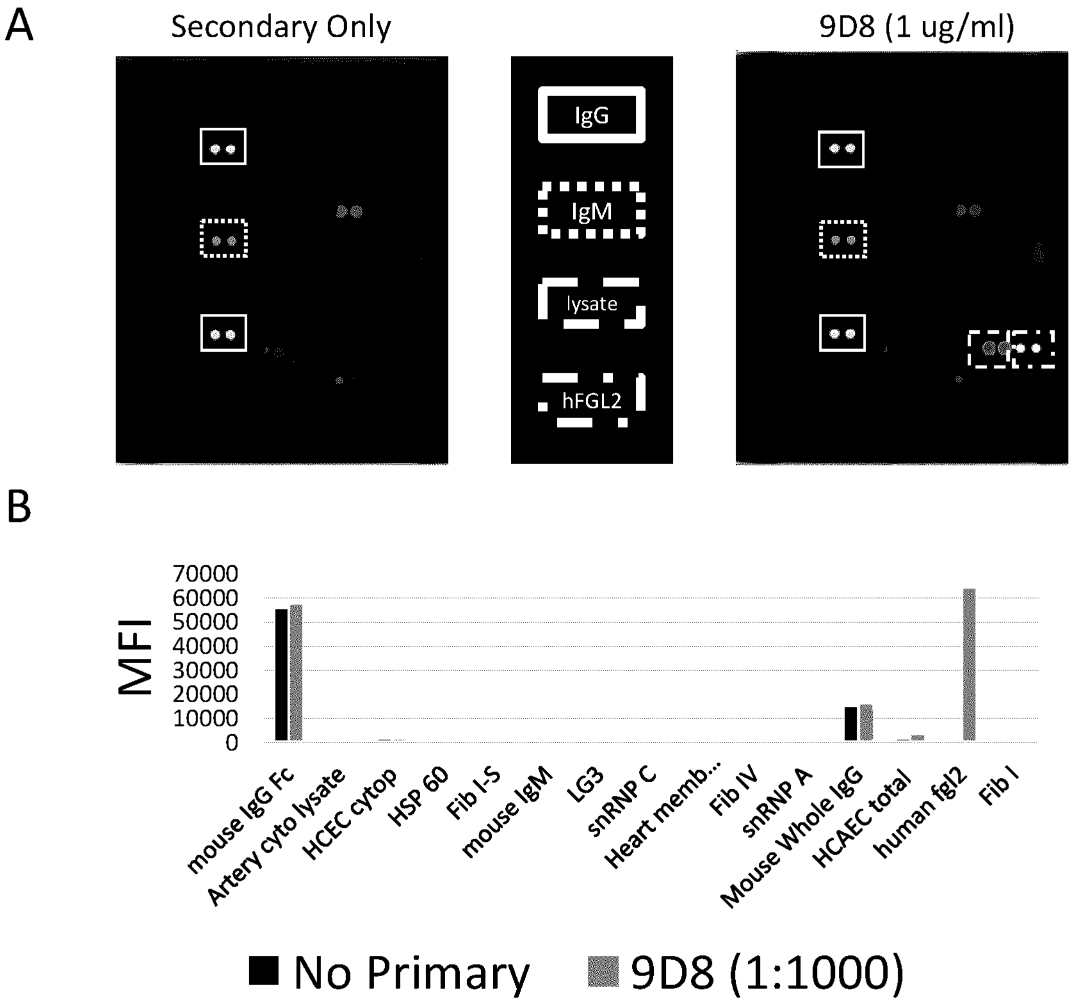
Figure 5:
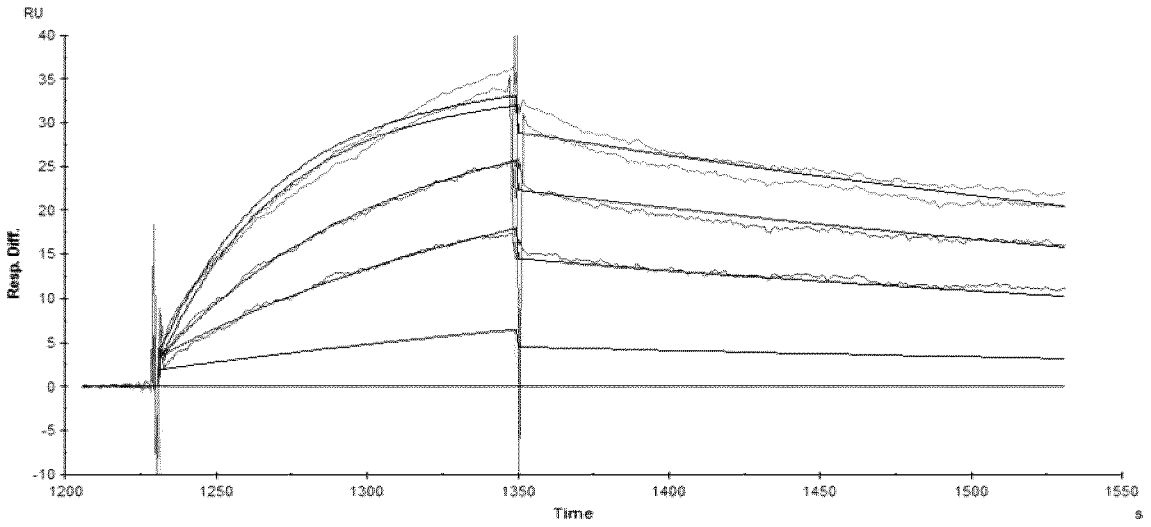
Figure 5:
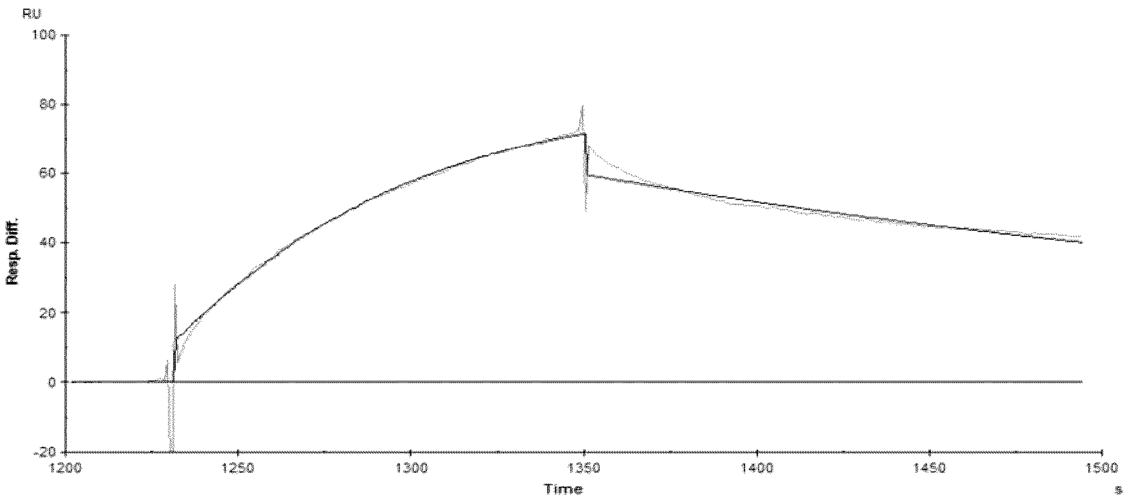

In order determine the selectivity of 9D8 for FGL2, antigen microarrays were probed with this antibody. This technique allows for the determination of antibody binding to antigens in a multiplex fashion (Robinson et al., Nature Medicine, 2002). In this technique, a robotic microarrayer is used to spot antigens onto nitrocellulose-coated slides. The slides are then probed with a primary antibody and then fluorescently labelled secondary antibodies are added. Antigen microarrays were constructed as described previously (Chruscinski et al., Journal of Visualized Experiments, 2016) and had 108 antigens including recombinant proteins, peptides, nuclear antigens and cell lysates (Chruscinski et al., PLoS ONE, 2016). When 9D8 was used to probe the arrays, there was a saturating signal at human FGL2, indicating high affinity binding (FIG. 5A). In addition, 9D8 displayed binding to a human coronary artery endothelial cell lysate (FIG. 5A). The finding that 9D8 bound to the endothelial lysate is consistent with prior studies showing that endothelial cells express FGL2 (Ghanekar, J. Immunol., 2004). Importantly, 9D8 did not display any binding to fibrinogen (type I-S and type I), heat shock proteins, or nuclear proteins, demonstrating that 9D8 is highly selective for human FGL2 (FIG. 4).

Sequences

Sequences of antibodies 9D8, 3H9 and 2A5 are provided in in Tables 2, 3 and 4, respectively.

Sequencing Methods

Total RNA was isolated from 9D8, 3H9 and 2A5 hybridoma cells following the technical manual of TRIzol® Reagent. Total RNA was then reverse-transcribed into cDNA using either isotype-specific anti-sense primers or universal primers following the technical manual of PrimeScript™ 1$^{st}$ Strand cDNA Synthesis Kit. Antibody fragments of VH, VL, CH and CL were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence was provided.

Binding Affinity

The binding affinity ($K_D$) of 9D8 for recombinant human FGL2 was determined by surface plasmon resonance (SPR) to be $8.57\times10^{-10}$ M, and the binding affinity ($K_D$) of 9D8 for recombinant mouse FGL2 was determined by SPR to be $1.8\times10^{-9}$ M (Table 1).

The binding affinity ($K_D$) of 3H9 for recombinant human FGL2 was determined by surface plasmon resonance (SPR) to be $1.03\times10^{-10}$ M, and the binding affinity ($K_D$) of 3H9 for recombinant mouse FGL2 was determined by SPR to be $2.86\times10^{-10}$ (Table 1).

Binding Affinity Methods

Binding experiments were performed on Biacore 3000 at 25° C. Flow cell 2 was coated with 1,000 RU of the goat anti-mouse Fc capture Ab by direct immobilization using EDC/NHS amine coupling method and the unoccupied sites were blocked with 1M ethanolamine. 9D8 or 3H9 was captured at an RU as indicated. Either recombinant human or mouse FGL2 was flowed over the chip and binding to 9D8 or 3H9 was monitored in real time. From the observed kon and koff, KD was determined.

Immunologic Effects of Anti-FGL2 Antibodies

A. In-Vitro

Figure 6:
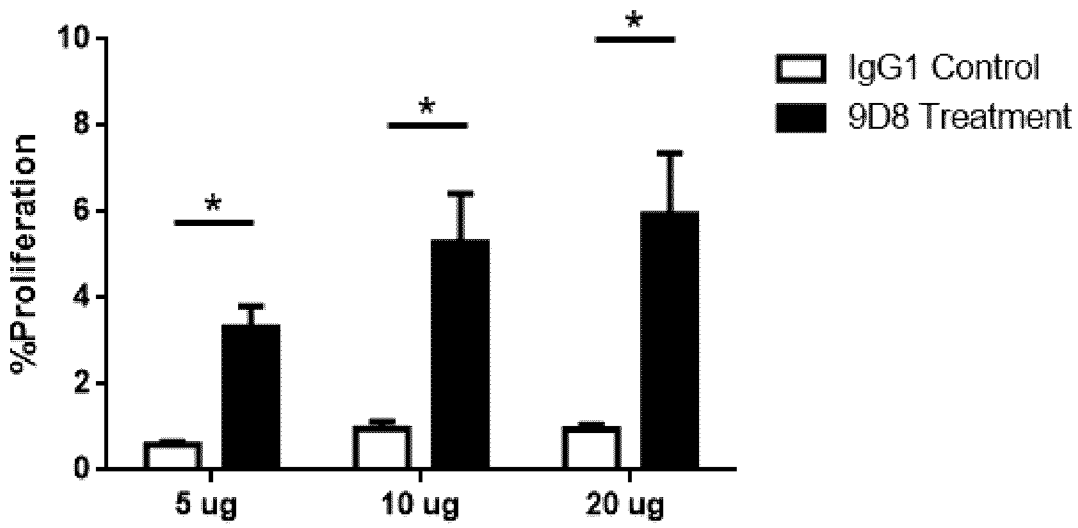
FIG. 6 shows that 9D8 restores T cell proliferation in a one way mouse mixed lymphocyte reaction (MLR).
Figure 7:
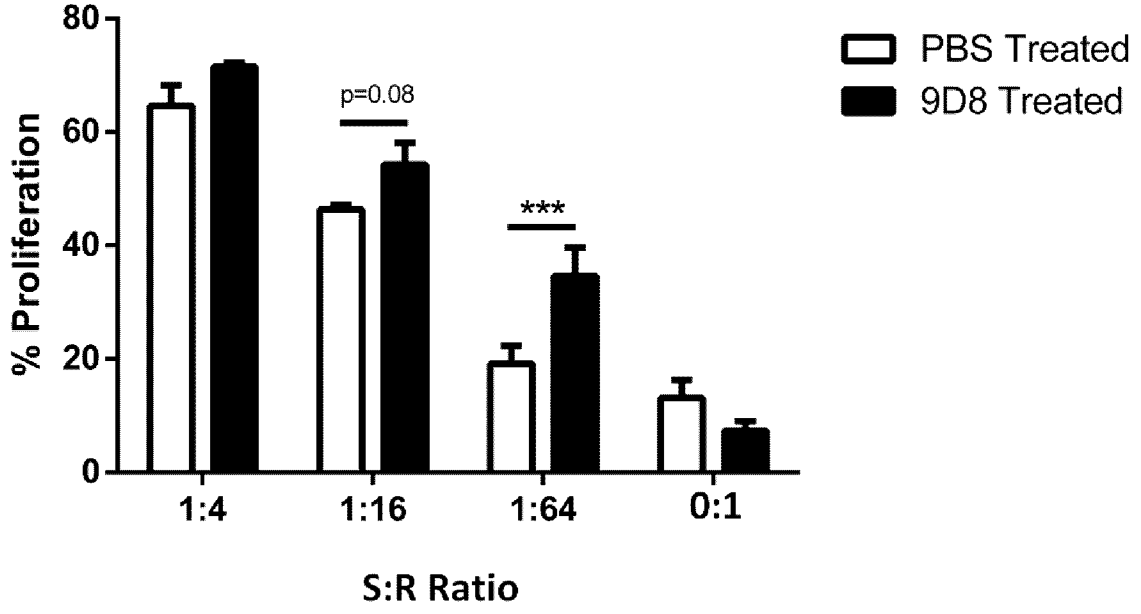
FIG. 7 shows that 9D8 enhances T cell proliferation in a one way human mixed lymphocyte reaction (MLR). Irradiated (2000 rad of y-radiation from a Cesium137 source) simulator cells (S) were added to responder cells at a ratio of 0:1, 1:4, 1:16 and 1:64 and % proliferation was determined by CFSE (Carboxyfluorescein succinimidyl ester) dye dilution by FLOW Cytometry (FACS).

To examine the effect of 9D8 on T cell proliferation, a one way MLR was established using splenic mononuclear cells from BALB/cJ and C3H/HeJ mice. The effect of 9D8 on T cell proliferation was studied by addition of either antibody to FGL2 (9D8) or an isotype control antibody (IgG1). Briefly, $8\times10^5$ BALB/cJ irradiated stimulator cells and $4\times10^5$ C3H/HeJ responders were mixed in the presence of 5, 10 or 20 ug/mL antibody to FGL2 (9D8) or control IgG1 antibody. Proliferation was measured based on the dilution of CFSE by flow cytometry. Values are stated as mean+/−SEM of one experiment with each condition performed in triplicate. It was shown that antibody to FGL2 enhanced proliferation of C3H/HeJ responders in a dose dependent manner compared to isotype-matched control IgG1 antibody (FIG. 6). 9D8 was also shown to enhance T cell proliferation in a human one-way mixed lymphocyte reaction (FIG. 7). Here, irradiated stimulator cells were mixed with CFSE labeled responders in different Stimulator:Effector Ratios in RPMI containing iL-2/10% FCS/10% AB serum/L-Glutamine/Penicillin+Streptomycin with 75 ug/mL of 9D8 or PBS. Cells were incubated at 37 degrees in 5% CO2 for 5 days (Media was replaced at day 3 with either 9D8 or PBS). CFSE dilution was used to measure the cell proliferation in CD3+ T cells by flow cytometry. (*** P<0.001).

Figure 8:
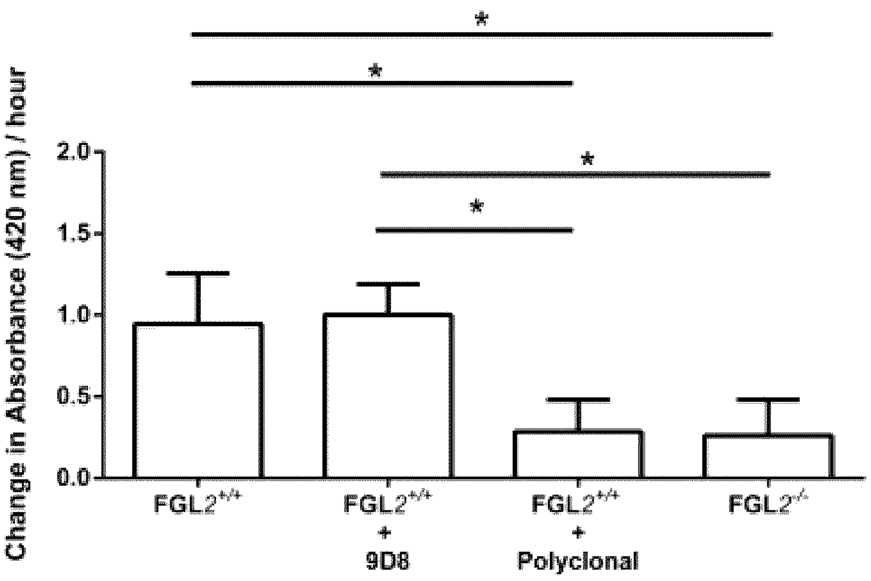
FIG. 8 shows that 9D8 does not inhibit the prothrombinase activity of FGL2.

To examine whether 9D8 inhibits the prothrombinase activity of FGL2, macrophages were isolated from $fgl2^{+/+}$ mice and $fgl2^{-/-}$ mice and measurement of the cleaved thrombin was performed using a chromozym TH colorimetric assay in the presence or absence of antibody to FGL2 (9D8). Briefly, a peritoneal lavage was performed on day 3 thioglycolate-primed $fgl2^{-/-}$ and $fgl2^{+/+}$ mice using hanks balanced salt solution. $3\times10^5$ macrophages were seeded onto flat bottom tissue culture treated 96 well plates and allowed to adhere to the plate for 4 hours at 37° C. in a 5% CO2 environment in Dulbecco's modified Eagle's medium (DMEM) containing 10% fetal calf serum (FCS), L-glutamine (L-Glut) and antibiotics (penicillin and streptomycin) in the presence of or absence of antibody to FGL2 (75 μg/mL). 500 ng of murine prothrombin (Genway Biotech, San Diego, Calif., USA) was applied to the cells in 20 uL for 20 minutes at 37° C./5% CO2. 125 uL of iced cold assay buffer (50 mM Tris, 227 mM NaCl, 1% BSA, pH 8.3) was added after to terminate the prothrombinase reaction. Supernatants were assessed for thrombin activity by the addition of 15 uL of the chromogenic thrombin substrate, Chromozym Th (Roche Applied Science, Indianapolis, Ind.). The absorbance value was measured at 420 nm every 10 minutes for 4 hours. The rate of absorbance change (Abs@420 nm)/min) correlated with prothrombinase activity within each well. The addition of 9D8 to macrophages isolated from $fgl2^{+/+}$ mice did not inhibit prothrombinase activity, while the addition of polyclonal antibody to FGL2 inhibited prothrombinase activity to the same extent as macrophages isolated from $fgl2^{-/-}$ mice (FIG. 8).

Figure 9:
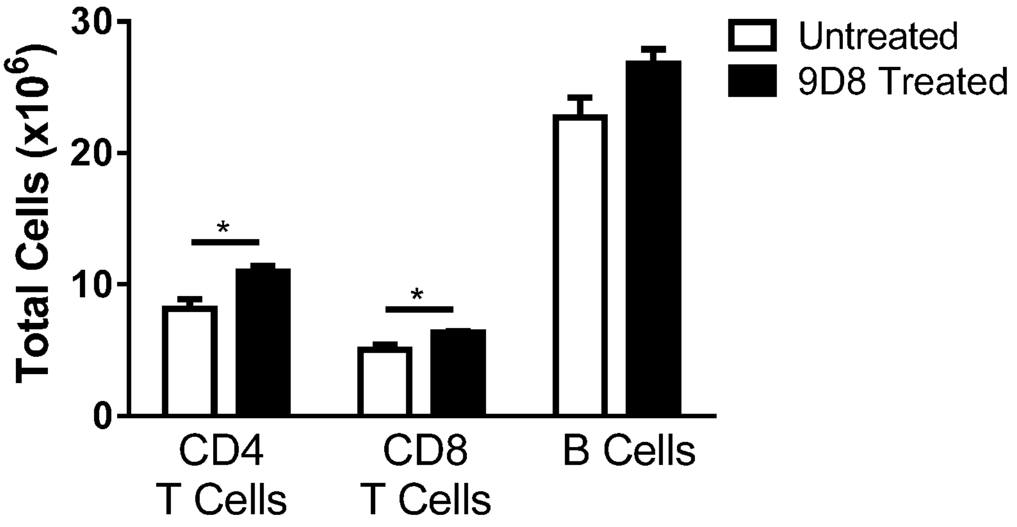
FIG. 9 shows that 9D8 is not cytotoxic. A) Studies in T cells and B cells, B) Studies in macrophages and dendritic cells, C) Studies in NK cells and NKT cells.
Figure 9:
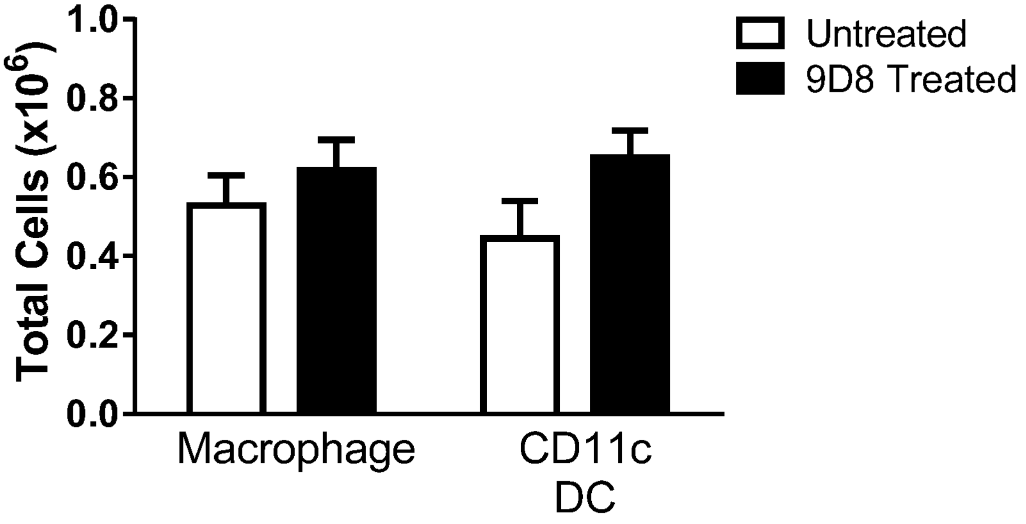

To examine whether 9D8 could deplete major subsets of immune cells, $Fgl2^{+/+}$ mice were injected with 150 μg of 9D8 or were untreated. Splenic mononuclear cells were isolated at day 3 post-injection and total numbers of B cells, CD4+ T cells and CD8+ T cells (FIG. 9*a*) or Macrophage and DC (FIG. 9*b*) or NK cells and NK T cells (FIG. 9*c*) were quantified by flow cytometry. It was found that there was no depletion effect of 9D8 on major subsets of immune cells.

An in vitro suppression assay was utilized to assess the ability of monoclonal antibodies 2A5, 3H9 and 9D8 to inhibit in vitro suppression by regulatory T cells (Tregs). $2\times10^4$ $CD4^+$ $CD25^-$ T cells from C57Bl/6J ($fgl2^{+/+}$) mice as responder cells, together with $8\times10^4$ irradiated splenic mononuclear cells as antigen presenting cells (APC) and titrated numbers of CD4+$CD25^+$ Tregs as suppressor cells which were stimulated with Concanavalin A (Con A) (1 ug/mL) for 72 hours. 3H thymidine was added for the last 18 hours to measure proliferation of effector cells. For the antibody blockade studies, titrated concentrations of the monoclonal antibodies to FGL2 were added to the cell cultures at a 1:4 suppressor:responder cell ratio in the presence of APC and Con A.

Figure 10:
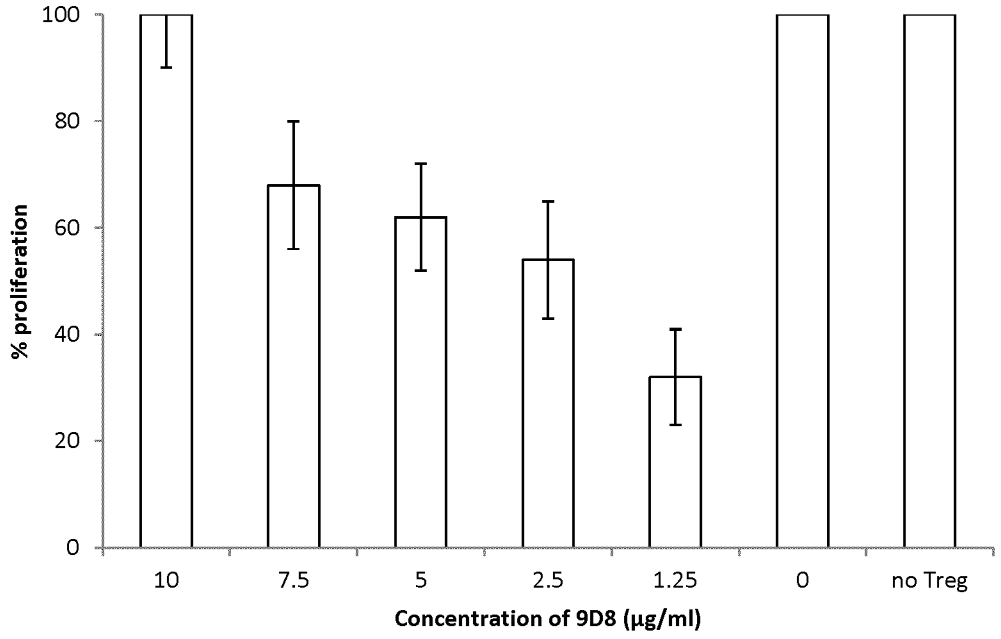
FIG. 10 shows that antibody 9D8 restores proliferation of T effector cells in the presence of Treg cells. The graph represents the mean+/− SEM from three independent experiments.
Figure 11:
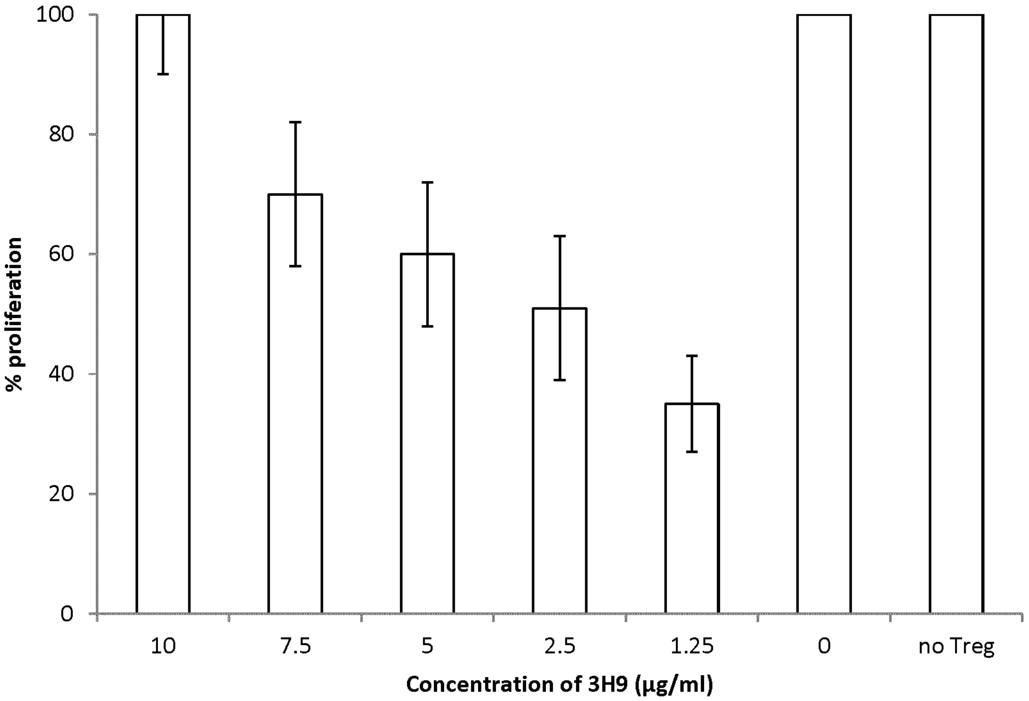
FIG. 11 shows that antibody 3H9 restores proliferation of T effector cells in the presence of Treg cells. The graph represents the mean+/− SEM from three independent experiments.
Figure 12:
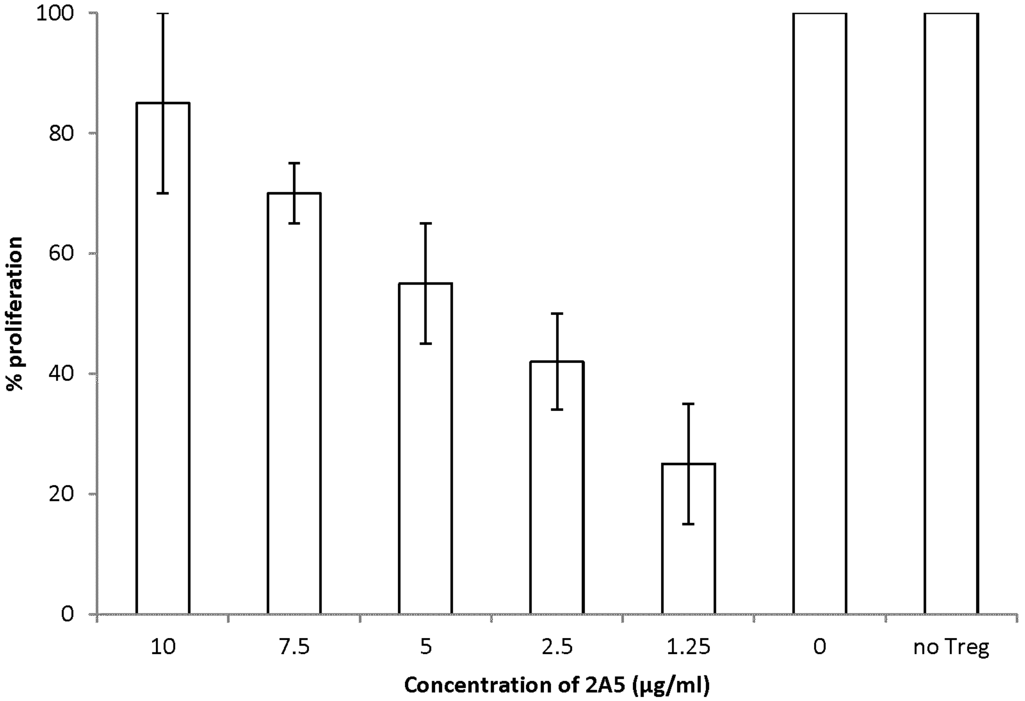
FIG. 12 shows that antibody 2A5 restores proliferation of T effector cells in the presence of Treg cells. The graph represents the mean+/− SEM from three independent experiments.

As shown in FIGS. 10 to 12, all three antibodies to FGL2 (9D8, 3H9 and 2A5) were able to inhibit the suppressor cell activity of Tregs in a dose dependent fashion whereas an isotype control antibody had no effect.

B. In Vivo: Effect of Anti FGL2 9D8 in Ovarian Cancer

Figure 13:
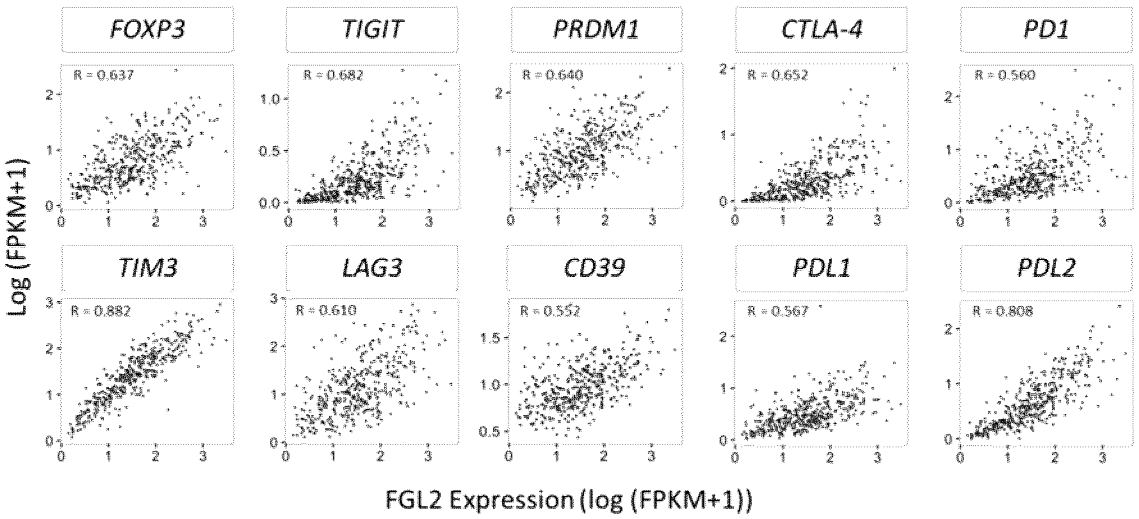
FIG. 13 shows a Pearson correlation analysis of The Cancer Genome Atlas of ovarian cancers comparing levels of FGL2 expression to levels of immune cells markers and checkpoint inhibitors.
Figure 14:
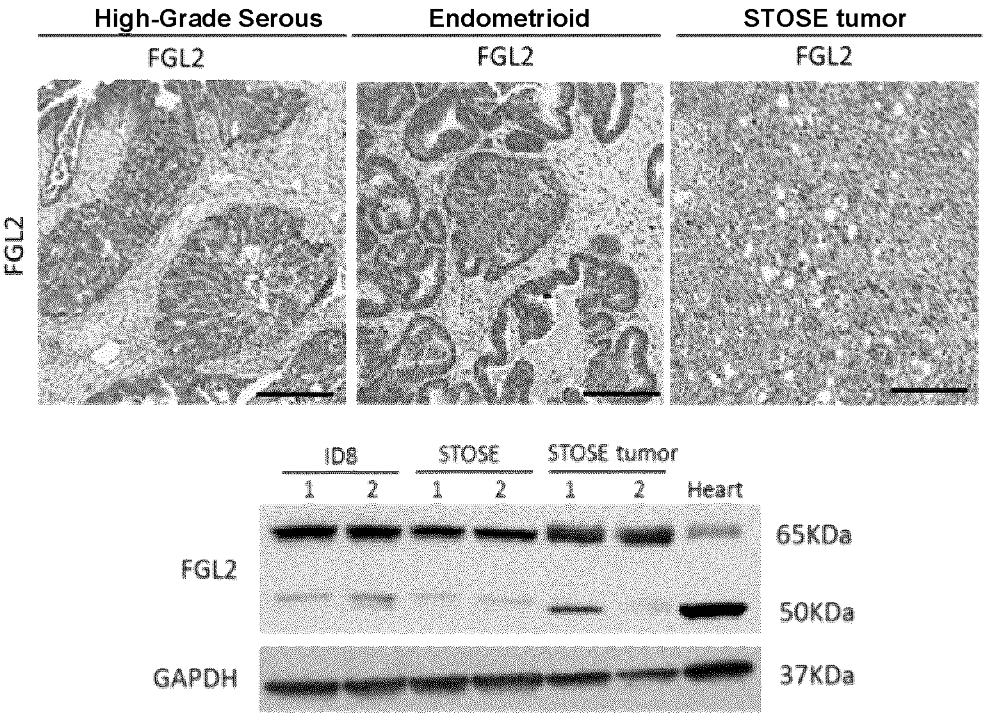
FIG. 14 shows that FGL2 is expressed in human HGSC, endometrioid carcinoma and the STOSE model. FGL2 is expressed in human ovarian cancers, in the two syngeneic mouse ovarian cancer cell lines (ID8 and STOSE), and in STOSE tumors.
Figure 15:
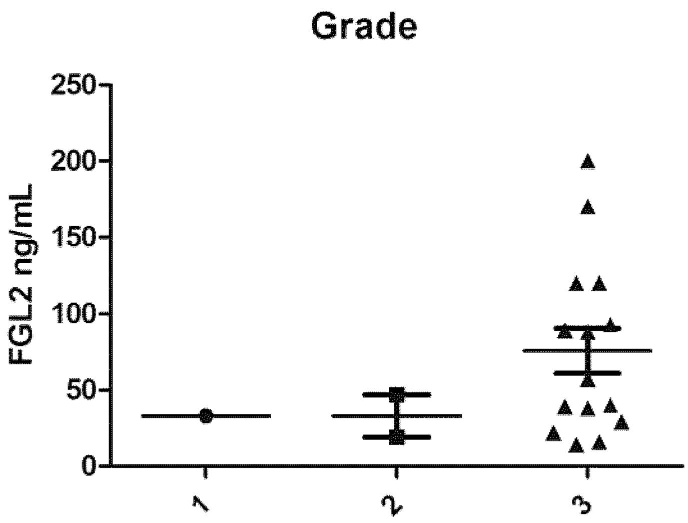
FIG. 15 shows that FGL2 is present at variable levels in ascites fluid at various (A) grades, (B) stages and (C) subtypes of human ovarian cancer, as measured by ELISA.
Figure 15:
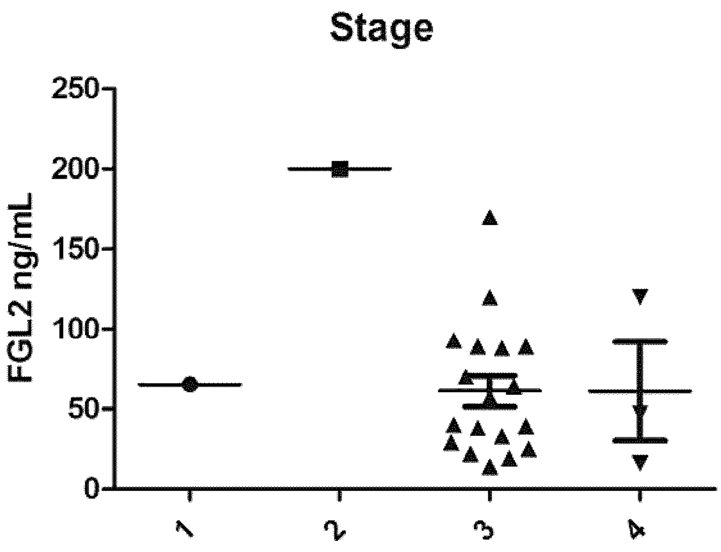

The presence of Tregs in ovarian cancers is known to correlate with poor prognosis and failure of emerging immunotherapies (Curiel et al, 2004), due to their role in suppressing antigen presentation from dendritic cells and in inducing CD8+ T cell exhaustion (Hamanishi et al, 2016b; Latha et al, 2014). To determine if FGL2 is a viable therapeutic target in human ovarian cancer, The Cancer Genome Atlas dataset of HGSC on cBioPortal (Latha et al, 2014) https://paperpile.com/c/hgol4U/5OL0k was accessed. It was found that FGL2 is positively correlated with numerous markers of Tregs (CD39, FOXP3, PRDM1, LAG3) and with the expression of immune checkpoint inhibitor targets (PD1, PD-L1, PD-L2, CTLA-4) (FIG. 13). This suggests that FGL2 may be a central mediator of Treg function in HGSC. Some of the immune checkpoint inhibitors that block co-inhibitory receptors and inhibit Treg function (anti-PD1, PD-L1, CTLA-4) are currently in clinical trials for numerous cancers, including ovarian cancer (Hamanishi et al, 2016b) https://paperpile.com/c/hgol4U/Zu1Ye, it is becoming clear that, while checkpoint inhibition is showing promise in ovarian cancer, the response rate is generally <20% (Hamanishi et al, 2016). Developing therapeutics to attenuate the immunosuppressive tumor microenvironment in combination with, or beyond checkpoint inhibition is a necessary goal. Analysis of openly accessible tissue microarrays of ovarian cancer followed by validation with tissue bank samples of ovarian cancer showed that FGL2 is expressed in both the epithelial and stromal compartments, showing that FGL2-based therapies could have utility in multiple subtypes of ovarian cancer (FIG. 14). In addition, the measurement (by ELISA) of FGL2 in abdominal ascites from women with ovarian cancer, shows that FGL2 is present at variable levels at all stages, grades and subtypes of ovarian cancer (FIG. 15).

To determine the efficacy of anti-FGL2 therapy on ovarian cancer, anti-FGL2 antibody (clone 9D8) was studied in a syngeneic model of ovarian cancer (ID8) which following injection forms tumors in fully competent C57Bl/6 mice (Pengetnze et al, 2003). The protocol employed is shown in FIG. 16. Briefly, ID8 cells were engrafted under the ovarian bursal membrane, as reported previously (McCloskey et al, 2014) to generate an orthotopic model of ovarian cancer. When tumors became palpable (~28 days), mice were treated with intraperitoneal 150 μg anti-FGL2 antibody or an isotype control antibody every 2 days for 10 days, at which point the mice were euthanized to measure tumor burden. The percentages of immune infiltrates in the tumors were assessed using flow cytometry for markers of Tregs (CD25, FOXP3, CTLA4, CD3, CD4), effector and exhausted CD8+ T cells (Ly6C, LAG3, PD1, BTLA, KLRG-1, CD3, CD8), NKs/NKTs (DX5, KLRG1, NK1.1, CD3) DCs (CD11c, MHC-II, CD86) and macrophages (CD11b, MHC-II, CD86, Gr1).

Here it is shown that treatment with anti-FGL2 therapy slowed tumor progression relative to controls (FIG. 17). It is also demonstrated by flow cytometry (FACS) that treatment of mice with antibody to FGL2 reduced the numbers of Tregs and increased the total number of leukocytes which were predominantly CD3+ and CD4+ cells in the tumors (FIG. 18).

Discussion:

A number of studies have shown that FGL2 is increased in a number of human malignancies. Here it is shown that FGL2 is expressed within ovarian tumours and within tumour infiltrating Treg. This study is the first study showing the use of a specific monoclonal antibody to FGL2, 9D8 ameliorates ovarian cancer and restores anti-tumour immune activity and reduces intra-tumour Treg activity. Both processes are known to be linked and important in the pathogenesis of cancer (Yan et al, 2015). Without being bound by theory, that inhibition of FGL2 reduces Treg numbers may directly explain the enhanced effector immunity and tumour reduction as FGL2 has been shown to suppress TH1 responses, and downregulates antigen presenting cell activity. Alternatively, the effect of FGL2 may be by blocking FGL2 activity generated by the tumour. It has been previously reported that FGL2 inhibits other immune checkpoints and in particular blocks PD-1 expression on $CD45^+$ lymphocytes. This could explain the marked increase in CD45+ leukocytes in anti FGL2 treated mice. Given that FGL2 mRNA is elevated (compared to normal tissue) in solid tumours, FGL2 is useful as a therapeutic target in ovarian and other cancers.

TABLE 2

9D8 Sequences

9D8 Heavy chain-amino acid sequence

| | SEQ ID NO: | |
|---|---|---|
| Leader sequence | 1 | MKCSWVIFFLMAVVTGVNS |
| FR1 | 2 | EVQLQQSGAELVKPGASVQLSCTASGFNIK |
| CDR-H1 | 3 | **DTYIH** |
| FR2 | 4 | WVKQRPEQGLEWIG |
| CDR-H2 | 5 | **RIDPEDGNTKYDPKFQA** |
| FR3 | 6 | KATITADTFSNTAYLQLSSLTSEDTAVYYCAR |
| CDR-H3 | 7 | **SYGNAY** |
| FR4 | 8 | WGQGTLVTVSA |
| Constant region | 9 | AKTTPPSVYPLAPGSAAQTNSMVTLGCLVKGYFPEPVTVT WNSGSLSSGVHTFPAVLQSDLYTLSSSVTVPSSTWPSET VTCNVAHPASSTKVDKKIVPRDCGCKPCICTVPEVSSVFIF PPKPKDVLTITLTPKVTCVVVDISKDDPEVQFSWFVDDVE VHTAQTQPREEQFNSTFRSVSELPIMHQDWLNGKEFKCR VNSAAFPAPIEKTISKTKGRPKAPQVYTIPPPKEQMAKDKV SLTCMITDFFPEDITVEWQWNGQPAENYKNTQPIMDTDG SYFVYSKLNVQKSNWEAGNTFTCSVLHEGLHNHHTEKSL SHSPGK |

9D8 Light chain amino acid sequence

| | SEQ ID NO: | |
|---|---|---|
| Leader sequence | 10 | METDTLLLWVLLLWVPGSTG |
| FR1 | 11 | DIVLTQSPASLAVSLGQRATISC |
| CDR-L1 | 12 | **RASQSVSTSRYTYMH** |
| FR2 | 13 | WYQQKPGQPPKLLIK |
| CDR-L2 | 14 | **YASNLDS** |
| FR3 | 15 | GVPARFSGSGSGTDFTLNIHPVQEEDTATYYC |
| CDR-L3 | 16 | **QHSWEIWA** |
| FR4 | 17 | FGGGTKLEIK |
| Constant region | 18 | RADAAPTVSIFPPSSEQLTSGGASVVCFLNNFYPKDINVK WKIDGSERQNGVLNSWTDQDSKDSTYSMSSTLTLTKDEY ERHNSYTCEATHKTSTSPIVKSFNRNEC |

TABLE 2-continued

| 9D8 Sequences | | |
|---|---|---|
| 9D8 Heavy chain-nucleic acid sequence | | |
| | SEQ ID NO: | |
| Leader sequence | 19 | ATGAAATGCAGCTGGGTTATCTTCTTCCTGATGGCAGT GGTTACAGGGGTCAATTCA |
| FR1 | 20 | GAGGTTCAGCTGCAGCAGTCTGGGGCAGAGCTTGTGA AGCCAGGGGCCTCAGTCCAGTTGTCCTGCACAGCTTCT GGCTTCAACATTAAA |
| CDR-H1 | 21 | GACACCTATATACAC |
| FR2 | 22 | TGGGTGAAACAGAGGCCTGAACAGGGCCTGGAGTGGA TTGGA |
| CDR-H2 | 23 | AGGATTGATCCTGAGGATGGCAATACTAAATATGACCC GAAGTTCCAGGCC |
| FR3 | 24 | AAGGCCACTATAACAGCAGACACATTCTCCAATACAGC CTACCTGCAGCTCAGCAGCCTGACATCTGAGGACACTG CCGTCTATTACTGTGCTAGA |
| CDR-H3 | 25 | TCGTATGGTAACGCTTAC |
| FR4 | 26 | TGGGGCCAAGGGACTCTGGTCACTGTCTCTGCA |
| Constant region | 27 | GCCAAAACGACACCCCCATCTGTCTATCCACTGGCCCC TGGATCTGCTGCCCAAACTAACTCCATGGTGACCCTGG GATGCCTGGTCAAGGGCTATTTCCCTGAGCCAGTGACA GTGACCTGGAACTCTGGATCCCTGTCCAGCGGTGTGC ACACCTTCCCAGCTGTCCTGCAGTCTGACCTCTACACT CTGAGCAGCTCAGTGACTGTCCCCTCCAGCACCTGGC CCAGCGAGACCGTCACCTGCAACGTTGCCCACCCGGC CAGCAGCACCAAGGTGGACAAGAAAATTGTGCCCAGG GATTGTGGTTGTAAGCCTTGCATATGTACAGTCCCAGA AGTATCATCTGTCTTCATCTTCCCCCCAAAGCCCAAGG ATGTGCTCACCATTACTCTGACTCCTAAGGTCACGTGT GTTGTGGTAGACATCAGCAAGGATGATCCCGAGGTCCA GTTCAGCTGGTTTGTAGATGATGTGGAGGTGCACACAG CTCAGACGCAACCCCGGGAGGAGCAGTTCAACAGCAC TTTCCGCTCAGTCAGTGAACTTCCCATCATGCACCAGG ACTGGCTCAATGGCAAGGAGTTCAAATGCAGGGTCAAC AGTGCAGCTTTCCCTGCCCCCATCGAGAAAACCATCTC CAAAACCAAAGGCAGACCGAAGGCTCCACAGGTGTAC ACCATTCCACCTCCCAAGGAGCAGATGGCCAAGGATAA AGTCAGTCTGACCTGCATGATAACAGACTTCTTCCCTG AAGACATTACTGTGGAGTGGCAGTGGAATGGGCAGCC AGCGGAGAACTACAAGAACACTCAGCCCATCATGGACA CAGATGGCTCTTACTTCGTCTACAGCAAGCTCAATGTG CAGAAGAGCAACTGGGAGGCAGGAAATACTTTCACCTG CTCTGTGTTACATGAGGGCCTGCACAACCACCATACTG AGAAGAGCCTCTCCCACTCTCCTGGTAAATGA |
| 9D8 Light chain-nucleic acid sequence | | |
| | SEQ ID NO: | |
| Leader sequence | 28 | ATGGAGACAGACACACTCCTGCTATGGGTGCTGCTGCT CTGGGTTCCAGGTTCCACTGGT |
| FR1 | 29 | GACATTGTGCTGACACAGTCTCCTGCTTCCTTAGCTGT ATCTCTGGGGCAGAGGGCCACCATCTCATGC |
| CDR-L1 | 30 | AGGGCCAGCCAAAGTGTCAGTACATCTAGGTACACTTA TATGCAC |
| FR2 | 31 | TGGTACCAACAGAAACCAGGACAGCCACCCAAACTCCT CATCAAA |
| CDR-L2 | 32 | TATGCATCCAACCTAGATTCT |

TABLE 2-continued

| 9D8 Sequences | | |
|---|---|---|
| FR3 | 33 | GGGGTCCCTGCCAGGTTCAGTGGCAGTGGGTCTGGGA<br>CAGACTTCACCCTCAACATCCATCCTGTGCAGGAGGAG<br>GATACTGCAACATATTACTGT |
| CDR-L3 | 34 | CAGCACAGTTGGGAGATTTGGGCG |
| FR4 | 35 | TTCGGTGGAGGCACCAAGCTGGAAATCAAA |
| Constant region | 36 | CGGGCTGATGCTGCACCAACTGTATCCATCTTCCCACC<br>ATCCAGTGAGCAGTTAACATCTGGAGGTGCCTCAGTCG<br>TGTGCTTCTTGAACAACTTCTACCCCAAAGACATCAATG<br>TCAAGTGGAAGATTGATGGCAGTGAACGACAAAATGGC<br>GTCCTGAACAGTTGGACTGATCAGGACAGCAAAGACAG<br>CACCTACAGCATGAGCAGCACCCTCACGTTGACCAAG<br>GACGAGTATGAACGACATAACAGCTATACCTGTGAGGC<br>CACTCACAAGACATCAACTTCACCCATTGTCAAGAGCTT<br>CAACAGGAATGAGTGTTAG |
| 9D8 Heavy chain: Amino acid sequence (458 aa) Leader sequence-FR1-CDR1-FR2-CDR2-FR3-CDR3-FR4-Constant region-Stop codon | 37 | MKCSWVIFFLMAVVTGVNSEVQLQQSGAELVKPGASVQL<br>SCTASGFNIKDTYIHWVKQRPEQGLEWIGRIDPEDGNTKY<br>DPKFQAKATITADTFSNTAYLQLSSLTSEDTAVYYCARSY<br>GNAYWGQGTLVTVSAAKTTPPSVYPLAPGSAAQTNSMVT<br>LGCLVKGYFPEPVTVTWNSGSLSSGVHTFPAVLQSDLYT<br>LSSSVTVPSSTWPSETVTCNVAHPASSTKVDKKIVPRDCG<br>CKPCICTVPEVSSVFIFPPKPKDVLTITLTPKVTCVVVDISK<br>DDPEVQFSWFVDDVEVHTAQTQPREEQFNSTFRSVSELP<br>IMHQDWLNGKEFKCRVNSAAFPAPIEKTISKTKGRPKAPQ<br>VYTIPPPKEQMAKDKVSLTCMITDFFPEDITVEWQWNGQP<br>AENYKNTQPIMDTDGSYFVYSKLNVQKSNWEAGNTFTCS<br>VLHEGLHNHHTEKSLSHSPGK |
| 9D8 Heavy chain variable region: Amino acid sequence FR1-CDR1-FR2-CDR2-FR3-CDR3-FR4 | 38 | EVQLQQSGAELVKPGASVQLSCTASGFNIKDTYIHWVKQ<br>RPEQGLEWIGRIDPEDGNTKYDPKFQAKATITADTFSNTA<br>YLQLSSLTSEDTAVYYCARSYGNAYWGQGTLVTVSA |
| 9D8 Light chain: Amino acid sequence (237 aa) Leader sequence-FR1-CDR1-FR2-CDR2-FR3-CDR3-FR4-Constant region-Stop codon | 39 | METDTLLLWVLLLWVPGSTGDIVLTQSPASLAVSLGQRAT<br>ISCRASQSVSTSRYTYMHWYQQKPGQPPKLLIKYASNLD<br>SGVPARFSGSGSGTDFTLNIHPVQEEDTATYYCQHSWEI<br>WAFGGGTKLEIKRADAAPTVSIFPPSSEQLTSGGASVVCF<br>LNNFYPKDINVKWKIDGSERQNGVLNSWTDQDSKDSTYS<br>MSSTLTLTKDEYERHNSYTCEATHKTSTSPIVKSFNRNEC |
| 9D8 Light chain variable region: Amino acid sequence FR1-CDR1-FR2-CDR2-FR3-CDR3-FR4 | 40 | DIVLTQSPASLAVSLGQRATISCRASQSVSTSRYTYMHWY<br>QQKPGQPPKLLIKYASNLDSGVPARFSGSGSGTDFTLNIH<br>PVQEEDTATYYCQHSWEIWAFGGGTKLEIK |
| 9D8 Heavy chain: DNA sequence (1377 bp) Leader sequence-FR1-CDR1-FR2-CDR2-FR3-CDR3-FR4-Constant region-Stop codon | 41 | ATGAAATGCAGCTGGGTTATCTTCTTCCTGATGGCAGT<br>GGTTACAGGGGTCAATTCAGAGGTTCAGCTGCAGCAGT<br>CTGGGGCAGAGCTTGTGAAGCCAGGGGCCTCAGTCCA<br>GTTGTCCTGCACAGCTTCTGGCTTCAACATTAAAGACA<br>CCTATATACACTGGGTGAAACAGAGGCCTGAACAGGG<br>CCTGGAGTGGATTGGAAGGATTGATCCTGAGGATGGC<br>AATACTAAATATGACCCGAAGTTCCAGGCCAAGGCCAC<br>TATAACAGCAGACACATTCTCCAATACAGCCTACCTGC<br>AGCTCAGCAGCCTGACATCTGAGGACACTGCCGTCTAT<br>TACTGTGCTAGATCGTATGGTAACGCTTACTGGGGCCA<br>AGGGACTCTGGTCACTGTCTCTGCAGCCAAAACGACAC<br>CCCCATCTGTCTATCCACTGGCCCCTGGATCTGCTGCC<br>CAAACTAACTCCATGGTGACCCTGGGATGCCTGGTCAA<br>GGGCTATTTCCCTGAGCCAGTGACAGTGACCTGGAACT<br>CTGGATCCCTGTCCAGCGGTGTGCACACCTTCCCAGCT<br>GTCCTGCAGTCTGACCTCTACACTCTGAGCAGCTCAGT<br>GACTGTCCCCTCCAGCACCTGGCCCAGCGAGACCGTC<br>ACCTGCAACGTTGCCCACCCGGCCAGCAGCACCAAGG<br>TGGACAAGAAAATTGTGCCCAGGGATTGTGGTTGTAAG<br>CCTTGCATATGTACAGTCCCAGAAGTATCATCTGTCTTC |

TABLE 2-continued

| 9D8 Sequences | | |
|---|---|---|
| | | ATCTTCCCCCCAAAGCCCAAGGATGTGCTCACCATTAC TCTGACTCCTAAGGTCACGTGTGTTGTGGTAGACATCA GCAAGGATGATCCCGAGGTCCAGTTCAGCTGGTTTGTA GATGATGTGGAGGTGCACACAGCTCAGACGCAACCCC GGGAGGAGCAGTTCAACAGCACTTTCCGCTCAGTCAGT GAACTTCCCATCATGCACCAGGACTGGCTCAATGGCAA GGAGTTCAAATGCAGGGTCAACAGTGCAGCTTTCCCTG CCCCCATCGAGAAAACCATCTCCAAAACCAAAGGCAGA CCGAAGGCTCCACAGGTGTACACCATTCCACCTCCCAA GGAGCAGATGGCCAAGGATAAAGTCAGTCTGACCTGC ATGATAACAGACTTCTTCCCTGAAGACATTACTGTGGA GTGGCAGTGGAATGGGCAGCCAGCGGAGAACTACAAG AACACTCAGCCCATCATGGACACAGATGGCTCTTACTT CGTCTACAGCAAGCTCAATGTGCAGAAGAGCAACTGG GAGGCAGGAAATACTTTCACCTGCTCTGTGTTACATGA GGGCCTGCACAACCACCATACTGAGAAGAGCCTCTCC CACTCTCCTGGTAAATGA |
| 9D8 Light chain: DNA sequence (714 bp) Leader sequence-FR1-CDR1-FR2-CDR2-FR3-CDR3-FR4-Constant region-Stop codon | 42 | ATGGAGACAGACACACTCCTGCTATGGGTGCTGCTGCT CTGGGTTCCAGGTTCCACTGGTGACATTGTGCTGACAC AGTCTCCTGCTTCCTTAGCTGTATCTCTGGGGCAGAGG GCCACCATCTCATGCAGGGCCAGCCAAAGTGTCAGTA CATCTAGGTACACTTATATGCACTGGTACCAACAGAAA CCAGGACAGCCACCCAAACTCCTCATCAAATATGCATC CAACCTAGATTCTGGGGTCCCTGCCAGGTTCAGTGGCA GTGGGTCTGGGACAGACTTCACCCTCAACATCCATCCT GTGCAGGAGGAGGATACTGCAACATATTACTGTCAGCA CAGTTGGGAGATTTGGGCGTTCGGTGGAGGCACCAAG CTGGAAATCAAACGGGCTGATGCTGCACCAACTGTATC CATCTTCCCACCATCCAGTGAGCAGTTAACATCTGGAG GTGCCTCAGTCGTGTGCTTCTTGAACAACTTCTACCCC AAAGACATCAATGTCAAGTGGAAGATTGATGGCAGTGA ACGACAAAATGGCGTCCTGAACAGTTGGACTGATCAGG ACAGCAAAGACAGCACCTACAGCATGAGCAGCACCCT CACGTTGACCAAGGACGAGTATGAACGACATAACAGCT ATACCTGTGAGGCCACTCACAAGACATCAACTTCACCC ATTGTCAAGAGCTTCAACAGGAATGAGTGTTAG |

TABLE 3

| 3H9 Sequences | | |
|---|---|---|
| 3H9 Heavy chain-amino acid sequence | | |
| | SEQ ID NO: | |
| Leader sequence | 43 | MGWSWIFLFLLSGTAGVLS |
| FR1 | 44 | EVQLQQSGPELVKSGASVKISCKTSGYTFT |
| CDR-H1 | 45 | **EYTIH** |
| FR2 | 46 | WVKQSHGESLEWVG |
| CDR-H2 | 47 | **GINPKNGGISYNQKFKG** |
| FR3 | 48 | KATLTVDKSSSTAYMELRSLTSEDSAVYFCAR |
| CDR-H3 | 49 | **WGIGNYVGFPY** |
| FR4 | 50 | WGQGTLVTVSA |
| Constant region | 51 | AKTTPPSVYPLAPGCGDTTGSSVTLGCLVKGYFPESVTVT WNSGSLSSSVHTFPALLQSGLYTMSSSVTVPSSTWPSQT VTCSVAHPASSTTVDKKLEPSGPISTINPCPPCKECHKCP APNLEGGPSVFIFPPNIKDVLMISLTPKVTCVVVDVSEDDP DVQISWFVNNVEVHTAQTQTHREDYNSTIRVVSTLPIQHQ DWMSGKEFKCKVNNKDLPSPIERTISKIKGLVRAPQVYILP PPAEQLSRKDVSLTCLVVGFNPGDISVEWTSNGHTEENY KDTAPVLDSDGSYFIYSKLNMKTSKWEKTDSFSCNVRHE GLKNYYLKKTISRSPGK |

TABLE 3-continued

| 3H9 Sequences | | |
|---|---|---|
| **3H9 Light chain-amino acid sequence** | | |
| | SEQ ID NO: | |
| Leader sequence | 52 | MKSQTQVFVFLLLCVSGVHG |
| FR1 | 53 | SIVMTQTPKFLLVSAGDRVTMTC |
| CDR-L1 | 54 | **KASLSVNNDVA** |
| FR2 | 55 | WYQQKPGQSPKLLIS |
| CDR-L2 | 56 | **YASSRYT** |
| FR3 | 57 | GVPDRFTGSGYGTDFTFTISSVQAEDLAVYFC |
| CDR-L3 | 58 | **QQDYSSPLT** |
| FR4 | 59 | FGAGTKLELK |
| Constant region | 60 | RADAAPTVSIFPPSSEQLTSGGASVVCFLNNFYPKDINVK<br>WKIDGSERQNGVLNSWTDQDSKDSTYSMSSTLTLTKDEY<br>ERHNSYTCEATHKTSTSPIVKSFNRNEC |
| **3H9 Heavy chain-nucleic acid sequence** | | |
| | SEQ ID NO: | |
| Leader sequence | 61 | ATGGGATGGAGCTGGATCTTTCTCTTTCTCCTGTCAGG<br>AACTGCAGGTGTCCTCTCT |
| FR1 | 62 | GAGGTCCAGCTGCAACAGTCTGGACCTGAGCTGGTGA<br>AGTCTGGGGCTTCAGTGAAGATATCCTGCAAGACCTCT<br>GGATACACTTTCACT |
| CDR-H1 | 63 | GAATACACCATACAC |
| FR2 | 64 | TGGGTGAAGCAGAGCCATGGAGAGAGCCTTGAGTGGG<br>TTGGA |
| CDR-H2 | 65 | GGTATTAATCCTAAAAATGGTGGTATTAGTTACAACCAG<br>AAGTTCAAGGGC |
| FR3 | 66 | AAGGCCACATTGACTGTAGACAAGTCCTCCAGCACAGC<br>CTACATGGAGCTCCGCAGCCTGACATCTGAGGATTCCG<br>CAGTCTATTTCTGTGCAAGA |
| CDR-H3 | 67 | TGGGGTATTGGTAACTACGTGGGGTTTCCTTAC |
| FR4 | 68 | TGGGGCCAAGGGACTCTGGTCACTGTCTCTGCA |
| Constant region | 69 | GCCAAAACAACACCCCCATCAGTCTATCCACTGGCCCC<br>TGGGTGTGGAGATACAACTGGTTCCTCCGTGACTCTGG<br>GATGCCTGGTCAAGGGCTACTTCCCTGAGTCAGTGACT<br>GTGACTTGGAACTCTGGATCCCTGTCCAGCAGTGTGCA<br>CACCTTCCCAGCTCTCCTGCAGTCTGGACTCTACACTA<br>TGAGCAGCTCAGTGACTGTCCCCTCCAGCACCTGGCC<br>AAGTCAGACCGTCACCTGCAGCGTTGCTCACCCAGCC<br>AGCAGCACCACGGTGGACAAAAAACTTGAGCCCAGCG<br>GGCCCATTTCAACAATCAACCCCTGTCCTCCATGCAAG<br>GAGTGTCACAAATGCCCAGCTCCTAACCTCGAGGGTG<br>GACCATCCGTCTTCATCTTCCCTCCAAATATCAAGGATG<br>TACTCATGATCTCCCTGACACCCAAGGTCACGTGTGTG<br>GTGGTGGATGTGAGCGAGGATGACCCAGACGTCCAGA<br>TCAGCTGGTTTGTGAACAACGTGGAAGTACACACAGCT<br>CAGACACAAACCCATAGAGAGGATTACAACAGTACTAT<br>CCGGGTGGTCAGCACCCTCCCCATCCAGCACCAGGAC<br>TGGATGAGTGGCAAGGAGTTCAAATGCAAGGTCAACAA<br>CAAAGACCTCCCATCACCCATCGAGAGAACCATCTCAA<br>AAATTAAAGGGCTAGTCAGAGCTCCACAAGTATACATC<br>TTGCCGCCACCAGCAGAGCAGTTGTCCAGGAAAGATG<br>TCAGTCTCACTTGCCTGGTCGTGGGCTTCAACCCTGGA<br>GACATCAGTGTGGAGTGGACCAGCAATGGGCATACAG<br>AGGAGAACTACAAGGACACCGCACCAGTCCTGGACTC |

TABLE 3-continued

| 3H9 Sequences | | |
|---|---|---|
| | | TGACGGTTCTTACTTCATATATAGCAAGCTCAATATGAA AACAAGCAAGTGGGAGAAAACAGATTCCTTCTCATGCA ACGTGAGACACGAGGGTCTGAAAAATTACTACCTGAAG AAGACCATCTCCCGGTCTCCGGGTAAA |
| 3H9 Light chain-nucleic acid sequence | | |
| | SEQ ID NO: | |
| Leader sequence | 70 | ATGAAGTCACAGACCCAGGTCTTCGTATTTCTACTGCT CTGTGTGTCTGGTGTTCATGGG |
| FR1 | 71 | AGTATTGTGATGACCCAGACTCCCAAATTCCTGCTTGTA TCAGCAGGAGACAGGGTTACCATGACCTGC |
| CDR-L1 | 72 | AAGGCCAGTCTGAGTGTGAATAATGATGTAGCT |
| FR2 | 73 | TGGTACCAACAGAAGCCAGGGCAGTCTCCTAAACTACT GATATCC |
| CDR-L2 | 74 | TATGCATCCAGTCGCTACACT |
| FR3 | 75 | GGAGTCCCTGATCGCTTCACTGGCAGTGGATATGGGA CGGATTTCACTTTCACCATCAGCTCTGTGCAGGCTGAA GACCTGGCAGTTTATTTCTGT |
| CDR-L3 | 76 | CAGCAGGATTATAGCTCTCCGCTCACG |
| FR4 | 77 | TTCGGTGCTGGGACCAAGCTGGAGCTGAAA |
| Constant region | 78 | CGGGCTGATGCTGCACCAACTGTATCCATCTTCCCACC ATCCAGTGAGCAGTTAACATCTGGAGGTGCCTCAGTCG TGTGCTTCTTGAACAACTTCTACCCCAAAGACATCAATG TCAAGTGGAAGATTGATGGCAGTGAACGACAAAATGGC GTCCTGAACAGTTGGACTGATCAGGACAGCAAAGACAG CACCTACAGCATGAGCAGCACCCTCACGTTGACCAAG GACGAGTATGAACGACATAACAGCTATACCTGTGAGGC CACTCACAAGACATCAACTTCACCCATTGTCAAGAGCTT CAACAGGAATGAGTGT |
| 3H9 Heavy chain: Amino acid sequence (475 aa) Leader sequence-FR1-CDR1-FR2-CDR2-FR3-CDR3-FR4-Constant region | 79 | MGWSWIFLFLLSGTAGVLSEVQLQQSGPELVKSGASVKIS CKTSGYTFTEYTIHWVKQSHGESLEWVGGINPKNGGISY NQKFKGKATLTVDKSSSTAYMELRSLTSEDSAVYFCARW GIGNYVGFPYWGQGTLVTVSAAKTTPPSVYPLAPGCGDT TGSSVTLGCLVKGYFPESVTVTWNSGSLSSSVHTFPALL QSGLYTMSSSVTVPSSTWPSQTVTCSVAHPASSTTVDKK LEPSGPISTINPCPPCKECHKCPAPNLEGGPSVFIFPPNIK DVLMISLTPKVTCVVVDVSEDDPDVQISWFVNNVEVHTAQ TQTHREDYNSTIRVVSTLPIQHQDWMSGKEFKCKVNNKD LPSPIERTISKIKGLVRAPQVYILPPPAEQLSRKDVSLTCLV VGFNPGDISVEWTSNGHTEENYKDTAPVLDSDGSYFIYSK LNMKTSKWEKTDSFSCNVRHEGLKNYYLKKTISRSPGK |
| 3H9 Heavy chain variable region: Amino acid sequence FR1-CDR1-FR2-CDR2-FR3-CDR3-FR4 | 80 | EVQLQQSGPELVKSGASVKISCKTSGYTFTEYTIHWVKQS HGESLEWVGGINPKNGGISYNQKFKGKATLTVDKSSSTA YMELRSLTSEDSAVYFCARWGIGNYVGFPYWGQGTLVTV SA |
| 3H9 Light chain: Amino acid sequence (234 aa) Leader sequence-FR1-CDR1-FR2-CDR2-FR3-CDR3-FR4-Constant region | 81 | MKSQTQVFVFLLLCVSGVHGSIVMTQTPKFLLVSAGDRVT MTCKASLSVNNDVAWYQQKPGQSPKLLISYASSRYTGVP DRFTGSGYGTDFTFTISSVQAEDLAVYFCQQDYSSPLTFG AGTKLELKRADAAPTVSIFPPSSEQLTSGGASVVCFLNNF YPKDINVKWKIDGSERQNGVLNSWTDQDSKDSTYSMSST LTLTKDEYERHNSYTCEATHKTSTSPIVKSFNRNEC |
| 3H9 Light chain variable region: Amino acid sequence FR1-CDR1-FR2- | 82 | SIVMTQTPKFLLVSAGDRVTMTCKASLSVNNDVAWYQQK PGQSPKLLISYASSRYTGVPDRFTGSGYGTDFTFTISSVQ AEDLAVYFCQQDYSSPLTFGAGTKLELK |

TABLE 3-continued

| 3H9 Sequences | | |
|---|---|---|
| CDR2-FR3-CDR3-<br>FR4 | | |
| 3H9 Heavy chain:<br>DNA sequence<br>(1428 bp)<br>Leader sequence-<br>FR1-CDR1-FR2-<br>CDR2-FR3-CDR3-<br>FR4-Constant<br>region-Stop codon | 83 | ATGGGATGGAGCTGGATCTTTCTCTTTCTCCTGTCAGG<br>AACTGCAGGTGTCCTCTCTGAGGTCCAGCTGCAACAGT<br>CTGGACCTGAGCTGGTGAAGTCTGGGGCTTCAGTGAA<br>GATATCCTGCAAGACCTCTGGATACACTTTCACTGAATA<br>CACCATACACTGGGTGAAGCAGAGCCATGGAGAGAGC<br>CTTGAGTGGGTTGGAGGTATTAATCCTAAAAATGGTGG<br>TATTAGTTACAACCAGAAGTTCAAGGGCAAGGCCACAT<br>TGACTGTAGACAAGTCCTCCAGCACAGCCTACATGGAG<br>CTCCGCAGCCTGACATCTGAGGATTCCGCAGTCTATTT<br>CTGTGCAAGATGGGGTATTGGTAACTACGTGGGGTTTC<br>CTTACTGGGGCCAAGGGACTCTGGTCACTGTCTCTGCA<br>GCCAAAACAACACCCCCATCAGTCTATCCACTGGCCCC<br>TGGGTGTGGAGATACAACTGGTTCCTCCGTGACTCTGG<br>GATGCCTGGTCAAGGGCTACTTCCCTGAGTCAGTGACT<br>GTGACTTGGAACTCTGGATCCCTGTCCAGCAGTGTGCA<br>CACCTTCCCAGCTCTCCTGCAGTCTGGACTCTACACTA<br>TGAGCAGCTCAGTGACTGTCCCCTCCAGCACCTGGCC<br>AAGTCAGACCGTCACCTGCAGCGTTGCTCACCCAGCC<br>AGCAGCACCACGGTGGACAAAAAACTTGAGCCCAGCG<br>GGCCCATTTCAACAATCAACCCCTGTCCTCCATGCAAG<br>GAGTGTCACAAATGCCCAGCTCCTAACCTCGAGGGTG<br>GACCATCCGTCTTCATCTTCCCTCCAAATATCAAGGATG<br>TACTCATGATCTCCCTGACACCCAAGGTCACGTGTGTG<br>GTGGTGGATGTGAGCGAGGATGACCCAGACGTCCAGA<br>TCAGCTGGTTTGTGAACAACGTGGAAGTACACACAGCT<br>CAGACACAAACCCATAGAGAGGATTACAACAGTACTAT<br>CCGGGTGGTCAGCACCCTCCCCATCCAGCACCAGGAC<br>TGGATGAGTGGCAAGGAGTTCAAATGCAAGGTCAACAA<br>CAAAGACCTCCCATCACCCATCGAGAGAACCATCTCAA<br>AAATTAAAGGGCTAGTCAGAGCTCCACAAGTATACATC<br>TTGCCGCCACCAGCAGAGCAGTTGTCCAGGAAAGATG<br>TCAGTCTCACTTGCCTGGTCGTGGGCTTCAACCCTGGA<br>GACATCAGTGTGGAGTGGACCAGCAATGGGCATACAG<br>AGGAGAACTACAAGGACACCGCACCAGTCCTGGACTC<br>TGACGGTTCTTACTTCATATATAGCAAGCTCAATATGAA<br>AACAAGCAAGTGGGAGAAAACAGATTCCTTCTCATGCA<br>ACGTGAGACACGAGGGTCTGAAAAATTACTACCTGAAG<br>AAGACCATCTCCCGGTCTCCGGGTAAATGA |
| 3H9 Light chain:<br>DNA sequence<br>(705 bp)<br>Leader sequence-<br>FR1-CDR1-FR2-<br>CDR2-FR3-CDR3-<br>FR4-Constant<br>region-Stop codon | 84 | ATGAAGTCACAGACCCAGGTCTTCGTATTTCTACTGCT<br>CTGTGTGTCTGGTGTTCATGGGAGTATTGTGATGACCC<br>AGACTCCCAAATTCCTGCTTGTATCAGCAGGAGACAGG<br>GTTACCATGACCTGCAAGGCCAGTCTGAGTGTGAATAA<br>TGATGTAGCTTGGTACCAACAGAAGCCAGGGCAGTCTC<br>CTAAACTACTGATATCCTATGCATCCAGTCGCTACACTG<br>GAGTCCCTGATCGCTTCACTGGCAGTGGATATGGGAC<br>GGATTTCACTTTCACCATCAGCTCTGTGCAGGCTGAAG<br>ACCTGGCAGTTTATTTCTGTCAGCAGGATTATAGCTCTC<br>CGCTCACGTTCGGTGCTGGGACCAAGCTGGAGCTGAA<br>ACGGGCTGATGCTGCACCAACTGTATCCATCTTCCCAC<br>CATCCAGTGAGCAGTTAACATCTGGAGGTGCCTCAGTC<br>GTGTGCTTCTTGAACAACTTCTACCCCAAAGACATCAAT<br>GTCAAGTGGAAGATTGATGGCAGTGAACGACAAAATGG<br>CGTCCTGAACAGTTGGACTGATCAGGACAGCAAAGACA<br>GCACCTACAGCATGAGCAGCACCCTCACGTTGACCAA<br>GGACGAGTATGAACGACATAACAGCTATACCTGTGAGG<br>CCACTCACAAGACATCAACTTCACCCATTGTCAAGAGC<br>TTCAACAGGAATGAGTGTTAG |

TABLE 4

| 2A5 Sequences | | |
|---|---|---|
| 2A5 Heavy chain-amino acid sequence | | |
| | SEQ ID NO: | |
| Leader sequence | 85 | MGWSWVFLFLLSVTAGVHS |
| FR1 | 86 | QVQLQQSGAELVKPGASVKLSCKASGYTFT |

TABLE 4-continued

| 2A5 Sequences | | |
|---|---|---|
| CDR-H1 | 87 | **SYDIN** |
| FR2 | 88 | WVRQRPEQGLEWIG |
| CDR-H2 | 89 | **WIFPGDGSSRYNEKFKG** |
| FR3 | 90 | KATLTTDKSSSTAYMHLSRLTSEDSAVYFCAR |
| CDR-H3 | 91 | **GVYYGNSDS** |
| FR4 | 92 | WGQGTTLTVSS |
| Constant region | 93 | AKTTPPSVYPLAPGSAAQTNSMVTLGCLVKGYFPEPVTV TWNSGSLSSGVHTFPAVLQSDLYTLSSSVTVPSSTWPS ETVTCNVAHPASSTKVDKKIVPRDCGCKPCICTVPEVSS VFIFPPKPKDVLTITLTPKVTCVVVDISKDDPEVQFSWFVD DVEVHTAQTQPREEQFNSTFRSVSELPIMHQDWLNGKE FKCRVNSAAFPAPIEKTISKTKGRPKAPQVYTIPPPKEQM AKDKVSLTCMITDFFPEDITVEWQWNGQPAENYKNTQPI MDTDGSYFVYSKLNVQKSNWEAGNTFTCSVLHEGLHNH HTEKSLSHSPGK |

| 2A5 Light chain-amino acid sequence | | |
|---|---|---|
| | SEQ ID NO: | |
| Leader sequence | 94 | MDSQAQVLMLLLLWVSGTCG |
| FR1 | 95 | DIVMSQSPSSLAVSVGEKVTMGC |
| CDR-L1 | 96 | **KSSQSLLYSSNQKNFLA** |
| FR2 | 97 | YQQKPGQSPKLLIY |
| CDR-L2 | 98 | **WASTRES** |
| FR3 | 99 | GVPDRFTGSGSGTDFTLTISGVKAEDLAVYYC |
| CDR-L3 | 100 | **QQYYSYPYT** |
| FR4 | 101 | FGGGTKLEIK |
| Constant region | 102 | RADAAPTVSIFPPSSEQLTSGGASVVCFLNNFYPKDINVK WKIDGSERQNGVLNSWTDQDSKDSTYSMSSTLTLTKDE YERHNSYTCEATHKTSTSPIVKSFNRNEC |

| 2A5 Heavy chain-nucleic acid sequence | | |
|---|---|---|
| | SEQ ID NO: | |
| Leader sequence | 103 | ATGGGATGGAGCTGGGTCTTTCTCTTCCTCCTGTCAG TAACTGCAGGTGTCCACTCC |
| FR1 | 104 | CAGGTTCAGCTGCAGCAGTCTGGAGCTGAACTGGTGA AGCCTGGGGCTTCAGTGAAGTTGTCCTGCAAGGCTTC TGGCTACACCTTCACA |
| CDR-H1 | 105 | **AGCTATGATATAAAC** |
| FR2 | 106 | TGGGTGAGGCAGAGGCCTGAACAGGGACTTGAGTGG ATTGGA |
| CDR-H2 | 107 | **TGGATTTTTCCTGGAGATGGTAGTTCTAGGTACAATG AGAAGTTCAAGGGC** |
| FR3 | 108 | AAGGCCACGCTGACTACAGACAAATCCTCCAGCACAG CCTACATGCATCTCAGCAGGCTGACATCTGAGGACTC TGCTGTCTATTTCTGTGCAAGA |
| CDR-H3 | 109 | **GGGGTTTACTATGGTAACTCTGACTCC** |
| FR4 | 110 | TGGGGCCAAGGCACCACTCTCACAGTCTCCTCA |

TABLE 4-continued

| 2A5 Sequences | | |
|---|---|---|
| Constant region | 111 | GCCAAAACGACACCCCCATCTGTCTATCCACTGGCCC CTGGATCTGCTGCCCAAACTAACTCCATGGTGACCCT GGGATGCCTGGTCAAGGGCTATTTCCCTGAGCCAGTG ACAGTGACCTGGAACTCTGGATCCCTGTCCAGCGGTG TGCACACCTTCCCAGCTGTCCTGCAGTCTGACCTCTA CACTCTGAGCAGCTCAGTGACTGTCCCCTCCAGCACC TGGCCCAGCGAGACCGTCACCTGCAACGTTGCCCAC CCGGCCAGCAGCACCAAGGTGGACAAGAAAATTGTGC CCAGGGATTGTGGTTGTAAGCCTTGCATATGTACAGT CCCAGAAGTATCATCTGTCTTCATCTTCCCCCCAAAGC CCAAGGATGTGCTCACCATTACTCTGACTCCTAAGGTC ACGTGTGTTGTGGTAGACATCAGCAAGGATGATCCCG AGGTCCAGTTCAGCTGGTTTGTAGATGATGTGGAGGT GCACACAGCTCAGACGCAACCCCGGGAGGAGCAGTT CAACAGCACTTTCCGCTCAGTCAGTGAACTTCCCATCA TGCACCAGGACTGGCTCAATGGCAAGGAGTTCAAATG CAGGGTCAACAGTGCAGCTTTCCCTGCCCCCATCGAG AAAACCATCTCCAAAACCAAAGGCAGACCGAAGGCTC CACAGGTGTACACCATTCCACCTCCCAAGGAGCAGAT GGCCAAGGATAAAGTCAGTCTGACCTGCATGATAACA GACTTCTTCCCTGAAGACATTACTGTGGAGTGGCAGT GGAATGGGCAGCCAGCGGAGAACTACAAGAACACTCA GCCCATCATGGACACAGATGGCTCTTACTTCGTCTACA GCAAGCTCAATGTGCAGAAGAGCAACTGGGAGGCAG GAAATACTTTCACCTGCTCTGTGTTACATGAGGGCCTG CACAACCACCATACTGAGAAGAGCCTCTCCCACTCTC CTGGTAAA |

| 2A5 Light chain-nucleic acid sequence | | |
|---|---|---|
| | SEQ ID NO: | |
| Leader sequence | 112 | ATGGATTCACAGGCCCAGGTTCTTATGTTACTGCTGCT ATGGGTATCTGGTACCTGTGGG |
| FR1 | 113 | GACATTGGATGTCACAGTCTCCATCCTCCCTAGCTGT GTCAGTTGGAGAGAAGGTTACTATGGGCTGC |
| CDR-L1 | 114 | **AAGTCCAGTCAGAGCCTTTTATACAGTAGCAATCAAA AGAACTTCTTGGCC** |
| FR2 | 115 | TGGTACCAGCAGAAACCAGGGCAGTCTCCTAAACTGC TGATTTAC |
| CDR-L2 | 116 | **TGGGCATCCACGAGGGAATCT** |
| FR3 | 117 | GGGGTCCCTGATCGCTTCACAGGCAGTGGATCTGGG ACAGATTTCACTCTCACCATCAGCGGTGTGAAGGCTG AAGACCTGGCAGTTTATTACTGT |
| CDR-L3 | 118 | CAGCAATATTATAGCTATCCGTACACG |
| FR4 | 119 | TTCGGAGGGGGGACCAAGCTGGAAATAAAA |
| Constant region | 120 | CGGGCTGATGCTGCACCAACTGTATCCATCTTCCCAC CATCCAGTGAGCAGTTAACATCTGGAGGTGCCTCAGT CGTGTGCTTCTTGAACAACTTCTACCCCAAAGACATCA ATGTCAAGTGGAAGATTGATGGCAGTGAACGACAAAA TGGCGTCCTGAACAGTTGGACTGATCAGGACAGCAAA GACAGCACCTACAGCATGAGCAGCACCCTCACGTTGA CCAAGGACGAGTATGAACGACATAACAGCTATACCTG TGAGGCCACTCACAAGACATCAACTTCACCCATTGTCA AGAGCTTCAACAGGAATGAGTGT |
| 2A5 Heavy chain: Amino acid sequence (461 aa) Leader sequence-FR1-CDR1-FR2-CDR2-FR3-CDR3-FR4-Constant region- | 121 | MGWSWVFLFLLSVTAGVHSQVQLQQSGAELVKPGASV KLSCKASGYTFTSYDINWVRQRPEQGLEWIGWIFPGDG SSRYNEKFKGKATLTTDKSSSTAYMHLSRLTSEDSAVYF CARGVYYGNSDSWGQGTTLTVSSAKTTPPSVYPLAPGS AAQTNSMVTLGCLVKGYFPEPVTVTWNSGSLSSGVHTF PAVLQSDLYTLSSSVTVPSSTWPSETVTCNVAHPASSTK VDKKIVPRDCGCKPCICTVPEVSSVFIFPPKPKDVLTITLT PKVTCVVVDISKDDPEVQFSWFVDDVEVHTAQTQPREE QFNSTFRSVSELPIMHQDWLNGKEFKCRVNSAAFPAPIE KTISKTKGRPKAPQVYTIPPPKEQMAKDKVSLTCMITDFF PEDITVEWQWNGQPAENYKNTQPIMDTDGSYFVYSKLN VQKSNWEAGNTFTCSVLHEGLHNHHTEKSLSHSPGK |

TABLE 4-continued

| 2A5 Sequences | | |
|---|---|---|
| 2A5 Heavy chain variable region: Amino acid sequence FR1-CDR1-FR2-CDR2-FR3-CDR3-FR4 | 122 | MGWSWVFLFLLSVTAGVHSQVQLQQSGAELVKPGASV<br>KLSCKASGYTFTSYDINWVRQRPEQGLEWIGWIFPGDG<br>SSRYNEKFKGKATLTTDKSSSTAYMHLSRLTSEDSAVYF<br>CARGVYYGNSDSWGQGTTLTVSS |
| 2A5 Light chain: Amino acid sequence (240 aa) Leader sequence-FR1-CDR1-FR2-CDR2-FR3-CDR3-FR4-Constant region | 123 | MDSQAQVLMLLLLWVSGTCGDIVMSQSPSSLAVSVGEK<br>VTMGCKSSQSLLYSSNQKNFLAWYQQKPGQSPKLLIYW<br>ASTRESGVPDRFTGSGSGTDFTLTISGVKAEDLAVYYCQ<br>QYYSYPYTFGGGTKLEIKRADAAPTVSIFPPSSEQLTSGG<br>ASVVCFLNNFYPKDINVKWKIDGSERQNGVLNSWTDQD<br>SKDSTYSMSSTLTLTKDEYERHNSYTCEATHKTSTSPIVK<br>SFNRNEC |
| 2A5 Light chain variable region: Amino acid sequence FR1-CDR1-FR2-CDR2-FR3-CDR3-FR4 | 124 | DIVMSQSPSSLAVSVGEKVTMGCKSSQSLLYSSNQKNFL<br>AWYQQKPGQSPKLLIYWASTRESGVPDRFTGSGSGTDF<br>TLTISGVKAEDLAVYYCQQYYSYPYTFGGGTKLEIK |
| 2A5 Heavy chain: DNA sequence (1386 bp) Leader sequence-FR1-CDR1-FR2-CDR2-FR3-CDR3-FR4-Constant region-Stop codon | 125 | ATGGGATGGAGCTGGGTCTTTCTCTTCCTCCTGTCAG<br>TAACTGCAGGTGTCCACTCCCAGGTTCAGCTGCAGCA<br>GTCTGGAGCTGAACTGGTGAAGCCTGGGGCTTCAGTG<br>AAGTTGTCCTGCAAGGCTTCTGGCTACACCTTCACAA<br>GCTATGATATAAACTGGGTGAGGCAGAGGCCTGAACA<br>GGGACTTGAGTGGATTGGATGGATTTTTCCTGGAGAT<br>GGTAGTTCTAGGTACAATGAGAAGTTCAAGGGCAAGG<br>CCACGCTGACTACAGACAAATCCTCCAGCACAGCCTA<br>CATGCATCTCAGCAGGCTGACATCTGAGGACTCTGCT<br>GTCTATTTCTGTGCAAGAGGGGTTTACTATGGTAACTC<br>TGACTCCTGGGGCCAAGGCACCACTCTCACAGTCTCC<br>TCAGCCAAAACGACACCCCCATCTGTCTATCCACTGG<br>CCCCTGGATCTGCTGCCCAAACTAACTCCATGGTGAC<br>CCTGGGATGCCTGGTCAAGGGCTATTTCCCTGAGCCA<br>GTGACAGTGACCTGGAACTCTGGATCCCTGTCCAGCG<br>GTGTGCACACCTTCCCAGCTGTCCTGCAGTCTGACCT<br>CTACACTCTGAGCAGCTCAGTGACTGTCCCCTCCAGC<br>ACCTGGCCCAGCGAGACCGTCACCTGCAACGTTGCC<br>CACCCGGCCAGCAGCACCAAGGTGGACAAGAAAATTG<br>TGCCCAGGGATTGTGGTTGTAAGCCTTGCATATGTAC<br>AGTCCCAGAAGTATCATCTGTCTTCATCTTCCCCCCAA<br>AGCCCAAGGATGTGCTCACCATTACTCTGACTCCTAA<br>GGTCACGTGTGTTGTGGTAGACATCAGCAAGGATGAT<br>CCCGAGGTCCAGTTCAGCTGGTTTGTAGATGATGTGG<br>AGGTGCACACAGCTCAGACGCAACCCCGGGAGGAGC<br>AGTTCAACAGCACTTTCCGCTCAGTCAGTGAACTTCCC<br>ATCATGCACCAGGACTGGCTCAATGGCAAGGAGTTCA<br>AATGCAGGGTCAACAGTGCAGCTTTCCCTGCCCCCAT<br>CGAGAAAACCATCTCCAAAACCAAAGGCAGACCGAAG<br>GCTCCACAGGTGTACACCATTCCACCTCCCAAGGAGC<br>AGATGGCCAAGGATAAAGTCAGTCTGACCTGCATGAT<br>AACAGACTTCTTCCCTGAAGACATTACTGTGGAGTGG<br>CAGTGGAATGGGCAGCCAGCGGAGAACTACAAGAAC<br>ACTCAGCCCATCATGGACACAGATGGCTCTTACTTCGT<br>CTACAGCAAGCTCAATGTGCAGAAGAGCAACTGGGAG<br>GCAGGAAATACTTTCACCTGCTCTGTGTTACATGAGG<br>GCCTGCACAACCACCATACTGAGAAGAGCCTCTCCCA<br>CTCTCCTGGTAAATGA |
| 2A5 Light chain: DNA sequence (723 bp) Leader sequence-FR1-CDR1-FR2-CDR2-FR3-CDR3-FR4-Constant region-Stop codon | 126 | ATGGATTCACAGGCCCAGGTTCTTATGTTACTGCTGCT<br>ATGGGTATCTGGTACCTGTGGGGACATTGTGATGTCA<br>CAGTCTCCATCCTCCCTAGCTGTGTCAGTTGGAGAGA<br>AGGTTACTATGGGCTGCAAGTCCAGTCAGAGCCTTTT<br>ATACAGTAGCAATCAAAAGAACTTCTTGGCCTGGTACC<br>AGCAGAAACCAGGGCAGTCTCCTAAACTGCTGATTTA<br>CTGGGCATCCACGAGGGAATCTGGGGTCCCTGATCG<br>CTTCACAGGCAGTGGATCTGGGACAGATTTCACTCTC<br>ACCATCAGCGGTGTGAAGGCTGAAGACCTGGCAGTTT<br>ATTACTGTCAGCAATATTATAGCTATCCGTACACGTTC<br>GGAGGGGGGACCAAGCTGGAAATAAAACGGGCTGAT<br>GCTGCACCAACTGTATCCATCTTCCCACCATCCAGTGA |

TABLE 4-continued

| 2A5 Sequences |
|---|
| GCAGTTAACATCTGGAGGTGCCTCAGTCGTGTGCTTC<br>TTGAACAACTTCTACCCCAAAGACATCAATGTCAAGTG<br>GAAGATTGATGGCAGTGAACGACAAAATGGCGTCCTG<br>AACAGTTGGACTGATCAGGACAGCAAAGACAGCACCT<br>ACAGCATGAGCAGCACCCTCACGTTGACCAAGGACGA<br>GTATGAACGACATAACAGCTATACCTGTGAGGCCACT<br>CACAAGACATCAACTTCACCCATTGTCAAGAGCTTCAA<br>CAGGAATGAGTGTTAG |

Example 2

Melanoma Cancer Experiments:

Methodology:

The B16 mouse melanoma cell line was propagated in Dulbecco's modified essential media (DMEM) which was supplemented with 10% fetal bovine serum (FBS) and L glutamine and penicillin streptomycin. $10^4$ cells were injected subcutaneously into C57BL/6J, fgl2−/− or fgl2Tg/Tg mice (n=5/group). Mice were monitored for up to 30 days and tumor size and mouse survival were determined.

Results:

Tumors grew much more rapidly and to a greater volume in mice deficient in fgl2 (fgl2−/−) and fgl2 Tg/Tg in comparison to wild type C57BL/6J (FIG. 19). The fgl2−/− mice were devoid of both membrane bound fgl2 prothrombinase largely expressed by the cells of the reticulo-endothelial system whereas transgenic mice (fg2Tg/Tg) lacked the prothrombinase fgl2 but expressed soluble fgl2.

CONCLUSIONS

This data shows that the innate fgl2 is critical for anti tumor activity. This is based on the findings in both the fgl2−/− and fgl2Tg/Tg both of which lack fgl2 prothrombinase. It is known that melanoma produces fgl2 secondary to gene duplication which would account for increased levels of fgl2 in the fgl2−/− mouse.

One of the advantages of antibody 9D8 is that it targets the adaptive immune FGL2 and tumor FGL2 but does not disrupt the innate (macrophage and DC) FGL2. Here it is shown that disruption of innate FGL2 leads to more rapid growth of tumor and metastasis. This is consistent with previous data showing the effect of disruption of FGL2 in viral infection which was associated with increased viral replication. Innate FGL2 leads to production of thrombin and fibrin which is a first line defense against tumors and viruses.

REFERENCES

1. Mantovani A, Allavena P, Sica A, Balkwill F. 2008. Cancer-related inflammation. Nature 454:436-444.
2. Karin M, Greten F R. 2005. N F-kappaB: linking inflammation and immunity to cancer development and progression. Nat Rev Immunol 5:749-759.
3. Curtin J F, Candolfi M, Fakhouri T M, Liu C, Alden A, Edwards M, Lowenstein P R, Castro M G. 2008. Treg depletion inhibits efficacy of cancer immunotherapy: implications for clinical trials. PLoS One 3:0001983.
4. Sica A, Schioppa T, Mantovani A, Allavena P. 2006. Tumour-associated macrophages are a distinct M2 polarised population promoting tumour progression: potential targets of anti-cancer therapy. Eur J Cancer 42:717-727.
5. Watanabe S, Deguchi K, Zheng R, Tamai H, Wang L X, Cohen P A, Shu S. 2008. Tumor-induced CD11b+Gr-1+ myeloid cells suppress T cell sensitization in tumor-draining lymph nodes. J Immunol 181:3291-3300.
6. Care M A, Westhead D R, Tooze R M. 2015. Gene expression meta-analysis reveals immune response convergence on the IFNgamma-STAT1-IRF1 axis and adaptive immune resistance mechanisms in lymphoma. Genome Med 7:015-0218.
7. Twyman-Saint Victor C, Rech A J, Maity A, Rengan R, Pauken K E, Stelekati E, Benci J L, Xu B, Dada H, Odorizzi P M, Herati R S, Mansfield K D, Patsch D, Amaravadi R K, Schuchter L M, Ishwaran H, Mick R, Pryma D A, Xu X, Feldman M D, Gangadhar T C, Hahn S M, Wherry E J, Vonderheide R H, Minn A J. 2015. Radiation and dual checkpoint blockade activate non-redundant immune mechanisms in cancer. Nature 520:373-377.
8. Colegio O R, Chu N-Q, Szabo A L, Chu T, Rhebergen A M, Jairam V, Cyrus N, Brokowski C E, Eisenbarth S C, Phillips G M, Cline G W, Phillips A J, Medzhitov R. 2014. Functional polarization of tumour-associated macrophages by tumour-derived lactic acid. Nature 513:559-563.
9. Cui T X, Kryczek I, Zhao L, Zhao E, Kuick R, Roh M H, Vatan L, Szeliga W, Mao Y, Thomas D G, Kotarski J, Tarkowski R, Wicha M, Cho K, Giordano T, Liu R, Zou W. 2013. Myeloid-derived suppressor cells enhance stemness of cancer cells by inducing microRNA101 and suppressing the corepressor CtBP2. Immunity 39:611-621.
10. Wilcox R A, Feldman A L, Wada D A, Yang Z-Z, Comfere N I, Dong H, Kwon E D, Novak A J, Markovic S N, Pittelkow M R, Witzig T E, Ansell S M. 2009. B7-H1 (PD-L1, CD274) suppresses host immunity in T-cell lymphoproliferative disorders. Blood 114:2149-2158.
11. McClanahan F, Hanna B, Miller S, Clear A J, Lichter P, Gribben J G, Seiffert M. 2015. PD-L1 checkpoint blockade prevents immune dysfunction and leukemia development in a mouse model of chronic lymphocytic leukemia. Blood 126:203-211.
12. Ohaegbulam K C, Assal A, Lazar-Molnar E, Yao Y, Zang X. 2015. Human cancer immunotherapy with antibodies to the PD-1 and PD-L1 pathway. Trends Mol Med 21:24-33.
13. Van Overmeire E, Stijlemans B, Heymann F, Keirsse J, Morias Y, Elkrim Y, Brys L, Abels C, Lahmar Q, Ergen C, Vereecke L, Tacke F, De Baetselier P, Van Ginderachter J A, Laoui D. 2015. M-CSF and GM-CSF receptor signaling differentially regulate monocyte maturation and macrophage polarization in the tumor microenvironment. Cancer Res doi:10.1158/0008-5472.can-15-0869.
14. Lewis C E, Pollard J W. 2006. Distinct role of macrophages in different tumor microenvironments. Cancer Res 66:605-612.

15. Butt A Q, Mills K H G. 2014. Immunosuppressive networks and checkpoints controlling antitumor immunity and their blockade in the development of cancer immunotherapeutics and vaccines. Oncogene 33:4623-4631.
16. Tsai K K, Daud A I. 2015. Nivolumab plus ipilimumab in the treatment of advanced melanoma. J Hematol Oncol 8:015-0219.
17. Dang T O, Ogunniyi A, Barbee M S, Drilon A. 2015. Pembrolizumab for the treatment of PD-L1 positive advanced or metastatic non-small cell lung cancer. Expert Rev Anticancer Ther 20:20.
18. Joseph R W, Millis S Z, Carballido E M, Bryant D, Gatalica Z, Reddy S, Bryce A H, Vogelzang N J, Stanton M L, Castle E P, Ho T H. 2015. PD-1 and PD-L1 Expression in Renal Cell Carcinoma with Sarcomatoid Differentiation. Cancer Immunol Res 25:25.
19. Aoun F, Kourie H R, Sideris S, Roumeguere T, Velthoven R V, Gil T. 2015. Checkpoint inhibitors in bladder and renal cancers: results and perspectives. Immunotherapy 23:23.
20. Li J, Jie H-B, Lei Y, Gildener-Leapman N, Trivedi S, Green T, Kane L P, Ferris R L. 2015. PD-1/SHP-2 inhibits Tc1/Th1 phenotypic responses and the activation of T cells in the tumor microenvironment. Cancer Res 75:508-518.
21. Ramsay A G, Johnson A J, Lee A M, Gorgün G, Le Dieu R, Blum W, Byrd J C, Gribben J G. 2008. Chronic lymphocytic leukemia T cells show impaired immunological synapse formation that can be reversed with an immunomodulating drug. J Clin Invest 118:2427-2437.
22. Sharma M D, Baban B, Chandler P, Hou D-Y, Singh N, Yagita H, Azuma M, Blazar B R, Mellor A L, Munn D H. 2007. Plasmacytoid dendritic cells from mouse tumor-draining lymph nodes directly activate mature Tregs via indoleamine 2,3-dioxygenase. J Clin Invest 117:2570-2582.
23. Chen D S, Mellman I. 2013. Oncology meets immunology: the cancer-immunity cycle. Immunity 39:1-10.
24. Sakuishi K, Apetoh L, Sullivan J M, Blazar B R, Kuchroo V K, Anderson A C. 2010. Targeting Tim-3 and PD-1 pathways to reverse T cell exhaustion and restore anti-tumor immunity. J Exp Med 207:2187-2194.
25. Johnston R J, Comps-Agrar L, Hackney J, Yu X, Huseni M, Yang Y, Park S, Javinal V, Chiu H, Irving B, Eaton D L, Grogan J L. 2014. The immunoreceptor TIGIT regulates antitumor and antiviral CD8(+) T cell effector function. Cancer Cell 26:923-937.
26. Chauvin J-M, Pagliano O, Fourcade J, Sun Z, Wang H, Sander C, Kirkwood J M, Chen T-hT, Maurer M, Korman A J, Zarour H M. 2015. TIGIT and PD-1 impair tumor antigen-specific CD8+ T cells in melanoma patients. J Clin Invest 125:2046-2058.
27. Koyama T, Hall L R, Haser W G, Tonegawa S, Saito H. 1987. Structure of a cytotoxic T-lymphocyte-specific gene shows a strong homology to fibrinogen beta and gamma chains. Proc Natl Acad Sci USA 84:1609-1613.
28. Levy G A, Liu M, Ding J, Yuwaraj S, Leibowitz J, Marsden P A, Ning Q, Kovalinka A, Phillips M J. 2000. Molecular and functional analysis of the human prothrombinase gene (HFGL2) and its role in viral hepatitis. Am J Pathol 156:1217-1225.
29. Marazzi S, Blum S, Hartmann R, Gundersen D, Schreyer M, Argraves S, von Fliedner V, Pytela R, Ruegg C. 1998. Characterization of human fibroleukin, a fibrinogen-like protein secreted by T lymphocytes. J Immunol 161:138-147.
30. Ruegg C, Pytela R. 1995. Sequence of a human transcript expressed in T-lymphocytes and encoding a fibrinogen-like protein. Gene 160:257-262.
31. Hu J, Yan J, Rao G, Latha K, Overwijk W W, Heimberger A B, Li S. 2014. The Duality of Fgl2-Secreted Immune Checkpoint Regulator Versus Membrane-Associated Procoagulant: Therapeutic Potential and Implications. Int Rev Immunol 26:26.
32. Liu Y, Xu L, Zeng Q, Wang J, Wang M, Xi D, Wang X, Yang D, Luo X, Ning Q. 2012. Downregulation of FGL2/prothrombinase delays HCCLM6 xenograft tumour growth and decreases tumour angiogenesis. Liver Int 32:1585-1595.
33. Rabizadeh E, Cherny I, Wolach O, Sherman S, Binkovski N, Peretz A, Lederfein D, Inbal A. 2014. Increased activity of cell membrane-associated prothrombinase, fibrinogen-like protein 2, in peripheral blood mononuclear cells of B-cell lymphoma patients. PLoS One 9.
34. van Hinsbergh V W, Collen A, Koolwijk P. 2001. Role of fibrin matrix in angiogenesis. Ann N Y Acad Sci 936:426-437.
35. Li X L, Menoret S, Bezie S, Caron L, Chabannes D, Hill M, Halary F, Angin M, Heslan M, Usal C, Liang L, Guillonneau C, Le Mauff B, Cuturi M C, Josien R, Anegon I. 2010. Mechanism and localization of CD8 regulatory T cells in a heart transplant model of tolerance. J Immunol 185:823-833.
36. Shalev I, Liu H, Koscik C, Bartczak A, Javadi M, Wong K M, Maknojia A, He W, Liu M F, Diao J, Winter E, Manuel J, McCarthy D, Cattral M, Gommerman J, Clark D A, Phillips M J, Gorczynski R R, Zhang L, Downey G, Grant D, Cybulsky M I, Levy G. 2008. Targeted deletion of fgl2 leads to impaired regulatory T cell activity and development of autoimmune glomerulonephritis. Journal of Immunology 180:249-260.
37. Shalev I, Wong K M, Foerster K, Zhu Y, Chan C, Maknojia A, Zhang J, Ma X Z, Yang X C, Gao J F, Liu H, Selzner N, Clark D A, Adeyi O, Phillips M J, Gorczynski R R, Grant D, McGilvray I, Levy G. 2009. The novel CD4+CD25+ regulatory T cell effector molecule fibrinogen-like protein 2 contributes to the outcome of murine fulminant viral hepatitis. Hepatology 49:387-397.
38. Chan C W, Kay L S, Khadaroo R G, Chan M W, Lakatoo S, Young K J, Zhang L, Gorczynski R M, Cattral M, Rotstein O, Levy G A. 2003. Soluble fibrinogen-like protein 2/fibroleukin exhibits immunosuppressive properties: suppressing T cell proliferation and inhibiting maturation of bone marrow-derived dendritic cells. J Immunol 170:4036-4044.
39. Liu H, Shalev I, Manuel J, He W, Leung E, Crookshank J, Liu M F, Diao J, Cattral M, Clark D A, Isenman D E, Gorczynski R M, Grant D R, Zhang L, Phillips M J, Cybulsky M I, Levy G A. 2008. The FGL2-FcgammaRIIB pathway: a novel mechanism leading to immunosuppression. Eur J Immunol 38:3114-3126.
40. Liu H, Zhang L, Cybulsky M, Gorczynski R, Crookshank J, Manuel J, Grant D, Levy G. 2006. Identification of the receptor for FGL2 and implications for susceptibility to mouse hepatitis virus (MHV-3)-induced fulminant hepatitis. Advances in Experimental Medicine & Biology 581:421-425.
41. Joller N, Lozano E, Burkett P R, Patel B, Xiao S, Zhu C, Xia J, Tan T G, Sefik E, Yajnik V, Sharpe A H, Quintana F J, Mathis D, Benoist C, Hafler D A, Kuchroo V K. 2014. Treg cells expressing the coinhibitory molecule TIGIT selectively inhibit proinflammatory Th1 and Th17 cell responses. Immunity 40:569-581.

42. Zehn D, Wherry E J. 2015. Immune Memory and Exhaustion: Clinically Relevant Lessons from the LCMV Model. Adv Exp Med Biol 850:137-152.
43. Severson J J, Serracino H S, Mateescu V, Raeburn C D, McIntyre R C, Jr., Sams S B, Haugen B R, French J D. 2015. PD-1+Tim-3+ CD8+ T Lymphocytes Display Varied Degrees of Functional Exhaustion in Patients with Regionally Metastatic Differentiated Thyroid Cancer. Cancer Immunol Res 3:620-630.
44. Su K, Chen F, Yan W M, Zeng Q L, Xu L, Xi D, Pi B, Luo X P, Ning Q. 2008. Fibrinogen-like protein 2/fibroleukin prothrombinase contributes to tumor hypercoagulability via IL-2 and IFN-gamma. World J Gastroenterol 14:5980-5989.
45. Qin W Z, Li Q L, Chen W F, Xu M D, Zhang Y Q, Zhong Y S, Ma L L, Hu J W, Cai M Y, He M J, Yao L Q, Zhou P H. 2014. Overexpression of fibrinogen-like protein 2 induces epithelial-to-mesenchymal transition and promotes tumor progression in colorectal carcinoma. Med Oncol 31:014-0181.
46. Yan J, Kong L Y, Hu J, Gabrusiewicz K, Dibra D, Xia X, Heimberger A B, Li S. 2015. FGL2 as a Multimodality Regulator of Tumor-Mediated Immune Suppression and Therapeutic Target in Gliomas. J Natl Cancer Inst 107.
47. Zhu Y, Zhang L, Zha H, Yang F, Hu C, Chen L, Guo B, Zhu B. 2017. Stroma-derived Fibrinogen-like Protein 2 Activates Cancer-associated Fibroblasts to Promote Tumor Growth in Lung Cancer. Int J Biol Sci 13:804-814.
48. Curiel T J, Coukos G, Zou L, Alvarez X, Cheng P, Mottram P, Evdemon-Hogan M, Conejo-Garcia J R, Zhang L, Burow M, Zhu Y, Wei S, Kryczek I, Daniel B, Gordon A, Myers L, Lackner A, Disis M L, Knutson K L, Chen L, Zou W. 2004. Specific recruitment of regulatory T cells in ovarian carcinoma fosters immune privilege and predicts reduced survival. Nat Med 10:942-949.
49. Hamanishi J, Mandai M, Konishi I. 2016. Immune checkpoint inhibition in ovarian cancer. Int Immunol 28:339-348.
50. Hamanishi J, Mandai M, Matsumura N, Abiko K, Baba T, Konishi I. 2016. PD-1/PD-L1 blockade in cancer treatment: perspectives and issues. Int J Clin Oncol 21:462-473.
51. Latha T S, Panati K, Gowd D S, Reddy M C, Lomada D. 2014. Ovarian cancer biology and immunotherapy. Int Rev Immunol 33:428-440.
52. Pengetnze Y, Steed M, Roby K F, Terranova P F, Taylor C C. 2003. Src tyrosine kinase promotes survival and resistance to chemotherapeutics in a mouse ovarian cancer cell line. Biochem Biophys Res Commun 309:377-383.
53. McCloskey C W, Goldberg R L, Carter L E, Gamwell L F, A I-Hujaily E M, Collins O, Macdonald E A, Garson K, Daneshmand M, Carmona E, Vanderhyden B C. 2014. A new spontaneously transformed syngeneic model of high-grade serous ovarian cancer with a tumor-initiating cell population. Front Oncol 4:53.

The invention claimed is:

1. An antibody or binding fragment thereof that specifically binds FGL2 comprising:

a light chain variable region and a heavy chain variable region, the heavy chain variable region comprising complementarity determining regions CDR-H1, CDR-H2 and CDR-H3 and the light chain variable region comprising complementarity determining regions CDR-L1, CDR-L2 and CDR-L3, wherein (i) CDR-H1 comprises the amino acid sequence set out in SEQ ID No: 3, CDR-H2 comprises the amino acid sequence set out in SEQ ID No: 5; and CDR-H3 comprises the amino acid sequence set out in SEQ ID No: 7; and (ii) CDR-L1 comprises the amino acid sequence set out in SEQ ID No: 12, CDR-L2 comprises the amino acid sequence set out in SEQ ID No: 14; and CDR-L3 comprises the amino acid sequence set out in SEQ ID No: 16.

2. The antibody or binding fragment of claim 1, wherein the heavy chain variable region comprises the amino acid sequence of SEQ ID NO: 38 or an amino acid sequence having at least 70% sequence identity to the framework regions of SEQ ID NO: 38 and/or the light chain variable region comprises the amino acid sequence of SEQ ID NO: 40 or an amino acid sequence having at least 70% sequence identity to the framework regions of SEQ ID NO: 40.

3. The antibody or binding fragment of claim 1, wherein the antibody is a monoclonal antibody.

4. The antibody or binding fragment of claim 1 selected from the group consisting of an antigen-binding Fab, a single-chain Fv (scFv), a (svFv)2, a scFv-CH3, a scFv-Fc, a bispecific antibody, a phage-Fab and a phage-scFv.

5. The antibody or binding fragment of claim 1, wherein the antibody or antigen-binding fragment is an IgG molecule.

6. An immunoconjugate comprising (1) the antibody or binding fragment of claim 1 attached to (2) an effector agent.

7. The immunoconjugate of claim 6, wherein the effector agent is a detection agent, an anti-neoplastic agent or a toxin.

8. A composition comprising the antibody or binding fragment of claim 1 and a carrier.

9. A method of detecting a FGL2-expressing cell, the method comprising:

a) contacting a cell with the antibody or binding fragment of claim 1, under conditions to form an antibody:FGL2 complex; and b) detecting the antibody:FGL2 complex.

* * * * *

SEQUENCE LISTING

<160> NUMBER OF SEQ ID NOS: 126

<210> SEQ ID NO 1
<211> LENGTH: 19
<212> TYPE: PRT
<213> ORGANISM: Artificial Sequence
<220> FEATURE:
<223> OTHER INFORMATION: Synthetic construct

<400> SEQUENCE: 1

Met Lys Cys Ser Trp Val Ile Phe Phe Leu Met Ala Val Val Thr Gly
1 5 10 15

Val Asn Ser

<210> SEQ ID NO 2
<211> LENGTH: 30
<212> TYPE: PRT
<213> ORGANISM: Artificial Sequence
<220> FEATURE:
<223> OTHER INFORMATION: Synthetic construct

<400> SEQUENCE: 2

Glu Val Gln Leu Gln Gln Ser Gly Ala Glu Leu Val Lys Pro Gly Ala
1 5 10 15

Ser Val Gln Leu Ser Cys Thr Ala Ser Gly Phe Asn Ile Lys
20 25 30

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

-continued

```
Asp Thr Tyr Ile His
1               5


<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Trp Val Lys Gln Arg Pro Glu Gln Gly Leu Glu Trp Ile Gly
1               5                   10


<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

Arg Ile Asp Pro Glu Asp Gly Asn Thr Lys Tyr Asp Pro Lys Phe Gln
1               5                   10                  15

Ala


<210> SEQ ID NO 6
<211> LENGTH: 32
<212> TYPE: PRT
<213> ORGANISM: Artificial Sequence
<220> FEATURE:
<223> OTHER INFORMATION: Synthetic construct

<400> SEQUENCE: 6

Lys Ala Thr Ile Thr Ala Asp Thr Phe Ser Asn Thr Ala Tyr Leu Gln
1               5                   10                  15

Leu Ser Ser Leu Thr Ser Glu Asp Thr Ala Val Tyr Tyr Cys Ala Arg
            20                  25                  30


<210> SEQ ID NO 7
<211> LENGTH: 6
<212> TYPE: PRT
<213> ORGANISM: Artificial Sequence
<220> FEATURE:
<223> OTHER INFORMATION: Synthetic construct

<400> SEQUENCE: 7

Ser Tyr Gly Asn Ala Tyr
1               5


<210> SEQ ID NO 8
<211> LENGTH: 11
<212> TYPE: PRT
<213> ORGANISM: Artificial Sequence
<220> FEATURE:
<223> OTHER INFORMATION: Synthetic construct

<400> SEQUENCE: 8

Trp Gly Gln Gly Thr Leu Val Thr Val Ser Ala
1               5                   10


<210> SEQ ID NO 9
<211> LENGTH: 324
<212> TYPE: PRT
<213> ORGANISM: Artificial Sequence
```

<220> FEATURE:
<223> OTHER INFORMATION: Synthetic construct

<400> SEQUENCE: 9

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Pro Ser Ser Thr Trp Pro Ser Glu Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Gln Pro Arg Glu Glu Gln Phe Asn Ser Thr
165 170 175

Phe Arg Ser Val Ser Glu Leu Pro Ile Met His Gln Asp Trp Leu Asn
180 185 190

Gly Lys Glu Phe Lys Cys Arg Val Asn Ser Ala Ala Phe Pro Ala Pro
195 200 205

Ile Glu Lys Thr Ile Ser Lys Thr Lys Gly Arg Pro Lys Ala Pro Gln
210 215 220

Val Tyr Thr Ile Pro Pro Pro Lys Glu Gln Met Ala Lys Asp Lys Val
225 230 235 240

Ser Leu Thr Cys Met Ile Thr Asp Phe Phe Pro Glu Asp Ile Thr Val
245 250 255

Glu Trp Gln Trp Asn Gly Gln Pro Ala Glu Asn Tyr Lys Asn Thr Gln
260 265 270

Pro Ile Met Asp Thr Asp Gly Ser Tyr Phe Val Tyr Ser Lys Leu Asn
275 280 285

Val Gln Lys Ser Asn Trp Glu Ala Gly Asn Thr Phe Thr Cys Ser Val
290 295 300

Leu His Glu Gly Leu His Asn His His Thr Glu Lys Ser Leu Ser His
305 310 315 320

Ser Pro Gly Lys

<210> SEQ ID NO 10
<211> LENGTH: 20
<212> TYPE: PRT
<213> ORGANISM: Artificial Sequence
<220> FEATURE:
<223> OTHER INFORMATION: Synthetic construct

<400> SEQUENCE: 10

Met Glu Thr Asp Thr Leu Leu Leu Trp Val Leu Leu Leu Trp Val Pro
1 5 10 15

```
Gly Ser Thr Gly
            20


<210> SEQ ID NO 11
<211> LENGTH: 23
<212> TYPE: PRT
<213> ORGANISM: Artificial Sequence
<220> FEATURE:
<223> OTHER INFORMATION: Synthetic construct

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys
            20


<210> SEQ ID NO 12
<211> LENGTH: 15
<212> TYPE: PRT
<213> ORGANISM: Artificial Sequence
<220> FEATURE:
<223> OTHER INFORMATION: Synthetic construct

<400> SEQUENCE: 12

Arg Ala Ser Gln Ser Val Ser Thr Ser Arg Tyr Thr Tyr Met His
1               5                   10                  15


<210> SEQ ID NO 13
<211> LENGTH: 15
<212> TYPE: PRT
<213> ORGANISM: Artificial Sequence
<220> FEATURE:
<223> OTHER INFORMATION: Synthetic construct

<400> SEQUENCE: 13

Trp Tyr Gln Gln Lys Pro Gly Gln Pro Pro Lys Leu Leu Ile Lys
1               5                   10                  15


<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

Tyr Ala Ser Asn Leu Asp Ser
1               5


<210> SEQ ID NO 15
<211> LENGTH: 32
<212> TYPE: PRT
<213> ORGANISM: Artificial Sequence
<220> FEATURE:
<223> OTHER INFORMATION: Synthetic construct

<400> SEQUENCE: 15

Gly Val Pro Ala Arg Phe Ser Gly Ser Gly Ser Gly Thr Asp Phe Thr
1               5                   10                  15

Leu Asn Ile His Pro Val Gln Glu Glu Asp Thr Ala Thr Tyr Tyr Cys
            20                  25                  30


<210> SEQ ID NO 16
<211> LENGTH: 8
<212> TYPE: PRT
```

<213> ORGANISM: Artificial Sequence
<220> FEATURE:
<223> OTHER INFORMATION: Synthetic construct

<400> SEQUENCE: 16

Gln His Ser Trp Glu Ile Trp Ala
1 5

<210> SEQ ID NO 17
<211> LENGTH: 10
<212> TYPE: PRT
<213> ORGANISM: Artificial Sequence
<220> FEATURE:
<223> OTHER INFORMATION: Synthetic construct

<400> SEQUENCE: 17

Phe Gly Gly Gly Thr Lys Leu Glu Ile Lys
1 5 10

<210> SEQ ID NO 18
<211> LENGTH: 107
<212> TYPE: PRT
<213> ORGANISM: Artificial Sequence
<220> FEATURE:
<223> OTHER INFORMATION: Synthetic construct

<400> SEQUENCE: 18

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

Thr Tyr Ser Met Ser Ser Thr Leu Thr Leu Thr Lys Asp Glu Tyr Glu
65 70 75 80

Arg His Asn Ser Tyr Thr Cys Glu Ala Thr His Lys Thr Ser Thr Ser
85 90 95

Pro Ile Val Lys Ser Phe Asn Arg Asn Glu Cys
100 105

<210> SEQ ID NO 19
<211> LENGTH: 57
<212> TYPE: DNA
<213> ORGANISM: Artificial Sequence
<220> FEATURE:
<223> OTHER INFORMATION: Synthetic construct

<400> SEQUENCE: 19
atgaaatgca gctgggttat cttcttcctg atggcagtgg ttacaggggt caattca 57

<210> SEQ ID NO 20
<211> LENGTH: 90
<212> TYPE: DNA
<213> ORGANISM: Artificial Sequence
<220> FEATURE:
<223> OTHER INFORMATION: Synthetic construct

<400> SEQUENCE: 20
gaggttcagc tgcagcagtc tggggcagag cttgtgaagc caggggcctc agtccagttg 60
tcctgcacag cttctggctt caacattaaa 90

<210> SEQ ID NO 21
<211> LENGTH: 15
<212> TYPE: DNA
<213> ORGANISM: Artificial Sequence
<220> FEATURE:
<223> OTHER INFORMATION: Synthetic construct

<400> SEQUENCE: 21
gacacctata tacac 15

<210> SEQ ID NO 22
<211> LENGTH: 42
<212> TYPE: DNA
<213> ORGANISM: Artificial Sequence
<220> FEATURE:
<223> OTHER INFORMATION: Synthetic construct

<400> SEQUENCE: 22
tgggtgaaac agaggcctga acagggcctg gagtggattg ga 42

<210> SEQ ID NO 23
<211> LENGTH: 51
<212> TYPE: DNA
<213> ORGANISM: Artificial Sequence
<220> FEATURE:
<223> OTHER INFORMATION: Synthetic construct

<400> SEQUENCE: 23
aggattgatc ctgaggatgg caatactaaa tatgacccga agttccaggc c 51

<210> SEQ ID NO 24
<211> LENGTH: 96
<212> TYPE: DNA
<213> ORGANISM: Artificial Sequence
<220> FEATURE:
<223> OTHER INFORMATION: Synthetic construct

<400> SEQUENCE: 24
aaggccacta taacagcaga cacattctcc aatacagcct acctgcagct cagcagcctg 60
acatctgagg acactgccgt ctattactgt gctaga 96

<210> SEQ ID NO 25
<211> LENGTH: 18
<212> TYPE: DNA
<213> ORGANISM: Artificial Sequence
<220> FEATURE:
<223> OTHER INFORMATION: Synthetic construct

<400> SEQUENCE: 25
tcgtatggta acgcttac 18

<210> SEQ ID NO 26
<211> LENGTH: 33
<212> TYPE: DNA
<213> ORGANISM: Artificial Sequence
<220> FEATURE:
<223> OTHER INFORMATION: Synthetic construct

<400> SEQUENCE: 26
tggggccaag ggactctggt cactgtctct gca 33

<210> SEQ ID NO 27
<211> LENGTH: 975
<212> TYPE: DNA
<213> ORGANISM: Artificial Sequence
<220> FEATURE:
<223> OTHER INFORMATION: Synthetic construct

<400> SEQUENCE: 27
gccaaaacga cacccccatc tgtctatcca ctggcccctg gatctgctgc ccaaactaac 60
tccatggtga ccctgggatg cctggtcaag ggctatttcc ctgagccagt gacagtgacc 120
tggaactctg gatccctgtc cagcggtgtg cacaccttcc cagctgtcct gcagtctgac 180
ctctacactc tgagcagctc agtgactgtc ccctccagca cctggcccag cgagaccgtc 240
acctgcaacg ttgcccaccc ggccagcagc accaaggtgg acaagaaaat tgtgcccagg 300
gattgtggtt gtaagccttg catatgtaca gtcccagaag tatcatctgt cttcatcttc 360
cccccaaagc ccaaggatgt gctcaccatt actctgactc ctaaggtcac gtgtgttgtg 420
gtagacatca gcaaggatga tcccgaggtc cagttcagct ggtttgtaga tgatgtggag 480
gtgcacacag ctcagacgca accccgggag gagcagttca acagcacttt ccgctcagtc 540
agtgaacttc ccatcatgca ccaggactgg ctcaatggca aggagttcaa atgcagggtc 600
aacagtgcag ctttccctgc ccccatcgag aaaaccatct ccaaaaccaa aggcagaccg 660
aaggctccac aggtgtacac cattccacct cccaaggagc agatggccaa ggataaagtc 720
agtctgacct gcatgataac agacttcttc cctgaagaca ttactgtgga gtggcagtgg 780
aatgggcagc cagcggagaa ctacaagaac actcagccca tcatggacac agatggctct 840
tacttcgtct acagcaagct caatgtgcag aagagcaact gggaggcagg aaatactttc 900
acctgctctg tgttacatga gggcctgcac aaccaccata ctgagaagag cctctcccac 960
tctcctggta aatga 975

<210> SEQ ID NO 28
<211> LENGTH: 60
<212> TYPE: DNA
<213> ORGANISM: Artificial Sequence
<220> FEATURE:
<223> OTHER INFORMATION: Synthetic construct

<400> SEQUENCE: 28
atggagacag acacactcct gctatgggtg ctgctgctct gggttccagg ttccactggt 60

<210> SEQ ID NO 29
<211> LENGTH: 69
<212> TYPE: DNA
<213> ORGANISM: Artificial Sequence
<220> FEATURE:
<223> OTHER INFORMATION: Synthetic construct

<400> SEQUENCE: 29
gacattgtgc tgacacagtc tcctgcttcc ttagctgtat ctctggggca gagggccacc 60
atctcatgc 69

<210> SEQ ID NO 30
<211> LENGTH: 45
<212> TYPE: DNA
<213> ORGANISM: Artificial Sequence
<220> FEATURE:
<223> OTHER INFORMATION: Synthetic construct

<400> SEQUENCE: 30
agggccagcc aaagtgtcag tacatctagg tacacttata tgcac 45

<210> SEQ ID NO 31

<211> LENGTH: 45
<212> TYPE: DNA
<213> ORGANISM: Artificial Sequence
<220> FEATURE:
<223> OTHER INFORMATION: Synthetic construct

<400> SEQUENCE: 31
tggtaccaac agaaaccagg acagccaccc aaactcctca tcaaa 45

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
tatgcatcca acctagattc t 21

<210> SEQ ID NO 33
<211> LENGTH: 96
<212> TYPE: DNA
<213> ORGANISM: Artificial Sequence
<220> FEATURE:
<223> OTHER INFORMATION: Synthetic construct

<400> SEQUENCE: 33
ggggtccctg ccaggttcag tggcagtggg tctgggacag acttcaccct caacatccat 60
cctgtgcagg aggaggatac tgcaacatat tactgt 96

<210> SEQ ID NO 34
<211> LENGTH: 24
<212> TYPE: DNA
<213> ORGANISM: Artificial Sequence
<220> FEATURE:
<223> OTHER INFORMATION: Synthetic construct

<400> SEQUENCE: 34
cagcacagtt gggagatttg ggcg 24

<210> SEQ ID NO 35
<211> LENGTH: 30
<212> TYPE: DNA
<213> ORGANISM: Artificial Sequence
<220> FEATURE:
<223> OTHER INFORMATION: Synthetic construct

<400> SEQUENCE: 35
ttcggtggag gcaccaagct ggaaatcaaa 30

<210> SEQ ID NO 36
<211> LENGTH: 324
<212> TYPE: DNA
<213> ORGANISM: Artificial Sequence
<220> FEATURE:
<223> OTHER INFORMATION: Synthetic construct

<400> SEQUENCE: 36
cgggctgatg ctgcaccaac tgtatccatc ttcccaccat ccagtgagca gttaacatct 60
ggaggtgcct cagtcgtgtg cttcttgaac aacttctacc ccaaagacat caatgtcaag 120
tggaagattg atggcagtga acgacaaaat ggcgtcctga acagttggac tgatcaggac 180
agcaaagaca gcacctacag catgagcagc accctcacgt tgaccaagga cgagtatgaa 240
cgacataaca gctatacctg tgaggccact cacaagacat caacttcacc cattgtcaag 300

-continued

```
agcttcaaca ggaatgagtg ttag                                          324


<210> SEQ ID NO 37
<211> LENGTH: 458
<212> TYPE: PRT
<213> ORGANISM: Artificial Sequence
<220> FEATURE:
<223> OTHER INFORMATION: Synthetic construct

<400> SEQUENCE: 37

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Gln Leu Ser Cys Thr Ala Ser Gly Phe Asn Ile
        35                  40                  45

Lys Asp Thr Tyr Ile His Trp Val Lys Gln Arg Pro Glu Gln Gly Leu
    50                  55                  60

Glu Trp Ile Gly Arg Ile Asp Pro Glu Asp Gly Asn Thr Lys Tyr Asp
65                  70                  75                  80

Pro Lys Phe Gln Ala Lys Ala Thr Ile Thr Ala Asp Thr Phe Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Ser Tyr Gly Asn Ala Tyr Trp Gly Gln Gly Thr
        115                 120                 125

Leu Val Thr Val Ser Ala Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Glu Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
            340                 345                 350
```

```
Arg Pro Lys Ala Pro Gln Val Tyr Thr Ile Pro Pro Pro Lys Glu Gln
        355                 360                 365

Met Ala Lys Asp Lys Val Ser Leu Thr Cys Met Ile Thr Asp Phe Phe
    370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
        435                 440                 445

Glu Lys Ser Leu Ser His Ser Pro Gly Lys
    450                 455


<210> SEQ ID NO 38
<211> LENGTH: 115
<212> TYPE: PRT
<213> ORGANISM: Artificial Sequence
<220> FEATURE:
<223> OTHER INFORMATION: Synthetic construct

<400> SEQUENCE: 38

Glu Val Gln Leu Gln Gln Ser Gly Ala Glu Leu Val Lys Pro Gly Ala
1               5                   10                  15

Ser Val Gln Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Glu Asp Gly Asn Thr Lys Tyr Asp Pro Lys Phe
    50                  55                  60

Gln Ala Lys Ala Thr Ile Thr Ala Asp Thr Phe Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Tyr Gly Asn Ala Tyr Trp Gly Gln Gly Thr Leu Val Thr
            100                 105                 110

Val Ser Ala
        115


<210> SEQ ID NO 39
<211> LENGTH: 237
<212> TYPE: PRT
<213> ORGANISM: Artificial Sequence
<220> FEATURE:
<223> OTHER INFORMATION: Synthetic construct

<400> SEQUENCE: 39

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Gln Ser
        35                  40                  45

Val Ser Thr Ser Arg Tyr Thr Tyr Met His Trp Tyr Gln Gln Lys Pro
    50                  55                  60

Gly Gln Pro Pro Lys Leu Leu Ile Lys Tyr Ala Ser Asn Leu Asp Ser
65                  70                  75                  80
```

```
Gly Val Pro Ala Arg Phe Ser Gly Ser Gly Ser Gly Thr Asp Phe Thr
                85                  90                  95

Leu Asn Ile His Pro Val Gln Glu Glu Asp Thr Ala Thr Tyr Tyr Cys
            100                 105                 110

Gln His Ser Trp Glu Ile Trp Ala Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235


<210> SEQ ID NO 40
<211> LENGTH: 110
<212> TYPE: PRT
<213> ORGANISM: Artificial Sequence
<220> FEATURE:
<223> OTHER INFORMATION: Synthetic construct

<400> SEQUENCE: 40

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Thr Tyr Met His Trp Tyr Gln Gln Lys Pro Gly Gln Pro Pro
        35                  40                  45

Lys Leu Leu Ile Lys Tyr Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Gln Glu Glu Asp Thr Ala Thr Tyr Tyr Cys Gln His Ser Trp
                85                  90                  95

Glu Ile Trp Ala Phe Gly Gly Gly Thr Lys Leu Glu Ile Lys
            100                 105                 110


<210> SEQ ID NO 41
<211> LENGTH: 1377
<212> TYPE: DNA
<213> ORGANISM: Artificial Sequence
<220> FEATURE:
<223> OTHER INFORMATION: Synthetic construct

<400> SEQUENCE: 41

atgaaatgca gctgggttat cttcttcctg atggcagtgg ttacaggggt caattcagag      60

gttcagctgc agcagtctgg ggcagagctt gtgaagccag gggcctcagt ccagttgtcc     120

tgcacagctt ctggcttcaa cattaaagac acctatatac actgggtgaa acagaggcct     180

gaacagggcc tggagtggat tggaaggatt gatcctgagg atggcaatac taaatatgac     240
```

-continued

```
ccgaagttcc aggccaaggc cactataaca gcagacacat tctccaatac agcctacctg    300

cagctcagca gcctgacatc tgaggacact gccgtctatt actgtgctag atcgtatggt    360

aacgcttact ggggccaagg gactctggtc actgtctctg cagccaaaac gacaccccca    420

tctgtctatc cactggcccc tggatctgct gcccaaacta actccatggt gaccctggga    480

tgcctggtca agggctattt ccctgagcca gtgacagtga cctggaactc tggatccctg    540

tccagcggtg tgcacacctt cccagctgtc ctgcagtctg acctctacac tctgagcagc    600

tcagtgactg tcccctccag cacctggccc agcgagaccg tcacctgcaa cgttgcccac    660

ccggccagca gcaccaaggt ggacaagaaa attgtgccca gggattgtgg ttgtaagcct    720

tgcatatgta cagtcccaga agtatcatct gtcttcatct tccccccaaa gcccaaggat    780

gtgctcacca ttactctgac tcctaaggtc acgtgtgttg tggtagacat cagcaaggat    840

gatcccgagg tccagttcag ctggtttgta gatgatgtgg aggtgcacac agctcagacg    900

caaccccggg aggagcagtt caacagcact ttccgctcag tcagtgaact tcccatcatg    960

caccaggact ggctcaatgg caaggagttc aaatgcaggg tcaacagtgc agctttccct   1020

gcccccatcg agaaaaccat ctccaaaacc aaaggcagac cgaaggctcc acaggtgtac   1080

accattccac ctcccaagga gcagatggcc aaggataaag tcagtctgac ctgcatgata   1140

acagacttct tccctgaaga cattactgtg gagtggcagt ggaatgggca gccagcggag   1200

aactacaaga acactcagcc catcatggac acagatggct cttacttcgt ctacagcaag   1260

ctcaatgtgc agaagagcaa ctgggaggca ggaaatactt tcacctgctc tgtgttacat   1320

gagggcctgc acaaccacca tactgagaag agcctctccc actctcctgg taaatga      1377
```

<210> SEQ ID NO 42
<211> LENGTH: 714
<212> TYPE: DNA
<213> ORGANISM: Artificial Sequence
<220> FEATURE:
<223> OTHER INFORMATION: Synthetic construct

<400> SEQUENCE: 42

```
atggagacag acacactcct gctatgggtg ctgctgctct gggttccagg ttccactggt     60

gacattgtgc tgacacagtc tcctgcttcc ttagctgtat ctctggggca gagggccacc    120

atctcatgca gggccagcca aagtgtcagt acatctaggt acacttatat gcactggtac    180

caacagaaac caggacagcc acccaaactc ctcatcaaat atgcatccaa cctagattct    240

ggggtccctg ccaggttcag tggcagtggg tctgggacag acttcaccct caacatccat    300

cctgtgcagg aggaggatac tgcaacatat tactgtcagc acagttggga gatttgggcg    360

ttcggtggag gcaccaagct ggaaatcaaa cgggctgatg ctgcaccaac tgtatccatc    420

ttcccaccat ccagtgagca gttaacatct ggaggtgcct cagtcgtgtg cttcttgaac    480

aacttctacc ccaaagacat caatgtcaag tggaagattg atggcagtga acgacaaaat    540

ggcgtcctga acagttggac tgatcaggac agcaaagaca gcacctacag catgagcagc    600

accctcacgt tgaccaagga cgagtatgaa cgacataaca gctatacctg tgaggccact    660

cacaagacat caacttcacc cattgtcaag agcttcaaca ggaatgagtg ttag          714
```

<210> SEQ ID NO 43
<211> LENGTH: 19
<212> TYPE: PRT
<213> ORGANISM: Artificial Sequence
<220> FEATURE:

-continued

<223> OTHER INFORMATION: Synthetic construct

<400> SEQUENCE: 43

```
Met Gly Trp Ser Trp Ile Phe Leu Phe Leu Leu Ser Gly Thr Ala Gly
1               5                   10                  15

Val Leu Ser
```

<210> SEQ ID NO 44
<211> LENGTH: 30
<212> TYPE: PRT
<213> ORGANISM: Artificial Sequence
<220> FEATURE:
<223> OTHER INFORMATION: Synthetic construct

<400> SEQUENCE: 44

```
Glu Val Gln Leu Gln Gln Ser Gly Pro Glu Leu Val Lys Ser Gly Ala
1               5                   10                  15

Ser Val Lys Ile Ser Cys Lys Thr Ser Gly Tyr Thr Phe Thr
            20                  25                  30
```

<210> SEQ ID NO 45
<211> LENGTH: 5
<212> TYPE: PRT
<213> ORGANISM: Artificial Sequence
<220> FEATURE:
<223> OTHER INFORMATION: Synthetic construct

<400> SEQUENCE: 45

```
Glu Tyr Thr Ile His
1               5
```

<210> SEQ ID NO 46
<211> LENGTH: 14
<212> TYPE: PRT
<213> ORGANISM: Artificial Sequence
<220> FEATURE:
<223> OTHER INFORMATION: Synthetic contruct

<400> SEQUENCE: 46

```
Trp Val Lys Gln Ser His Gly Glu Ser Leu Glu Trp Val Gly
1               5                   10
```

<210> SEQ ID NO 47
<211> LENGTH: 17
<212> TYPE: PRT
<213> ORGANISM: Artificial Sequence
<220> FEATURE:
<223> OTHER INFORMATION: Synthetic construct

<400> SEQUENCE: 47

```
Gly Ile Asn Pro Lys Asn Gly Gly Ile Ser Tyr Asn Gln Lys Phe Lys
1               5                   10                  15

Gly
```

<210> SEQ ID NO 48
<211> LENGTH: 32
<212> TYPE: PRT
<213> ORGANISM: Artificial Sequence
<220> FEATURE:
<223> OTHER INFORMATION: Synthetic construct

<400> SEQUENCE: 48

```
Lys Ala Thr Leu Thr Val Asp Lys Ser Ser Ser Thr Ala Tyr Met Glu
1               5                   10                  15
```

```
Leu Arg Ser Leu Thr Ser Glu Asp Ser Ala Val Tyr Phe Cys Ala Arg
            20                  25                  30


<210> SEQ ID NO 49
<211> LENGTH: 11
<212> TYPE: PRT
<213> ORGANISM: Artificial Sequence
<220> FEATURE:
<223> OTHER INFORMATION: Synthetic construct

<400> SEQUENCE: 49

Trp Gly Ile Gly Asn Tyr Val Gly Phe Pro Tyr
1               5                   10


<210> SEQ ID NO 50
<211> LENGTH: 11
<212> TYPE: PRT
<213> ORGANISM: Artificial Sequence
<220> FEATURE:
<223> OTHER INFORMATION: Synthetic construct

<400> SEQUENCE: 50

Trp Gly Gln Gly Thr Leu Val Thr Val Ser Ala
1               5                   10


<210> SEQ ID NO 51
<211> LENGTH: 336
<212> TYPE: PRT
<213> ORGANISM: Artificial Sequence
<220> FEATURE:
<223> OTHER INFORMATION: Synthetic construct

<400> SEQUENCE: 51

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
```

```
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335


<210> SEQ ID NO 52
<211> LENGTH: 20
<212> TYPE: PRT
<213> ORGANISM: Artificial Sequence
<220> FEATURE:
<223> OTHER INFORMATION: Synthetic construct

<400> SEQUENCE: 52

Met Lys Ser Gln Thr Gln Val Phe Val Phe Leu Leu Leu Cys Val Ser
1               5                   10                  15

Gly Val His Gly
            20


<210> SEQ ID NO 53
<211> LENGTH: 23
<212> TYPE: PRT
<213> ORGANISM: Artificial Sequence
<220> FEATURE:
<223> OTHER INFORMATION: Synthetic construct

<400> SEQUENCE: 53

Ser Ile Val Met Thr Gln Thr Pro Lys Phe Leu Leu Val Ser Ala Gly
1               5                   10                  15

Asp Arg Val Thr Met Thr Cys
            20


<210> SEQ ID NO 54
<211> LENGTH: 11
<212> TYPE: PRT
<213> ORGANISM: Artificial Sequence
<220> FEATURE:
<223> OTHER INFORMATION: Synthetic construct

<400> SEQUENCE: 54

Lys Ala Ser Leu Ser Val Asn Asn Asp Val Ala
1               5                   10


<210> SEQ ID NO 55
<211> LENGTH: 15
<212> TYPE: PRT
<213> ORGANISM: Artificial Sequence
<220> FEATURE:
<223> OTHER INFORMATION: Synthetic construct

<400> SEQUENCE: 55

Trp Tyr Gln Gln Lys Pro Gly Gln Ser Pro Lys Leu Leu Ile Ser
```

-continued 1 5 10 15

<210> SEQ ID NO 56
<211> LENGTH: 7
<212> TYPE: PRT
<213> ORGANISM: Artificial Sequence
<220> FEATURE:
<223> OTHER INFORMATION: Synthetic construct

<400> SEQUENCE: 56

Tyr Ala Ser Ser Arg Tyr Thr
1 5

<210> SEQ ID NO 57
<211> LENGTH: 32
<212> TYPE: PRT
<213> ORGANISM: Artificial Sequence
<220> FEATURE:
<223> OTHER INFORMATION: Synthetic construct

<400> SEQUENCE: 57

Gly Val Pro Asp Arg Phe Thr Gly Ser Gly Tyr Gly Thr Asp Phe Thr
1 5 10 15

Phe Thr Ile Ser Ser Val Gln Ala Glu Asp Leu Ala Val Tyr Phe Cys
20 25 30

<210> SEQ ID NO 58
<211> LENGTH: 9
<212> TYPE: PRT
<213> ORGANISM: Artificial Sequence
<220> FEATURE:
<223> OTHER INFORMATION: Synthetic construct

<400> SEQUENCE: 58

Gln Gln Asp Tyr Ser Ser Pro Leu Thr
1 5

<210> SEQ ID NO 59
<211> LENGTH: 10
<212> TYPE: PRT
<213> ORGANISM: Artificial Sequence
<220> FEATURE:
<223> OTHER INFORMATION: Synthetic construct

<400> SEQUENCE: 59

Phe Gly Ala Gly Thr Lys Leu Glu Leu Lys
1 5 10

<210> SEQ ID NO 60
<211> LENGTH: 107
<212> TYPE: PRT
<213> ORGANISM: Artificial Sequence
<220> FEATURE:
<223> OTHER INFORMATION: Synthetic construct

<400> SEQUENCE: 60

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

-continued

```
Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 61
<211> LENGTH: 57
<212> TYPE: DNA
<213> ORGANISM: Artificial Sequence
<220> FEATURE:
<223> OTHER INFORMATION: Synthetic construct

<400> SEQUENCE: 61

atgggatgga gctggatctt tctctttctc ctgtcaggaa ctgcaggtgt cctctct        57


<210> SEQ ID NO 62
<211> LENGTH: 90
<212> TYPE: DNA
<213> ORGANISM: Artificial Sequence
<220> FEATURE:
<223> OTHER INFORMATION: Synthetic construct

<400> SEQUENCE: 62

gaggtccagc tgcaacagtc tggacctgag ctggtgaagt ctggggcttc agtgaagata      60

tcctgcaaga cctctggata cactttcact                                      90


<210> SEQ ID NO 63
<211> LENGTH: 15
<212> TYPE: DNA
<213> ORGANISM: Artificial Sequence
<220> FEATURE:
<223> OTHER INFORMATION: Synthetic construct

<400> SEQUENCE: 63

gaatacacca tacac                                                      15


<210> SEQ ID NO 64
<211> LENGTH: 42
<212> TYPE: DNA
<213> ORGANISM: Artificial Sequence
<220> FEATURE:
<223> OTHER INFORMATION: Synthetic construct

<400> SEQUENCE: 64

tgggtgaagc agagccatgg agagagcctt gagtgggttg ga                        42


<210> SEQ ID NO 65
<211> LENGTH: 51
<212> TYPE: DNA
<213> ORGANISM: Artificial Sequence
<220> FEATURE:
<223> OTHER INFORMATION: Synthetic construct

<400> SEQUENCE: 65

ggtattaatc ctaaaaatgg tggtattagt tacaaccaga agttcaaggg c              51


<210> SEQ ID NO 66
<211> LENGTH: 96
<212> TYPE: DNA
<213> ORGANISM: Artificial Seqence
<220> FEATURE:
<223> OTHER INFORMATION: Synthetic construct
```

-continued

<400> SEQUENCE: 66
aaggccacat tgactgtaga caagtcctcc agcacagcct acatggagct ccgcagcctg 60
acatctgagg attccgcagt ctatttctgt gcaaga 96

<210> SEQ ID NO 67
<211> LENGTH: 33
<212> TYPE: DNA
<213> ORGANISM: Artificial Sequence
<220> FEATURE:
<223> OTHER INFORMATION: Synthetic construct

<400> SEQUENCE: 67
tggggtattg gtaactacgt ggggtttcct tac 33

<210> SEQ ID NO 68
<211> LENGTH: 33
<212> TYPE: DNA
<213> ORGANISM: Artificial Sequence
<220> FEATURE:
<223> OTHER INFORMATION: Synthetic construct

<400> SEQUENCE: 68
tggggccaag ggactctggt cactgtctct gca 33

<210> SEQ ID NO 69
<211> LENGTH: 1008
<212> TYPE: DNA
<213> ORGANISM: Artificial Sequence
<220> FEATURE:
<223> OTHER INFORMATION: Synthetic cosntruct

<400> SEQUENCE: 69
gccaaaacaa cacccccatc agtctatcca ctggcccctg ggtgtggaga tacaactggt 60
tcctccgtga ctctgggatg cctggtcaag ggctacttcc ctgagtcagt gactgtgact 120
tggaactctg gatccctgtc cagcagtgtg cacaccttcc cagctctcct gcagtctgga 180
ctctacacta tgagcagctc agtgactgtc ccctccagca cctggccaag tcagaccgtc 240
acctgcagcg ttgctcaccc agccagcagc accacggtgg acaaaaaact tgagcccagc 300
gggcccattt caacaatcaa cccctgtcct ccatgcaagg agtgtcacaa atgcccagct 360
cctaacctcg agggtggacc atccgtcttc atcttccctc caaatatcaa ggatgtactc 420
atgatctccc tgacacccaa ggtcacgtgt gtggtggtgg atgtgagcga ggatgaccca 480
gacgtccaga tcagctggtt tgtgaacaac gtggaagtac acacagctca gacacaaacc 540
catagagagg attacaacag tactatccgg gtggtcagca ccctccccat ccagcaccag 600
gactggatga gtggcaagga gttcaaatgc aaggtcaaca acaaagacct cccatcaccc 660
atcgagagaa ccatctcaaa aattaaaggg ctagtcagag ctccacaagt atacatcttg 720
ccgccaccag cagagcagtt gtccaggaaa gatgtcagtc tcacttgcct ggtcgtgggc 780
ttcaaccctg gagacatcag tgtggagtgg accagcaatg ggcatacaga ggagaactac 840
aaggacaccg caccagtcct ggactctgac ggttcttact tcatatatag caagctcaat 900
atgaaaacaa gcaagtggga gaaaacagat tccttctcat gcaacgtgag acacgagggt 960
ctgaaaaatt actacctgaa gaagaccatc tcccggtctc cgggtaaa 1008

<210> SEQ ID NO 70
<211> LENGTH: 60
<212> TYPE: DNA
<213> ORGANISM: Artificial Sequence
<220> FEATURE:
<223> OTHER INFORMATION: Synthetic construct

<400> SEQUENCE: 70
atgaagtcac agacccaggt cttcgtattt ctactgctct gtgtgtctgg tgttcatggg 60

<210> SEQ ID NO 71
<211> LENGTH: 69
<212> TYPE: DNA
<213> ORGANISM: Artificial Sequence
<220> FEATURE:
<223> OTHER INFORMATION: Synthetic construct

<400> SEQUENCE: 71
agtattgtga tgacccagac tcccaaattc ctgcttgtat cagcaggaga cagggttacc 60
atgacctgc 69

<210> SEQ ID NO 72
<211> LENGTH: 33
<212> TYPE: DNA
<213> ORGANISM: Artificial Sequence
<220> FEATURE:
<223> OTHER INFORMATION: Synthetic construct

<400> SEQUENCE: 72
aaggccagtc tgagtgtgaa taatgatgta gct 33

<210> SEQ ID NO 73
<211> LENGTH: 45
<212> TYPE: DNA
<213> ORGANISM: Artificial Sequence
<220> FEATURE:
<223> OTHER INFORMATION: Synthetic construct

<400> SEQUENCE: 73
tggtaccaac agaagccagg gcagtctcct aaactactga tatcc 45

<210> SEQ ID NO 74
<211> LENGTH: 21
<212> TYPE: DNA
<213> ORGANISM: Artificial Sequence
<220> FEATURE:
<223> OTHER INFORMATION: Synthetic construct

<400> SEQUENCE: 74
tatgcatcca gtcgctacac t 21

<210> SEQ ID NO 75
<211> LENGTH: 96
<212> TYPE: DNA
<213> ORGANISM: Artificial Sequence
<220> FEATURE:
<223> OTHER INFORMATION: Synthetic construct

<400> SEQUENCE: 75
ggagtccctg atcgcttcac tggcagtgga tatgggacgg atttcacttt caccatcagc 60
tctgtgcagg ctgaagacct ggcagtttat ttctgt 96

<210> SEQ ID NO 76
<211> LENGTH: 27
<212> TYPE: DNA
<213> ORGANISM: Artificial Sequence
<220> FEATURE:
<223> OTHER INFORMATION: Synthetic construct

<400> SEQUENCE: 76
cagcaggatt atagctctcc gctcacg 27

<210> SEQ ID NO 77
<211> LENGTH: 30
<212> TYPE: DNA
<213> ORGANISM: Artificial Sequence
<220> FEATURE:
<223> OTHER INFORMATION: Synthetic construct

<400> SEQUENCE: 77
ttcggtgctg ggaccaagct ggagctgaaa 30

<210> SEQ ID NO 78
<211> LENGTH: 321
<212> TYPE: DNA
<213> ORGANISM: Artificial Sequence
<220> FEATURE:
<223> OTHER INFORMATION: Synthetic construct

<400> SEQUENCE: 78
cgggctgatg ctgcaccaac tgtatccatc ttcccaccat ccagtgagca gttaacatct 60
ggaggtgcct cagtcgtgtg cttcttgaac aacttctacc ccaaagacat caatgtcaag 120
tggaagattg atggcagtga acgacaaaat ggcgtcctga acagttggac tgatcaggac 180
agcaaagaca gcacctacag catgagcagc accctcacgt tgaccaagga cgagtatgaa 240
cgacataaca gctatacctg tgaggccact cacaagacat caacttcacc cattgtcaag 300
agcttcaaca ggaatgagtg t 321

<210> SEQ ID NO 79
<211> LENGTH: 475
<212> TYPE: PRT
<213> ORGANISM: Artificial Sequence
<220> FEATURE:
<223> OTHER INFORMATION: Synthetic construct

<400> SEQUENCE: 79

Met Gly Trp Ser Trp Ile Phe Leu Phe Leu Leu Ser Gly Thr Ala Gly
1 5 10 15

Val Leu Ser Glu Val Gln Leu Gln Gln Ser Gly Pro Glu Leu Val Lys
20 25 30

Ser Gly Ala Ser Val Lys Ile Ser Cys Lys Thr Ser Gly Tyr Thr Phe
35 40 45

Thr Glu Tyr Thr Ile His Trp Val Lys Gln Ser His Gly Glu Ser Leu
50 55 60

Glu Trp Val Gly Gly Ile Asn Pro Lys Asn Gly Gly Ile Ser Tyr Asn
65 70 75 80

Gln Lys Phe Lys Gly Lys Ala Thr Leu Thr Val Asp Lys Ser Ser Ser
85 90 95

Thr Ala Tyr Met Glu Leu Arg Ser Leu Thr Ser Glu Asp Ser Ala Val
100 105 110

Tyr Phe Cys Ala Arg Trp Gly Ile Gly Asn Tyr Val Gly Phe Pro Tyr
115 120 125

Trp Gly Gln Gly Thr Leu Val Thr Val Ser Ala Ala Lys Thr Thr Pro
130 135 140

Pro Ser Val Tyr Pro Leu Ala Pro Gly Cys Gly Asp Thr Thr Gly Ser
145 150 155 160

Ser Val Thr Leu Gly Cys Leu Val Lys Gly Tyr Phe Pro Glu Ser Val 165 170 175

Thr Val Thr Trp Asn Ser Gly Ser Leu Ser Ser Ser Val His Thr Phe
180 185 190

Pro Ala Leu Leu Gln Ser Gly Leu Tyr Thr Met Ser Ser Ser Val Thr
195 200 205

Val Pro Ser Ser Thr Trp Pro Ser Gln Thr Val Thr Cys Ser Val Ala
210 215 220

His Pro Ala Ser Ser Thr Thr Val Asp Lys Lys Leu Glu Pro Ser Gly
225 230 235 240

Pro Ile Ser Thr Ile Asn Pro Cys Pro Pro Cys Lys Glu Cys His Lys
245 250 255

Cys Pro Ala Pro Asn Leu Glu Gly Gly Pro Ser Val Phe Ile Phe Pro
260 265 270

Pro Asn Ile Lys Asp Val Leu Met Ile Ser Leu Thr Pro Lys Val Thr
275 280 285

Cys Val Val Val Asp Val Ser Glu Asp Asp Pro Asp Val Gln Ile Ser
290 295 300

Trp Phe Val Asn Asn Val Glu Val His Thr Ala Gln Thr Gln Thr His
305 310 315 320

Arg Glu Asp Tyr Asn Ser Thr Ile Arg Val Val Ser Thr Leu Pro Ile
325 330 335

Gln His Gln Asp Trp Met Ser Gly Lys Glu Phe Lys Cys Lys Val Asn
340 345 350

Asn Lys Asp Leu Pro Ser Pro Ile Glu Arg Thr Ile Ser Lys Ile Lys
355 360 365

Gly Leu Val Arg Ala Pro Gln Val Tyr Ile Leu Pro Pro Pro Ala Glu
370 375 380

Gln Leu Ser Arg Lys Asp Val Ser Leu Thr Cys Leu Val Val Gly Phe
385 390 395 400

Asn Pro Gly Asp Ile Ser Val Glu Trp Thr Ser Asn Gly His Thr Glu
405 410 415

Glu Asn Tyr Lys Asp Thr Ala Pro Val Leu Asp Ser Asp Gly Ser Tyr
420 425 430

Phe Ile Tyr Ser Lys Leu Asn Met Lys Thr Ser Lys Trp Glu Lys Thr
435 440 445

Asp Ser Phe Ser Cys Asn Val Arg His Glu Gly Leu Lys Asn Tyr Tyr
450 455 460

Leu Lys Lys Thr Ile Ser Arg Ser Pro Gly Lys
465 470 475

<210> SEQ ID NO 80
<211> LENGTH: 120
<212> TYPE: PRT
<213> ORGANISM: Artificial Sequence
<220> FEATURE:
<223> OTHER INFORMATION: Synthetic construct

<400> SEQUENCE: 80

Glu Val Gln Leu Gln Gln Ser Gly Pro Glu Leu Val Lys Ser Gly Ala
1 5 10 15

Ser Val Lys Ile Ser Cys Lys Thr Ser Gly Tyr Thr Phe Thr Glu Tyr
20 25 30

Thr Ile His Trp Val Lys Gln Ser His Gly Glu Ser Leu Glu Trp Val
35 40 45

Gly Gly Ile Asn Pro Lys Asn Gly Gly Ile Ser Tyr Asn Gln Lys Phe

```
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Trp Gly Ile Gly Asn Tyr Val Gly Phe Pro Tyr Trp Gly Gln
            100                 105                 110

Gly Thr Leu Val Thr Val Ser Ala
        115                 120


<210> SEQ ID NO 81
<211> LENGTH: 234
<212> TYPE: PRT
<213> ORGANISM: Artificial Sequence
<220> FEATURE:
<223> OTHER INFORMATION: Synthetic construct

<400> SEQUENCE: 81

Met Lys Ser Gln Thr Gln Val Phe Val Phe Leu Leu Leu Cys Val Ser
1               5                   10                  15

Gly Val His Gly Ser Ile Val Met Thr Gln Thr Pro Lys Phe Leu Leu
            20                  25                  30

Val Ser Ala Gly Asp Arg Val Thr Met Thr Cys Lys Ala Ser Leu Ser
        35                  40                  45

Val Asn Asn Asp Val Ala Trp Tyr Gln Gln Lys Pro Gly Gln Ser Pro
    50                  55                  60

Lys Leu Leu Ile Ser Tyr Ala Ser Ser Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Ser Val Gln Ala Glu Asp Leu Ala Val Tyr Phe Cys Gln Gln Asp Tyr
            100                 105                 110

Ser Ser Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 82
<211> LENGTH: 107
<212> TYPE: PRT
<213> ORGANISM: Artificial Sequence
<220> FEATURE:
<223> OTHER INFORMATION: Synthetic construct

<400> SEQUENCE: 82
```

```
Ser Ile Val Met Thr Gln Thr Pro Lys Phe Leu Leu Val Ser Ala Gly
1               5                   10                  15

Asp Arg Val Thr Met Thr Cys Lys Ala Ser Leu Ser Val Asn Asn Asp
            20                  25                  30

Val Ala Trp Tyr Gln Gln Lys Pro Gly Gln Ser Pro Lys Leu Leu Ile
        35                  40                  45

Ser Tyr Ala Ser Ser Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys
            100                 105


<210> SEQ ID NO 83
<211> LENGTH: 1428
<212> TYPE: DNA
<213> ORGANISM: Artificial Sequence
<220> FEATURE:
<223> OTHER INFORMATION: Synthetic construct

<400> SEQUENCE: 83

atgggatgga gctggatctt tctctttctc ctgtcaggaa ctgcaggtgt cctctctgag     60

gtccagctgc aacagtctgg acctgagctg gtgaagtctg gggcttcagt gaagatatcc    120

tgcaagacct ctggatacac tttcactgaa tacaccatac actgggtgaa gcagagccat    180

ggagagagcc ttgagtgggt tggaggtatt aatcctaaaa atggtggtat tagttacaac    240

cagaagttca agggcaaggc cacattgact gtagacaagt cctccagcac agcctacatg    300

gagctccgca gcctgacatc tgaggattcc gcagtctatt tctgtgcaag atggggtatt    360

ggtaactacg tggggtttcc ttactggggc caagggactc tggtcactgt ctctgcagcc    420

aaaacaacac ccccatcagt ctatccactg gcccctgggt gtggagatac aactggttcc    480

tccgtgactc tgggatgcct ggtcaagggc tacttccctg agtcagtgac tgtgacttgg    540

aactctggat ccctgtccag cagtgtgcac accttcccag ctctcctgca gtctggactc    600

tacactatga gcagctcagt gactgtcccc tccagcacct ggccaagtca gaccgtcacc    660

tgcagcgttg ctcacccagc cagcagcacc acggtggaca aaaaacttga gcccagcggg    720

cccatttcaa caatcaaccc ctgtcctcca tgcaaggagt gtcacaaatg cccagctcct    780

aacctcgagg gtggaccatc cgtcttcatc ttccctccaa atatcaagga tgtactcatg    840

atctccctga cacccaaggt cacgtgtgtg gtggtggatg tgagcgagga tgacccagac    900

gtccagatca gctggtttgt gaacaacgtg gaagtacaca cagctcagac acaaacccat    960

agagaggatt acaacagtac tatccgggtg gtcagcaccc tccccatcca gcaccaggac   1020

tggatgagtg gcaaggagtt caaatgcaag gtcaacaaca aagacctccc atcacccatc   1080

gagagaacca tctcaaaaat taaagggcta gtcagagctc cacaagtata catcttgccg   1140

ccaccagcag agcagttgtc caggaaagat gtcagtctca cttgcctggt cgtgggcttc   1200

aaccctggag acatcagtgt ggagtggacc agcaatgggc atacagagga gaactacaag   1260

gacaccgcac cagtcctgga ctctgacggt tcttacttca tatatagcaa gctcaatatg   1320

aaaacaagca agtgggagaa aacagattcc ttctcatgca acgtgagaca cgagggtctg   1380

aaaaattact acctgaagaa gaccatctcc cggtctccgg gtaaatga                1428
```

<210> SEQ ID NO 84
<211> LENGTH: 705
<212> TYPE: DNA
<213> ORGANISM: Artificial Sequence
<220> FEATURE:
<223> OTHER INFORMATION: Synthetic contruct

<400> SEQUENCE: 84
atgaagtcac agacccaggt cttcgtattt ctactgctct gtgtgtctgg tgttcatggg 60
agtattgtga tgacccagac tcccaaattc ctgcttgtat cagcaggaga cagggttacc 120
atgacctgca aggccagtct gagtgtgaat aatgatgtag cttggtacca acagaagcca 180
gggcagtctc ctaaactact gatatcctat gcatccagtc gctacactgg agtccctgat 240
cgcttcactg gcagtggata tgggacggat ttcactttca ccatcagctc tgtgcaggct 300
gaagacctgg cagtttattt ctgtcagcag gattatagct ctccgctcac gttcggtgct 360
gggaccaagc tggagctgaa acgggctgat gctgcaccaa ctgtatccat cttcccacca 420
tccagtgagc agttaacatc tggaggtgcc tcagtcgtgt gcttcttgaa caacttctac 480
cccaaagaca tcaatgtcaa gtggaagatt gatggcagtg aacgacaaaa tggcgtcctg 540
aacagttgga ctgatcagga cagcaaagac agcacctaca gcatgagcag caccctcacg 600
ttgaccaagg acgagtatga acgacataac agctatacct gtgaggccac tcacaagaca 660
tcaacttcac ccattgtcaa gagcttcaac aggaatgagt gttag 705

<210> SEQ ID NO 85
<211> LENGTH: 19
<212> TYPE: PRT
<213> ORGANISM: Artificial Sequence
<220> FEATURE:
<223> OTHER INFORMATION: Synthetic construct

<400> SEQUENCE: 85

Met Gly Trp Ser Trp Val Phe Leu Phe Leu Leu Ser Val Thr Ala Gly
1 5 10 15

Val His Ser

<210> SEQ ID NO 86
<211> LENGTH: 30
<212> TYPE: PRT
<213> ORGANISM: Artificial Sequence
<220> FEATURE:
<223> OTHER INFORMATION: Synthetic construct

<400> SEQUENCE: 86

Gln Val Gln Leu Gln Gln Ser Gly Ala Glu Leu Val Lys Pro Gly Ala
1 5 10 15

Ser Val Lys Leu Ser Cys Lys Ala Ser Gly Tyr Thr Phe Thr
20 25 30

<210> SEQ ID NO 87
<211> LENGTH: 5
<212> TYPE: PRT
<213> ORGANISM: Artificial Sequence
<220> FEATURE:
<223> OTHER INFORMATION: Synthetic construct

<400> SEQUENCE: 87

Ser Tyr Asp Ile Asn
1 5

<210> SEQ ID NO 88
<211> LENGTH: 14
<212> TYPE: PRT
<213> ORGANISM: Artificial Sequence
<220> FEATURE:
<223> OTHER INFORMATION: Synthetic construct

<400> SEQUENCE: 88

Trp Val Arg Gln Arg Pro Glu Gln Gly Leu Glu Trp Ile Gly
1 5 10

<210> SEQ ID NO 89
<211> LENGTH: 17
<212> TYPE: PRT
<213> ORGANISM: Artificial Sequence
<220> FEATURE:
<223> OTHER INFORMATION: Synthetic construct

<400> SEQUENCE: 89

Trp Ile Phe Pro Gly Asp Gly Ser Ser Arg Tyr Asn Glu Lys Phe Lys
1 5 10 15

Gly

<210> SEQ ID NO 90
<211> LENGTH: 32
<212> TYPE: PRT
<213> ORGANISM: Artificial Sequence
<220> FEATURE:
<223> OTHER INFORMATION: Synthetic construct

<400> SEQUENCE: 90

Lys Ala Thr Leu Thr Thr Asp Lys Ser Ser Ser Thr Ala Tyr Met His
1 5 10 15

Leu Ser Arg Leu Thr Ser Glu Asp Ser Ala Val Tyr Phe Cys Ala Arg
20 25 30

<210> SEQ ID NO 91
<211> LENGTH: 9
<212> TYPE: PRT
<213> ORGANISM: Artificial Sequence
<220> FEATURE:
<223> OTHER INFORMATION: Synthetic construct

<400> SEQUENCE: 91

Gly Val Tyr Tyr Gly Asn Ser Asp Ser
1 5

<210> SEQ ID NO 92
<211> LENGTH: 11
<212> TYPE: PRT
<213> ORGANISM: Artificial Sequence
<220> FEATURE:
<223> OTHER INFORMATION: Synthetic construct

<400> SEQUENCE: 92

Trp Gly Gln Gly Thr Thr Leu Thr Val Ser Ser
1 5 10

<210> SEQ ID NO 93
<211> LENGTH: 324
<212> TYPE: PRT
<213> ORGANISM: Artificial Sequence
<220> FEATURE:
<223> OTHER INFORMATION: Synthetic construct

<400> SEQUENCE: 93

-continued

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 94
<211> LENGTH: 20
<212> TYPE: PRT
<213> ORGANISM: Artificial Sequence
<220> FEATURE:
<223> OTHER INFORMATION: Synthetic construct

<400> SEQUENCE: 94

Met Asp Ser Gln Ala Gln Val Leu Met Leu Leu Leu Leu Trp Val Ser
1               5                   10                  15

Gly Thr Cys Gly
            20
```

<210> SEQ ID NO 95
<211> LENGTH: 23
<212> TYPE: PRT
<213> ORGANISM: Artificial Sequence
<220> FEATURE:
<223> OTHER INFORMATION: Synthetic construct

<400> SEQUENCE: 95

```
Asp Ile Val Met Ser Gln Ser Pro Ser Ser Leu Ala Val Ser Val Gly
1               5                   10                  15

Glu Lys Val Thr Met Gly Cys
            20
```

<210> SEQ ID NO 96
<211> LENGTH: 17
<212> TYPE: PRT
<213> ORGANISM: Artificial Sequence
<220> FEATURE:
<223> OTHER INFORMATION: Synthetic construct

<400> SEQUENCE: 96

```
Lys Ser Ser Gln Ser Leu Leu Tyr Ser Ser Asn Gln Lys Asn Phe Leu
1               5                   10                  15

Ala
```

<210> SEQ ID NO 97
<211> LENGTH: 14
<212> TYPE: PRT
<213> ORGANISM: Artificial Sequence
<220> FEATURE:
<223> OTHER INFORMATION: Synthetic construct

<400> SEQUENCE: 97

```
Tyr Gln Gln Lys Pro Gly Gln Ser Pro Lys Leu Leu Ile Tyr
1               5                   10
```

<210> SEQ ID NO 98
<211> LENGTH: 7
<212> TYPE: PRT
<213> ORGANISM: Artificial Sequence
<220> FEATURE:
<223> OTHER INFORMATION: Synthetic construct

<400> SEQUENCE: 98

```
Trp Ala Ser Thr Arg Glu Ser
1               5
```

<210> SEQ ID NO 99
<211> LENGTH: 32
<212> TYPE: PRT
<213> ORGANISM: Artificial Sequence
<220> FEATURE:
<223> OTHER INFORMATION: Synthetic construct

<400> SEQUENCE: 99

```
Gly Val Pro Asp Arg Phe Thr Gly Ser Gly Ser Gly Thr Asp Phe Thr
1               5                   10                  15

Leu Thr Ile Ser Gly Val Lys Ala Glu Asp Leu Ala Val Tyr Tyr Cys
            20                  25                  30
```

<210> SEQ ID NO 100
<211> LENGTH: 9
<212> TYPE: PRT
<213> ORGANISM: Artificial Sequence
<220> FEATURE:
<223> OTHER INFORMATION: Synthetic construct -continued

<400> SEQUENCE: 100

```
Gln Gln Tyr Tyr Ser Tyr Pro Tyr Thr
1               5
```

<210> SEQ ID NO 101
<211> LENGTH: 10
<212> TYPE: PRT
<213> ORGANISM: Artificial Sequence
<220> FEATURE:
<223> OTHER INFORMATION: Synthetic construct

<400> SEQUENCE: 101

```
Phe Gly Gly Gly Thr Lys Leu Glu Ile Lys
1               5                   10
```

<210> SEQ ID NO 102
<211> LENGTH: 107
<212> TYPE: PRT
<213> ORGANISM: Artificial Sequence
<220> FEATURE:
<223> OTHER INFORMATION: Synthetic construct

<400> SEQUENCE: 102

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 103
<211> LENGTH: 57
<212> TYPE: DNA
<213> ORGANISM: Artificial Sequence
<220> FEATURE:
<223> OTHER INFORMATION: Synthetic construct

<400> SEQUENCE: 103

```
atgggatgga gctgggtctt tctcttcctc ctgtcagtaa ctgcaggtgt ccactcc        57
```

<210> SEQ ID NO 104
<211> LENGTH: 90
<212> TYPE: DNA
<213> ORGANISM: Artificial Sequence
<220> FEATURE:
<223> OTHER INFORMATION: Synthetic construct

<400> SEQUENCE: 104

```
caggttcagc tgcagcagtc tggagctgaa ctggtgaagc ctggggcttc agtgaagttg     60

tcctgcaagg cttctggcta caccttcaca                                      90
```

<210> SEQ ID NO 105
<211> LENGTH: 15

<212> TYPE: DNA
<213> ORGANISM: Artificial Sequence
<220> FEATURE:
<223> OTHER INFORMATION: Synthetic construct

<400> SEQUENCE: 105
agctatgata taaac 15

<210> SEQ ID NO 106
<211> LENGTH: 42
<212> TYPE: DNA
<213> ORGANISM: Artificial Sequence
<220> FEATURE:
<223> OTHER INFORMATION: Synthetic construct

<400> SEQUENCE: 106
tgggtgaggc agaggcctga acagggactt gagtggattg ga 42

<210> SEQ ID NO 107
<211> LENGTH: 51
<212> TYPE: DNA
<213> ORGANISM: Artificial Sequence
<220> FEATURE:
<223> OTHER INFORMATION: Synthetic construct

<400> SEQUENCE: 107
tggatttttc ctggagatgg tagttctagg tacaatgaga agttcaaggg c 51

<210> SEQ ID NO 108
<211> LENGTH: 96
<212> TYPE: DNA
<213> ORGANISM: Artificial Sequence
<220> FEATURE:
<223> OTHER INFORMATION: Synthetic constrct

<400> SEQUENCE: 108
aaggccacgc tgactacaga caaatcctcc agcacagcct acatgcatct cagcaggctg 60
acatctgagg actctgctgt ctatttctgt gcaaga 96

<210> SEQ ID NO 109
<211> LENGTH: 27
<212> TYPE: DNA
<213> ORGANISM: Artificial Sequence
<220> FEATURE:
<223> OTHER INFORMATION: Synthetic construct

<400> SEQUENCE: 109
ggggtttact atggtaactc tgactcc 27

<210> SEQ ID NO 110
<211> LENGTH: 33
<212> TYPE: DNA
<213> ORGANISM: Artificial Sequence
<220> FEATURE:
<223> OTHER INFORMATION: Synthetic construct

<400> SEQUENCE: 110
tggggccaag gcaccactct cacagtctcc tca 33

<210> SEQ ID NO 111
<211> LENGTH: 972
<212> TYPE: DNA
<213> ORGANISM: Artificial Sequence
<220> FEATURE:
<223> OTHER INFORMATION: Synthetic construct

<400> SEQUENCE: 111
gccaaaacga cacccccatc tgtctatcca ctggcccctg gatctgctgc ccaaactaac 60
tccatggtga ccctgggatg cctggtcaag ggctatttcc ctgagccagt gacagtgacc 120
tggaactctg gatccctgtc cagcggtgtg cacaccttcc cagctgtcct gcagtctgac 180
ctctacactc tgagcagctc agtgactgtc ccctccagca cctggcccag cgagaccgtc 240
acctgcaacg ttgcccaccc ggccagcagc accaaggtgg acaagaaaat tgtgcccagg 300
gattgtggtt gtaagccttg catatgtaca gtcccagaag tatcatctgt cttcatcttc 360
cccccaaagc ccaaggatgt gctcaccatt actctgactc ctaaggtcac gtgtgttgtg 420
gtagacatca gcaaggatga tcccgaggtc cagttcagct ggtttgtaga tgatgtggag 480
gtgcacacag ctcagacgca accccgggag gagcagttca acagcacttt ccgctcagtc 540
agtgaacttc ccatcatgca ccaggactgg ctcaatggca aggagttcaa atgcagggtc 600
aacagtgcag ctttccctgc ccccatcgag aaaaccatct ccaaaaccaa aggcagaccg 660
aaggctccac aggtgtacac cattccacct cccaaggagc agatggccaa ggataaagtc 720
agtctgacct gcatgataac agacttcttc cctgaagaca ttactgtgga gtggcagtgg 780
aatgggcagc cagcggagaa ctacaagaac actcagccca tcatggacac agatggctct 840
tacttcgtct acagcaagct caatgtgcag aagagcaact gggaggcagg aaatactttc 900
acctgctctg tgttacatga gggcctgcac aaccaccata ctgagaagag cctctcccac 960
tctcctggta aa 972

<210> SEQ ID NO 112
<211> LENGTH: 60
<212> TYPE: DNA
<213> ORGANISM: Artificial Sequence
<220> FEATURE:
<223> OTHER INFORMATION: Synthetic construct

<400> SEQUENCE: 112
atggattcac aggcccaggt tcttatgtta ctgctgctat gggtatctgg tacctgtggg 60

<210> SEQ ID NO 113
<211> LENGTH: 68
<212> TYPE: DNA
<213> ORGANISM: Artificial Sequence
<220> FEATURE:
<223> OTHER INFORMATION: Synthetic construct

<400> SEQUENCE: 113
gacattggat gtcacagtct ccatcctccc tagctgtgtc agttggagag aaggttacta 60
tgggctgc 68

<210> SEQ ID NO 114
<211> LENGTH: 51
<212> TYPE: DNA
<213> ORGANISM: Artificial Sequence
<220> FEATURE:
<223> OTHER INFORMATION: Synthetic construct

<400> SEQUENCE: 114
aagtccagtc agagcctttt atacagtagc aatcaaaaga acttcttggc c 51

<210> SEQ ID NO 115
<211> LENGTH: 45
<212> TYPE: DNA
<213> ORGANISM: Artificial Sequence
<220> FEATURE:
<223> OTHER INFORMATION: Synthetic construct

<400> SEQUENCE: 115
tggtaccagc agaaaccagg gcagtctcct aaactgctga tttac 45

<210> SEQ ID NO 116
<211> LENGTH: 21
<212> TYPE: DNA
<213> ORGANISM: Artificial Sequence
<220> FEATURE:
<223> OTHER INFORMATION: Synthetic construct

<400> SEQUENCE: 116
tgggcatcca cgagggaatc t 21

<210> SEQ ID NO 117
<211> LENGTH: 96
<212> TYPE: DNA
<213> ORGANISM: Artificial Sequence
<220> FEATURE:
<223> OTHER INFORMATION: Synthetic construct

<400> SEQUENCE: 117
ggggtccctg atcgcttcac aggcagtgga tctgggacag atttcactct caccatcagc 60
ggtgtgaagg ctgaagacct ggcagtttat tactgt 96

<210> SEQ ID NO 118
<211> LENGTH: 27
<212> TYPE: DNA
<213> ORGANISM: Artificial Sequence
<220> FEATURE:
<223> OTHER INFORMATION: Synthetic construct

<400> SEQUENCE: 118
cagcaatatt atagctatcc gtacacg 27

<210> SEQ ID NO 119
<211> LENGTH: 30
<212> TYPE: DNA
<213> ORGANISM: Artificial Sequence
<220> FEATURE:
<223> OTHER INFORMATION: Synthetic construct

<400> SEQUENCE: 119
ttcggagggg ggaccaagct ggaaataaaa 30

<210> SEQ ID NO 120
<211> LENGTH: 321
<212> TYPE: DNA
<213> ORGANISM: Artificial Sequence
<220> FEATURE:
<223> OTHER INFORMATION: Synthetic construct

<400> SEQUENCE: 120
cgggctgatg ctgcaccaac tgtatccatc ttcccaccat ccagtgagca gttaacatct 60
ggaggtgcct cagtcgtgtg cttcttgaac aacttctacc ccaaagacat caatgtcaag 120
tggaagattg atggcagtga acgacaaaat ggcgtcctga acagttggac tgatcaggac 180
agcaaagaca gcacctacag catgagcagc accctcacgt tgaccaagga cgagtatgaa 240
cgacataaca gctatacctg tgaggccact cacaagacat caacttcacc cattgtcaag 300
agcttcaaca ggaatgagtg t 321

<210> SEQ ID NO 121
<211> LENGTH: 461
<212> TYPE: PRT
<213> ORGANISM: Artificial Sequence
<220> FEATURE:
<223> OTHER INFORMATION: Synthetic construct

<400> SEQUENCE: 121

```
Met Gly Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Asp Ile Asn Trp Val Arg Gln Arg Pro Glu Gln Gly Leu
    50                  55                  60

Glu Trp Ile Gly Trp Ile Phe Pro Gly Asp Gly Ser Ser Arg Tyr Asn
65                  70                  75                  80

Glu Lys Phe Lys Gly Lys Ala Thr Leu Thr Thr Asp Lys Ser Ser Ser
                85                  90                  95

Thr Ala Tyr Met His Leu Ser Arg Leu Thr Ser Glu Asp Ser Ala Val
            100                 105                 110

Tyr Phe Cys Ala Arg Gly Val Tyr Tyr Gly Asn Ser Asp Ser Trp Gly
        115                 120                 125

Gln Gly Thr Thr Leu Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365
```

Lys Glu Gln Met Ala Lys Asp Lys Val Ser Leu Thr Cys Met Ile Thr
370 375 380

Asp Phe Phe Pro Glu Asp Ile Thr Val Glu Trp Gln Trp Asn Gly Gln
385 390 395 400

Pro Ala Glu Asn Tyr Lys Asn Thr Gln Pro Ile Met Asp Thr Asp Gly
405 410 415

Ser Tyr Phe Val Tyr Ser Lys Leu Asn Val Gln Lys Ser Asn Trp Glu
420 425 430

Ala Gly Asn Thr Phe Thr Cys Ser Val Leu His Glu Gly Leu His Asn
435 440 445

His His Thr Glu Lys Ser Leu Ser His Ser Pro Gly Lys
450 455 460

<210> SEQ ID NO 122
<211> LENGTH: 137
<212> TYPE: PRT
<213> ORGANISM: Artificial Sequence
<220> FEATURE:
<223> OTHER INFORMATION: Synthetic construct

<400> SEQUENCE: 122

Met Gly Trp Ser Trp Val Phe Leu Phe Leu Leu Ser Val Thr Ala Gly
1 5 10 15

Val His Ser Gln Val Gln Leu Gln Gln Ser Gly Ala Glu Leu Val Lys
20 25 30

Pro Gly Ala Ser Val Lys Leu Ser Cys Lys Ala Ser Gly Tyr Thr Phe
35 40 45

Thr Ser Tyr Asp Ile Asn Trp Val Arg Gln Arg Pro Glu Gln Gly Leu
50 55 60

Glu Trp Ile Gly Trp Ile Phe Pro Gly Asp Gly Ser Ser Arg Tyr Asn
65 70 75 80

Glu Lys Phe Lys Gly Lys Ala Thr Leu Thr Thr Asp Lys Ser Ser Ser
85 90 95

Thr Ala Tyr Met His Leu Ser Arg Leu Thr Ser Glu Asp Ser Ala Val
100 105 110

Tyr Phe Cys Ala Arg Gly Val Tyr Tyr Gly Asn Ser Asp Ser Trp Gly
115 120 125

Gln Gly Thr Thr Leu Thr Val Ser Ser
130 135

<210> SEQ ID NO 123
<211> LENGTH: 240
<212> TYPE: PRT
<213> ORGANISM: Artificial Sequence
<220> FEATURE:
<223> OTHER INFORMATION: Synthetic construct

<400> SEQUENCE: 123

Met Asp Ser Gln Ala Gln Val Leu Met Leu Leu Leu Leu Trp Val Ser
1 5 10 15

Gly Thr Cys Gly Asp Ile Val Met Ser Gln Ser Pro Ser Ser Leu Ala
20 25 30

Val Ser Val Gly Glu Lys Val Thr Met Gly Cys Lys Ser Ser Gln Ser
35 40 45

Leu Leu Tyr Ser Ser Asn Gln Lys Asn Phe Leu Ala Trp Tyr Gln Gln
50 55 60

Lys Pro Gly Gln Ser Pro Lys Leu Leu Ile Tyr Trp Ala Ser Thr Arg
65 70 75 80

```
Glu Ser Gly Val Pro Asp Arg Phe Thr Gly Ser Gly Ser Gly Thr Asp
                85                  90                  95

Phe Thr Leu Thr Ile Ser Gly Val Lys Ala Glu Asp Leu Ala Val Tyr
            100                 105                 110

Tyr Cys Gln Gln Tyr Tyr Ser Tyr Pro Tyr Thr Phe Gly Gly Gly Thr
        115                 120                 125

Lys Leu Glu Ile Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240


<210> SEQ ID NO 124
<211> LENGTH: 113
<212> TYPE: PRT
<213> ORGANISM: Artificial Sequence
<220> FEATURE:
<223> OTHER INFORMATION: Synthetic construct

<400> SEQUENCE: 124

Asp Ile Val Met Ser Gln Ser Pro Ser Ser Leu Ala Val Ser Val Gly
1               5                   10                  15

Glu Lys Val Thr Met Gly Cys Lys Ser Ser Gln Ser Leu Leu Tyr Ser
            20                  25                  30

Ser Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Gly Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys


<210> SEQ ID NO 125
<211> LENGTH: 1386
<212> TYPE: DNA
<213> ORGANISM: Artificial Sequence
<220> FEATURE:
<223> OTHER INFORMATION: Synthetic construct

<400> SEQUENCE: 125

atgggatgga gctgggtctt tctcttcctc ctgtcagtaa ctgcaggtgt ccactcccag      60

gttcagctgc agcagtctgg agctgaactg gtgaagcctg gggcttcagt gaagttgtcc     120

tgcaaggctt ctggctacac cttcacaagc tatgatataa actgggtgag gcagaggcct     180
```

```
gaacagggac ttgagtggat tggatggatt tttcctggag atggtagttc taggtacaat    240
gagaagttca agggcaaggc cacgctgact acagacaaat cctccagcac agcctacatg    300
catctcagca ggctgacatc tgaggactct gctgtctatt tctgtgcaag aggggtttac    360
tatggtaact ctgactcctg ggccaaggc accactctca cagtctcctc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc accaggactg gctcaatggc aaggagttca aatgcagggt caacagtgca   1020
gctttccctg cccccatcga gaaaaccatc tccaaaacca aaggcagacc gaaggctcca   1080
caggtgtaca ccattccacc tcccaaggag cagatggcca aggataaagt cagtctgacc   1140
tgcatgataa cagacttctt ccctgaagac attactgtgg agtggcagtg gaatgggcag   1200
ccagcggaga actacaagaa cactcagccc atcatggaca cagatggctc ttacttcgtc   1260
tacagcaagc tcaatgtgca gaagagcaac tgggaggcag gaaatacttt cacctgctct   1320
gtgttacatg agggcctgca caaccaccat actgagaaga gcctctccca ctctcctggt   1380
aaatga                                                              1386
```

```
<210> SEQ ID NO 126
<211> LENGTH: 723
<212> TYPE: DNA
<213> ORGANISM: Artificial Sequence
<220> FEATURE:
<223> OTHER INFORMATION: Synthetic construct

<400> SEQUENCE: 126

atggattcac aggcccaggt tcttatgtta ctgctgctat gggtatctgg tacctgtggg     60
gacattgtga tgtcacagtc tccatcctcc ctagctgtgt cagttggaga gaaggttact    120
atgggctgca agtccagtca gagcctttta tacagtagca atcaaaagaa cttcttggcc    180
tggtaccagc agaaaccagg gcagtctcct aaactgctga tttactgggc atccacgagg    240
gaatctgggg tccctgatcg cttcacaggc agtggatctg ggacagattt cactctcacc    300
atcagcggtg tgaaggctga agacctggca gtttattact gtcagcaata ttatagctat    360
ccgtacacgt tcggaggggg gaccaagctg gaaataaaac gggctgatgc tgcaccaact    420
gtatccatct tcccaccatc cagtgagcag ttaacatctg gaggtgcctc agtcgtgtgc    480
ttcttgaaca acttctaccc caaagacatc aatgtcaagt ggaagattga tggcagtgaa    540
cgacaaaatg gcgtcctgaa cagttggact gatcaggaca gcaaagacag cacctacagc    600
atgagcagca ccctcacgtt gaccaaggac gagtatgaac gacataacag ctatacctgt    660
gaggccactc acaagacatc aacttcaccc attgtcaaga gcttcaacag gaatgagtgt    720
tag                                                                 723
```